United States Patent [19]

Fischli et al.

[11] Patent Number: 4,766,133
[45] Date of Patent: Aug. 23, 1988

[54] (BEZIMIDAZOL-2-YL)-PYRIDINIUM COMPOUNDS

[75] Inventors: Albert Fischli, Riehen; Anna Krassó, Basel; André Szente, Riehen, all of Switzerland

[73] Assignee: Hoffman-La Roche Inc., Nutley, N.J.

[21] Appl. No.: 893,856

[22] Filed: Aug. 6, 1986

[30] Foreign Application Priority Data

Aug. 12, 1985 [CH] Switzerland ............ 3455/85
Jun. 10, 1986 [CH] Switzerland ............ 2350/86

[51] Int. Cl.⁴ .................... C07D 401/04; A61K 31/44
[52] U.S. Cl. ......................... 514/338; 546/271; 546/193; 546/256; 544/215; 544/318; 544/315; 514/262; 514/318; 514/269; 514/333
[58] Field of Search .............. 546/271, 193; 514/338

[56] References Cited

U.S. PATENT DOCUMENTS

| 4,045,563 | 8/1977 | Berntsson et al. | 546/271 |
| 4,182,766 | 1/1980 | Krasso et al. | 546/271 |
| 4,435,406 | 3/1984 | Krasso et al. | 546/271 |
| 4,634,710 | 1/1987 | Fischli et al. | 546/271 |

FOREIGN PATENT DOCUMENTS

| 0181846 | 5/1986 | European Pat. Off. |
| 3240248 | 1/1983 | Fed. Rep. of Germany |
| 2134523 | 8/1984 | United Kingdom |

Primary Examiner—Jane T. Fan
Attorney, Agent, or Firm—Jon S. Saxe; Bernard S. Leon; Matthew Boxer

[57] ABSTRACT (Benzimidazol-2-yl)-pyridinium compounds of the formula

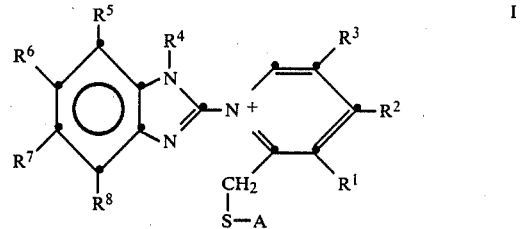

wherein A is $-SR^9$, $-SO_3^-$ or $-S-SO_3^-$; $R^1$ and $R^3$ each is hydrogen or $(C_1-C_7)$-alkyl; $R^2$ is hydrogen, $(C_1-C_7)$-alkyl, $(C_1-C_7)$-alkoxy or a negatively charged oxygen atom; $R^4$ is hydrogen or a negative charge; $R^5$, $R^6$, $R^7$ and $R^8$ each is hydrogen, $(C_1-C_7)$-alkyl, aryl, halogen, cyano, nitro, formyl, $(C_2-C_7)$-alkanoyl, arylcarbonyl, carboxy, carboxy-$(C_1-C_7)$-alkyl, $(C_1-C_7)$-alkoxycarbonyl, aryloxycarbonyl, aryl-$(C_1-C_7)$-alkoxycarbonyl, $(C_1-C_7)$-alkoxycarbonyl-$(C_1-C_7)$-alkyl, carbamoyl, mono- or di-$(C_1-C_7)$-alkylcarbamoyl, pyrrolidinocarbonyl, piperidinocarbonyl, carbamoyl-$(C_1-C_7)$-alkyl, mono- or di-$(C_1-C_7)$-alkylcarbamoyl-$(C_1-C_7)$-alkyl, pyrrolidinocarbonyl-$(C_1-C_7)$-alkyl, piperdinocarbonyl-$(C_1-C_7)$-alkyl, hydroxy, $(C_1-C_7)$-alkoxy, $(C_2-C_7)$-alkanoloxy, aryloxy, arylcarbonyloxy, $(C_1-C_7)$-alkoxycarbonyloxy, aryl-$(C_1-C_7)$-alkoxycarbonyloxy, aryloxycarbonyloxy, carbamoyloxy, mono- or di-$(C_1-C_7)$-alkylcarbamoyloxy, pyrrolidinocarbonyloxy, piperidinocarbonyloxy, hydroxy-$(C_1-C_7)$-alkyl, trifluoromethyl, di-$(C_1-C_7)$-alkoxymethyl or $(C_2-C_3)$-alkylenedioxymethyl or two of these substituents which are adjacent jointly and together with the carbon atoms to which they are attached are a 5-, 6- or 7-membered ring; and $R^9$ is $(C_1-C_{20})$-alkyl, $(C_3-C_7)$-cycloalkyl, $(C_3-C_7)$-alkenylalkyl, $(C_3-C_7)$-alkynylalkyl, substituted $(C_3-C_7)$- alkenyl-alkyl, aryl, aryl-$(C_1-C_7)$-alkyl, hydroxy- $(C_2-C_7)$-alkyl, $(C_1-C_7)$-alkoxy-$(C_2-C_7)$-alkyl, $(C_1-C_7)$-alkoxycarbonyl- $(C_1-C_7)$-alkyl, carboxy-$(C_1-C_7)$-alkyl, di-$(C_1-C_7)$-alkoxycarbonyl-$(C_2-C_7)$-alkyl, dicarboxy-$(C_2-C_7)$-alkyl, carboxy-$(C_1-C_7)$-alkylcarbamoyl-$(C_1-C_7)$-alkyl, optionally N-substituted amino-$(C_2-C_7)$-alkyl, optionally N-substituted amino-carboxy-$(C_2-C_7)$-alkyl, optionally N-substituted amino-$(C_1-C_7)$-alkoxycarbonyl-$(C_2-C_7)$-alkyl, heteroaryl, heteroaryl-$(C_1-C_7)$-alkyl or a residue derived from a cysteine-containing oligopeptide by elimination of the SH group;

provided that when there is a net single positive charge there is an external anion, or a pharmaceutically acceptable acid addition salt thereof.

33 Claims, No Drawings

(BEZIMIDAZOL-2-YL)-PYRIDINIUM COMPOUNDS

BRIEF SUMMARY OF THE INVENTION

The invention relates to benzimidazole derivatives of the formula

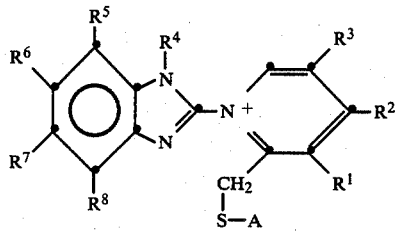

wherein

A is $-SR^9$, $-SO_3^-$ or $-S-SO_3^-$;

$R^1$ and $R^3$ each is hydrogen or $(C_1-C_7)$-alkyl;

$R^2$ is hydrogen, $(C_1-C_7)$-alkyl $(C_1-C_7)$-alkoxy or a negatively charged oxygen atom;

$R^4$ is hydrogen or a negative charge;

$R^5$, $R^6$, $R^7$ and $R^8$ each is hydrogen, $(C_1-C_7)$-alkyl, aryl, halogen, cyano, nitro, formyl, $(C_2-C_7)$-alkanoyl, arylcarbonyl, carboxy, carboxy-$(C_1-C_7)$-alkyl, $(C_1-C_7)$-alkoxycarbonyl, aryloxycarbonyl, aryl-$(C_1-C_7)$-alkoxycarbonyl, $(C_1-C_7)$-alkoxycarbonyl-$(C_1-C_7)$-alkyl, carbamoyl, mono- or di-$(C_1-C_7)$-alkylcarbamoyl, pyrrolidinocarbonyl, piperidinocarbonyl, carbamoyl-$(C_1-C_7)$-alkyl, mono- or di-$(C_1-C_7)$-alkylcarbamoyl-$(C_1-C_7)$-alkylcarbamoyl-$(C_1-C_7)$-alkyl, pyrrolidinocarbonyl-$(C_1-C_7)$-alkyl, piperidinocarbonyl-$(C_1-C_7)$-alkyl, hydroxy, $(C_1-C_7)$-alkoxy, $(C_2-C_7)$-alkanoyloxy, aryloxy, arylcarbonyloxy, $(C_1-C_7)$-alkoxycarbonyloxy, aryl-$(C_1-C_7)$-alkoxycarbonyloxy, aryloxycarbonyloxy, carbamoyloxy, mono- or di-$(C_1-C_7)$-alkylcarbamoyloxy., Pyrrolidinocarbonyloxy, Piperidinocarbonyloxy, hydroxy-$(C_1-C_7)$-alkyl, trifluoromethyl, di-$(C_1-C_7)$-alkoxymethyl or $(C_2-C_3)$-alkylenedioxymethyl or two of these substituents which are adjacent jointly and together with the carbon atoms to which they are attached is a 5- 6- or 7-membered ring; and $R^9$ is $(C_1-C_{20})$-alkyl, $(C_3-C_7)$-cycloalkyl, $(C_3-C_7)$-alkenylalkyl, $(C_3-C_7)$-alkynylalkyl, substituted $(C_3-C_7)$-alkenylalkyl, aryl, aryl-$(C_1-C_7)$-alkyl, hydroxy-$(C_2-C_7)$-alkyl, $(C_1-C_7)$-alkoxy-$(C_2-C_7)$-alkyl, $(C_1-C_7)$-alkoxycarbonyl-$(C_1-C_7)$ -alkyl, carboxy-$(C_1-C_7)$-alkyl, di-$(C_1-C_7)$-alkoxycarbonyl-$(C_2-C_7)$-alkyl, dicarboxy-$(C_2-C_7)$-alkyl, carboxy-$(C_1-C_7)$-alkylcarbamoyl-$(C_1-C_7)$-alkyl, optionally N-substituted amino-$(C_2-C_7)$-alkyl, optionally N-substituted amino-carboxy-$(C_2-C_7)$-alkyl, optionally N-substituted amino-$(C_1-C_7)$-alkoxycarbonyl -$(C_2-C_7)$-alkyl, heteroaryl, heteroaryl-$(C_1-C_7)$-alkyl or a residue derived from a cysteine-containing oligopeptide by elimination of the SH group;

whereby the molecule as a whole is non-charged or has a single positive charge and whereby in the latter case an external anion is present; as well as pharmaceutically acceptable acid addition salts of basically-substituted compounds of formula I. The compounds of formula I are gastric acid secretion-inhibiting and/or mucosa-protecting (especially against indomethacin-induced lesions), so that they are useful as agents for the control or prevention of illnesses of the gastrointestinal tract, especially against gastric ulcers and duodenal ulcers.

Objects of the present invention are the compounds and salts defined earlier as therapeutically active substances, medicaments containing such a compound or a salt thereof, the manufacture of such medicaments, the use of the compounds and salts defined earlier in the control or prevention of illnesses, especially in the control or prevention of gastric ulcers and duodenal ulcers, or the use of the compounds and salts defined earlier for the manufacture of medicaments for the control or prevention of gastric ulcers and duodenal ulcers, as well as compounds and salts defined earlier per se and the manufacture of these compounds and salts.

DETAILED DESCRIPTION OF THE INVENTION

The invention relates to compounds of the formula

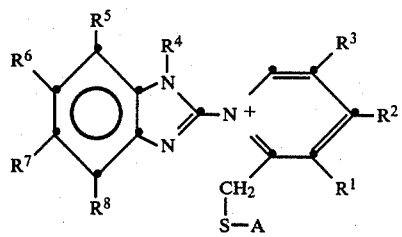

wherein

A is $-SR^9$, $-SO_3^-$ or $-S-SO_3^-$;

$R^1$ and $R^3$ each is hydrogen or $(C_1-C_7)$-alkyl:

$R^2$ is hydrogen, $(C_1-C_7)$-alkyl, $(C_1-C_7)$-alkoxy or a negatively charged oxygen atom;

$R^4$ is hydrogen or a negative charge;

$R^5$, $R^6$, $R^7$ and $R^8$ each is hydrogen, $(C_1-C_7)$-alkyl, aryl, halogen, cyano, nitro, formyl, $(C_2-C_7)$-alkanoyl, arylcarbonyl, carboxy, carboxy-$(C_1-C_7)$-alkyl, $(C_1-C_7)$-alkoxycarbonyl, aryloxycarbonyl, aryl-$(C_1-C_7)$-alkoxycarbonyl, $(C_1-C_7)$-alkoxycarbonyl-$(C_1-C_7)$-alkyl, carbamoyl, mono- or di-$(C_1-C_7)$-alkylcarbamoyl, pyrrolidinocarbonyl piperidinocarbonyl, carbamoyl-$(C_1-C_7)$-alkyl, mono- or di-$(C_1-C_7)$-alkylcarbamoyl-$(C_1-C_7)$-alkyl, pyrrolidinocarbonyl-$(C_1-C_7)$-piperidinocarbonyl-$(C_1-C_7)$-alkyl, hydroxy, $(C_1-C_7)$-alkoxy, $(C_2-C_7)$-alkanoyloxy, aryloxy, arylcarbonyloxy, $(C_1-C_7)$-alkoxycarbonyloxy, aryl-$(C_1-C_7)$-alkoxycarbonyloxy, aryloxycarbonyloxy, carbamoyloxy, mono- or di-$(C_1-C_7)$-alkylcarbamoyloxy, pyrrolidinocarbonyloxy, piperidinocarbonyloxy, hydroxy-$(C_1-C_7)$-alkyl, trifluoromethyl, di-$(C_1-C_7)$-alkoxymethyl or $(C_2-C_3)$-alkylenedioxymethyl or two of these substituents which are adjacent jointly and together with the carbon atoms to which they are attached is a 5-, 6- or 7-membered ring; and $R^9$ is $(C_1-C_{20})$-alkyl, $(C_3-C_7)$-cycloalkyl, $(C_3-C_7)$-alkenylalkyl, $(C_3-C_7)$-alkynylalkyl, substituted $(C_3-C_7)$-alkenylalkyl, aryl, aryl-$(C_1-C_7)$-alkyl, hydroxy-$(C_2-C_7)$-alkyl, $(C_1-C_7)$-alkoxy-$(C_2-C_7)$-alkyl, $(C_1-C_7)$-alkoxycarbonyl-$(C_1-C_7)$-alkyl, carboxy-$(C_1-C_7)$-alkyl, di-$(C_1-C_7)$-alkoxycarbonyl-$(C_2-C_7)$-alkyl, dicarboxy-$(C_2-C_7)$-alkyl, carboxy-$(C_1-C_7)$-alkylcarbamoyl-$(C_1-C_7)$-alkyl optionally N-substituted amino-$(C_2-C_7)$-alkyl, optionally N-substituted amino-carboxy-$(C_2-C_7)$-alkyl, optionally N-substituted amino-$(C_1-C_7)$-alkoxycarbonyl-$(C_2-C_7)$-alkyl, heteroaryl, heteroaryl-$(C_1-C_7)$-alkyl or a residue derived from a cysteine-containing oligopeptide by elimination of the SH group;

provided that when there is a net single positive charge there is an external anion, as well as pharmaceutically acceptable acid addition salts of basically-substituted compounds of formula I.

The compounds of formula I possess valuable pharmacodynamic properties, namely gastric acid secretion-inhibiting and/or mucosa-protective properties (especially against indomethacin-induced lesions), so that they are useful as agents for the control or prevention of illnesses of the gastrointestinal tract, especially against gastric ulcers and duodenal ulcers.

Objects of the present invention are the compounds and salts defined earlier as therapeutically active substances, medicaments containing such a compound or a salt thereof. The manufacture of such medicaments, the use of the compounds and salts defined earlier in the control or prevention of illnesses, especially in the control or prevention of gastric ulcers and duodenal ulcers, or the use of the compounds and salts defined earlier for the manufacture of medicaments for the control or prevention of gastric ulcers and duodenal ulcers, as well as compounds and salts defined earlier per se and the manufacture of these compounds and salts.

When the molecule as a whole is non-charged then the (benzimidazol-2-yl)-pyridinium compounds of formula I are internal salts. Internal salts are referred to in the compound names which follow as intramolecularly deprotonized cations, as for example: intramolecularly deprotonized 2-[(3-furfuryldithio)-methyl]-4-methoxy-3-methyl-1-(1.5,6,7-tetrahydro-5,5,7,7-tetramethyl-6-oxoindeno[5,6-d]imidazol-1-yl)pyridinium cation. This is the case when either A is —SR$^9$ and R$^9$ carries a negatively charged group or A is —SO$_3^-$ or —S—SO$_3^-$ or R$^4$ is a negative charge or R$^2$ is a negatively charged oxygen atom; in the latter case the compounds of formula I can also be viewed as pyridone derivatives with the formula

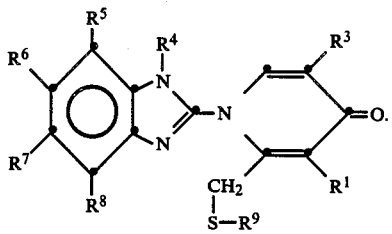

Ia

Basically-substituted compounds of formula I can also form acid addition salts, including pharmaceutically acceptable acid addition salts. From the substitution pattern of a compound of formula I, it can readily be determined, whether that particular compound is a basic compound, which can, if desired be converted into a pharmaceutically acceptable acid addition salt.

The term "alkyl" denotes straight-chain or branchad saturated hydrocarbon residues such as methyl, ethyl, n-propyl, i-propyl, sec-butyl, t-butyl, n-pentyl, n-hexyl, n-octyl, t-octyl, n-dodecyl, n-hexadecyl and n-octadecyl, The term "alkoxy" denotes alkyl groups as described above attached via an oxygen atom.

The term "aryl" denotes mono- or polynuclear aromatic hydrocarbon residues which can be substituted, for example by halogen, trifluoromethyl, nitro, optionally N-substituted amino, (C$_1$-C$_7$)-alkyl, carboxy or (C$_1$-C$_7$)-alkoxycarbonyl; examples of such aryl residues are phenyl, o-tolyl, p-tolyl, o-chlorophenyl, m-chlorophenyl, p-chlorophenyl, 2,3-dichlorophenyl, 2,4-dichlorophenyl, 2,5-dichlorophenyl, 2,6-dichlorophenyl, 3,4-dichlorophenyl, m-bromophenyl, p-bromophenyl, m-fluorophenyl, p-fluorophenyl, pentafluorophenyl, o-carboxyphenyl, o-methoxycarbonylphenyl, o-methoxyphenyl, m-methoxyphenyl, p-methoxyphenyl, o-nitrophenyl, m-nitrophenyl, p-nitrophenyl, o-aminophenyl, m-aminophenyl, p-acetylaminophenyl and m-trifluoromethylphenyl, The term "halogen" denotes chlorine, fluorine, bromine and iodine. The term "alkylene" denotes methylene and polymethylene chains. The term "cycloalkyl" denotes unsubstituted cycloaliphatic residues such as cyclopentyl and cyclohexyl and substituted cycloaliphatic residues as well. The terms "alkenylalkyl" and "alkynylalkyl" denote hydrocarbon residues which contain a carbon-carbon double or triple bond and in which the carbon atom via which they are attached to the remainder of the compound is not unsaturated, e.g. residues such as allyl, The term "substituted alkenylalkyl" denotes an alkenylalkyl residue as previously described which is substituted vinylically, especially by halogen such as chlorine; 2-chloroallyl is an example of such a residue. The terms "dicarboxyalkyl" and "di-alkoxycarbonylalkyl" denote alkyl residues which are substituted by two carboxy groups or alkoxycarbonyl groups which are not, however, situated on the same carbon atom. The term "N-substituted" means that an amino group is mono-substituted by (C$_1$-C$_7$)-alkyl or (C$_1$-C$_7$)-alkanoyl or is di-substituted by (C$_1$-C$_7$)-alkyl and (C$_1$-C$_7$)-alkanoyl or by two (C$_1$-C$_7$)-alkyl residues. The term "heteroaryl" denotes mono- or polynuclear heteroaromatic residues, especially those which contain 1–4 nitrogen atoms and-/or an oxygen or sulphur atom as the hetero atom or hetero atoms and which can be optionally substituted, for example by (C$_1$-C$_7$)-alkyl, aryl, hydroxy, optionally N-substituted amino or nitro; examples of such heteroaryl residues are 2-pyridyl, 4-pyridyl, 2-pyrimidinyl, 1-H-s-triazol-3-yl, purin-6-yl, furyl, 4,6-di-methyl-2-pyrimidinyl, 5-amino-1,3,4-thiadiazol-2-yl, 5-methyl-1,3,4-thiadiazol-2-yl, 4-methyl-4H-1,2,4-triazol-3-yl, 1-phenyl-1H-tetrazol-5-yl, 4-hydroxy-6-propyl-2-pryimidinyl, 2-benzimidazolyl, 5-nitro-2-benzimidazolyl and the like. The term "cysteine-containing oligopeptide" denotes a peptide containing 2–10 amino acids, with one of these amino acids being cysteine; an example of such an oligopeptide is glutathione ($\gamma$-glutamylcysteinylglycine). The term "alkanoyl" denotes residues such as acetyl, propionyl and the like. The term "aminocarboxyalkyl" includes residues such as 2-amino-2-carboxyethyl, 3-amino-3-carboxyethyl and 2-amino-2-carboxy-1,1-dimethylethyl, The term "aminoalkoxycarbonyl" includes residues such as 2-amino-2-ethoxycarbonylethyl and the like.

The 5-, 6- or 7-membered ring which two adjacent substituents R$^5$, R$^6$, R$^7$ and R$^8$ jointly and together with the carbon atoms to which they are attached can form is heterocyclic or carbocyclic, it optionally contains one or more additional double bonds, it may be aromatic or non-aromatic, and it is optionally substituted; as substituents there come in to consideration hydroxy, (C$_1$-C$_7$)-alkyl, (C$_1$-C$_7$)-alkoxy, (C$_2$-C$_7$-alkanoyloxy, oxo, oximino, (C$_1$-C$_7$)-alkoxyimino or the like. when such a ring is present, then the other two substituents in question preferably each is hydrogen. When R$^5$ and R$^6$ jointly and together with the carbon atoms to which they are attached are such a ring, then this is, for example, a thiazole, thiadiazole or 1,3-dioxane ring. when $R^6$ and $R^7$ jointly and together with the carbon atoms to which they are attached form such a ring, then this is, for example, a ring of the formula

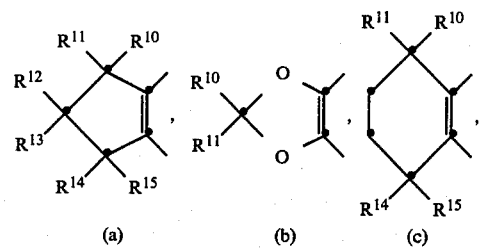

(a)    (b)    (c)

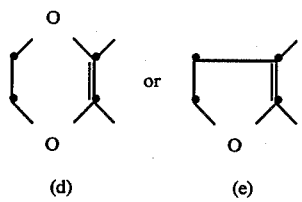

(d)    (e)

wherein
$R^{10}$, $R^{11}$, $R^{14}$ and $R^{15}$ each is hydrogen or $(C_1-C_7)$-alkyl; and
either $R^{12}$ is hydrogen and $R^{13}$ is hydrogen, hydroxy, $(C_1-C_7)$-alkoxy or $(C_2-C_7)$-alkanoyloxy or $R^{12}$ and $R^{13}$ together are oxo, oximino or $(C_1-C_7)$-alkoxyimino.
preferably, in this case $R^{10}$, $R^{11}$, $R^{14}$ and $R^{15}$ either all are hydrogen or all are methyl and $R^{12}$ and $R^{13}$ together are oxo. particularly preferred are the rings of formulae (a), (b) and (c) above.

when none of the substituents $R^5$, $R^6$, $R^7$ and $R^8$ is part of a ring, then preferably $R^5$ and $R^8$ each is hydrogen. Furthermore, in such a case $R^7$ preferably also is hydrogen, and $R^6$ preferably is hydrogen, methoxy or trifluoromethyl, $R^1$ is, for example, hydrogen or methyl, $R^2$ is, for example, hydrogen, methyl t-butyl, methoxy, ethoxy n-propoxy or a negatively charged oxygen atom. $R^3$ is, for example, hydrogen or methyl, when A is $SR^9$, then $R^9$ is, for example, methyl, ethyl, n-propyl, i-propyl, s-butyl, t-butyl, n-pentyl, n-hexyl, n-octyl, t-octyl, n-dodecyl, n-hexadecyl, n-octadecyl, allyl, 2-chloroallyl, cyclopentyl, cyclohexyl, 2-hydroxyethyl, methoxycarbonylmethyl, ethoxycarbonylmethyl, 1,2-dicarboxyethyl, 1,2-bis-(ethoxycarbonyl)ethyl, carbomymethyl, 2-carboxyethyl, 1-carboxyethyl, 2-amino-2-carboxyethyl, 2-amino-2-ethoxycarbonylethyl, 3-amino-3-carboxypropyl, 2-amino-2-carboxy-1,1-dimethylethyl, phenyl, p-tolyl, m-chlorophenyl, o-carboxyphenyl, p-fluorophenyl, p-chlorophenyl, m-methoxyphenyl, pentafluorophenyl, o-tolyl, o-chlorophenyl, m-fluorophenyl, p-methoxyphenyl, o-methoxyphenyl, 2,6-dichlorophenyl, 2,5-dichlorophenyl, 2,3-dichlorophenyl, 2,4-dichlorophenyl, 3,4-dichlorophenyl, o-methoxycarbonylphenyl, p-nitrophenyl, m-bromophenyl, p-bromophenyl, m-aminophenyl, o-aminophenyl, p-acetylaminophenyl, m-trifluoromethylphenyl, benzyl, o-nitrobenzyl, p-fluorobenzyl, p-methoxybenzyl, m-trifluoromethylbenzyl, 2-phenylethyl, o-chlorobenzyl, p-chlorobenzyl, m-nitrobenzyl, 3,4-dichlorobenzyl, 2,4-dichlorobenzyl, triphenylmethyl, 2-pyridyl, 2-pyrimidinyl, 5-amino-1,3,4-thiadiazol-2-yl, 1H-s-triazol-3-yl, purin-6-yl, 4,6-dimethyl-2-pyrimidinyl, furfuryl, 5-methyl-1,3,4-thiadiazol-2-yl, 4-methyl-4H-1,2,4-triazol-3-yl, 1-phenyl-1H-tetrazol-5-yl, 4-hydroxy-6-propyl-2-pyrimidinyl 2-benzimidazolyl, 4-pyridyl, 5-nitro-2-benzimidazolyl, 2-(4-amino-4-carboxy-butyramido)-2-(carboxymethylcarbamoyl)ethyl, 1-[(carboxymethyl)carbamoyl]ethyl, 2-aminoethyl or 2-dimethylaminoethyl; A is also $-SO_3^-$ or $-S-SO_3^-$.

The external anion is a pharmaceutically acceptable anion such as the anion from sulfuric acid, hydrobromic acid, methanesulphonic acid, and most preferably hydrochloric acid.

The compounds of formula I may alternatively be depicted by the following formula

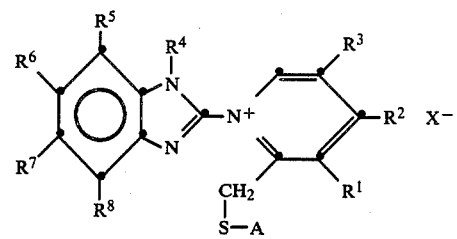

Ib wherein
A, $R^1$, $R^2$, $R^3$, $R^4$, $R^5$, $R^6$, $R^7$, $R^8$ and $R^9$ are as described above and $X^-$ is an external anion which is present when there is a single net positive charge on the remainder of the molecule.

Among the compounds of formula I described above there are preferred those in which $R^1$ is $(C_1-C_7)$-alkyl, $R^2$ is $(C_1-C_7)$-alkoxy. $R^3$ is hydrogen or $(C_1-C_7)$-alkyl, A is $-SR^9$, $R^9$ is n-propyl, 2-amino-2-carboxyethyl, 2-(4-amino-4-carboxybutyramido)-2-(carboxy-methylcarbamoyl)ethyl, n-hexyl, o-chlorophenyl, ethyl, 2-aminoethyl, m-chlorophenyl, 1,2-bis-(ethoxycarbonyl)-ethyl, 2-amino-2-ethoxycarbonylethyl, 2-hydroxyethyl, 3-amino-3-carboxypropyl, cyclopentyl, 2-dimethylaminoethyl, o-carboxyphenyl, isopropyl, 2-pyrimidinyl, p-fluorophenyl, 2-carboxyethyl, 1-carboxyethyl, p-chlorophenyl, 3-furfuryl, n-pentyl, 2-chloroallyl, o-nitrobenzyl, 3,4-dichlorophenyl, p-methoxyphenyl, 5-nitro-2-benzimidazolyl, 1-[(carboxymethyl)carbamoyl]ethyl or o-chlorophenyl, $R^5$ and $R^8$ each is hydrogen and either $R^6$ is trifluoromethyl and $R^7$ g is hydrogen or $R^6$ and $R^7$ together with the carbon atoms to which they are attached are

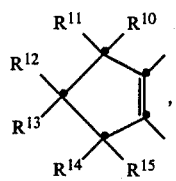

wherein
$R^{10}$, $R^{11}$, $R^{12}$, $R^{13}$, $R^{14}$, and $R^{15}$ are as described above. Of these compounds there are especially preferred those in which $R^1$ is methyl, $R^2$ is methoxy and $R^3$ is hydrogen or methyl and in which, when $R^6$ and $R^7$ together with the carbon atoms to which they are attached is,

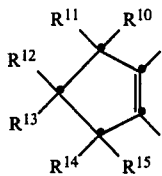

$R^{12}$ and $R^{13}$ together are oxo and $R^{10}$, $R^{11}$, $R^{14}$ and $R^{15}$ all are methyl, particularly preferred compounds of formula I are:

2-[(propyldithio)methyl]-4-methoxy-3-methyl-1-[5-(trifluoromethyl)-2-benzimidazolyl]pyridinium chloride:

2-[[[(R)-2-amino-2-carboxyethyl]dithio]methyl]-4-methoxy-3-methyl-1-[5-(trifluoromethyl)-2-benzimidazolyl]pyridinium chloride; and 2-[[[(R)-2-[(S)-4-amino-4-carboxybutyramido]-2-[(carboxymethyl)carbamoyl]ethyl]dithio]methyl]-4-methoxy-3-methyl-1-[(5-trifluoromethyl)-2-benzimidazolyl]pyridinium chloride.

Further especially preferred compounds of formula I are:

2-[(Hexyldithio)methyl]-4-methoxy-3-methyl-1-[5-(trifluoromethyl)-2-benzimidazolyl]pyridinium chloride;

2-[[(o-chlorophenyl)dithio]methyl]-4-methoxy-3-methyl-1-[5-(trifluoromethyl)-2-benzimidazolyl]pyridinium chloride:

2-[(ethyldithio)methyl]-4-methoxy-3-methyl-1-[5-(trifluoromethyl)-2-benzimidazolyl]pyridinium chloride;

2-[[(2-aminoethyl)dithio]methyl]-4-methoxy-3-methyl-1-[5-(trifluoromethyl)-2-benzimidazolyl]pyridinium chloride;

2-[[(m-chlorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[[(R)-2-amino-2-carboxyethyl]dithio]methyl]-4-methoxy-3-methyl-1-(5,6,7-tetrahydro-5,5,7,7-tetramethyl-6-oxoindeno[5,6-d]imidazol-2-yl)pyridinium chloride;

2-[[[1,2-bis-(ethoxycarbonyl)ethyl]dithio]methyl]-4-methoxy-3-methyl-1-[5-(trifluoromethyl)-2-benzimidazolyl]pyridinium chloride;

2-[(ethyldithio)methyl]-4-methoxy-3-methyl-1-(1,5,6,7-tetrahydro-5,5,7,7-tetramethyl-6-oxoindeno[5,6-d]imidazol-2-yl)pyridinium chloride;

4-methoxy-3-methyl-2-[(propyldithio)methyl]-1-(1,5,6,7-tetrahydro-5,5,7,7-tetramethyl-6-oxoindeno[5,6-d]imidazol-2-yl)pyridinium chloride;

2-[[[(R)-2-amino-2-(ethoxycarbonyl)ethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

intramolecularly deprotonized 3-[[[2-(dimethylaminoethyl]dithio]methyl]-4-methoxy-3-methyl-1-(1,5,6,7-tetrahydro-5,5,7,7-tetramethyl-6-oxoindeno[5,6-d]imidazol-2-yl)pyridinium cation;

2-[[(2-hydroxyethyl)dithio]methyl]-4-methoxy-3methyl-1-(1,5,6,7-tetrahydro-5,5,7,7-tetramethyl-6-oxoindeno[5,6-d]imidazol-2-yl)pyridinium chloride;

2-[[[(RS)-3-amino-3-carboxypropyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride; and 2-[(cyclopentyldithio)methyl]-4-methoxy-3-methyl-1-(1,5,6,7-tetrahydro-5,5,7,7-tetramethyl-6-oxoindeno[5,6-d]imidazol-2-yl)pyridinium chloride;

Likewise preferred compounds of formula I are, for example:

2-[[(o-Carboxyphenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[(isopropyldithio)methyl]-4-methoxy-3-methyl-1-(1,5,6,7-tetrahydro-5,5,7,7-tetramethyl-6-oxoindeno[5,6-d]imidazol-2-yl)pyridinium chloride;

2-[(2-pyrimidinyldithio)methyl]-4-methoxy-3-methyl-1-(1,5,6,7,-tetrahydro-5,5,7,7-tetramethyl-6-oxoindeno[5,6-d]imidazol-2-yl)pyridinium chloride;

2-[[(p-fluorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[(2-carboxyethyl)dithio]methyl]-4-methoxy-3-methyl-1-(1,5,6,7-tetrahydro-5,5,7,7-tetramethyl-6-oxoindeno.5,6-d]imidazol-2-yl)pyridinium chloride;

2-[[(1-carboxyethyl)dithio]methyl]-4-methoxy-3-methyl-1-(1,5,6,7-tetrahydro-5,5,7,7-tetramethyl-6-oxoindeno[5,6-d]imidaZol-2-yl)pyridinium chloride;

2-[[(p-chlorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[(hexyldithio)methyl]-4-methoxy-3-methyl-1-(1,5,6,7-tetrahydro-5,5,7,7-tetramethyl-6-oxoindeno[5,6-d]imidazol-2-yl)pyridinium chloride;

intramolecularly deprotonized 2-[(3-furfuryldithio)methyl]-4-methoxy-3-methyl-1-(1,5,6,7-tetrahydro-5,5,7,7-tetramethyl-6-oxoindeno[5,6-d]imidazol-2-yl)pyridinium cation;

4-methoxy-3-methyl-2-[(pentyldithio)methyl]-1-(1,5,6,7-tetrahydro-5,5,7,7-tetramethyl-6-oxoindeno[5,6-d]imidazol-2-yl)pyridinium chloride;

2-[[(2-chloroallyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

4-methoxy-3-methyl-2-[[(o-nitrobenzyl)dithio]methyl]-1-(1,5,6,7-tetrahydro-5,5,7,7-tetramethyl-6-oxoindeno[5,6-d]imidazol-2-yl)pyridinium chloride;

2-[[(3,4-dichlorophenyl)dithio]methyl]-4-methoxy-3-methyl-1-(1,5,6,7-tetrahydro-5,5,7,7-tetramethyl-6-oxo-indeno[5,6-d]imidazol-2-yl)pyridinium chloride;

2-[[(p-methoxyphenyl)dithio]methyl]-4-methoxy-3-methyl-1-(1,5 6,7-tetrahydro-5,5,7,7-tetramethyl-6-oxoindeno[5,6-d]imidazol-2-yl)pyridinium chloride;

4-methoxy-3-methyl-2-[[(5-nitro-2-benzimidazolyl)dithio]methyl]-1-(1,5,6,7-tetrahydro-5,5,7,7-tetramethyl-6-oxoindeno[5,6-d]imidazol-2-yl)pyridinium chloride;

2-[[[1-[(carboxymethyl)carbamoyl]ethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride; and 2-[[(o-chlorophenyl)dithio]methyl]-4-methoxy-3,5-dimethyl-1-(1,5,6,7-tetrahydro-5,5,7,7-tetramethyl-6-oxo-indeno[5,6-d]imidazol-2-yl)pyridinium chloride.

The compounds of formula I can be manufactured in accordance with the invention by (a) reacting a compound of the formula

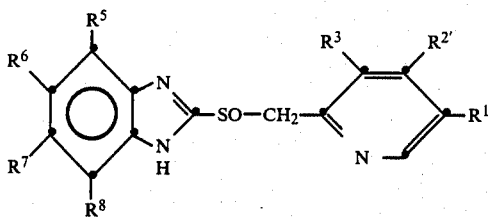

wherein
R$^1$, R$^3$, R$^5$, R$^6$, R$^7$ and R$^8$ are as described above and R$^{2'}$ is hydrogen, (C$_1$–C$_7$)-alkyl or (C$_1$–C$_7$)-alkoxy,
in the presence of acid with a compound of the formula

HS—R$^9$    III wherein R$^9$ is as described above,
or with SO$_2$ or with an alkali metal thiosulphate; or (b) cleaving the (C$_1$–C$_7$)-alkoxy group denoted by R$^2$ in a compound of formula I described above wherein R$^2$ is (C$_1$–C$_7$)-alkoxy or replacing this group by another (C$_1$–C$_7$)-alkoxy group; or (c) converting the carboxyl group(s) in a compound of formula I described above in which A is —SR$^9$ and R$^9$ contains one or more carboxyl group(s) into one or more (C$_1$–C$_7$)-alkoxycarbonyl group(s); or (d) hydrolyzing the (C$_1$–C$_7$)-alkoxycarbonyl group(s) in a compound of formula I wherein A is —SR$^9$ and R$^9$ contains one or more (C$_1$–C$_7$)-alkoxycarbonyl group(s) to one or more carboxyl group(s);
whereupon the compound obtained is isolated as a salt or internal salt and, if desired, a basic compound of formula I is converted into a pharmaceutically acceptable acid addition salt.

The reaction in accordance with the invention of the compounds of formulae II and III is conveniently effected in dilute aqueous hydrochloric acid, optionally with the addition of a suitable water-miscible organic solvent such as methanol, tetrahydrofuran, dimethoxyethane and the like, or in a solution of hydrogen chloride in a suitable organic solvent such as e.g. methanol, tetrahydrofuran, dimethoxyethane and the like. In place of hydrochloric acid or hydrogen chloride there can also be used other acids, for example dilute sulphuric acid, hydrobromic acid, phosphoric acid, trifluoroacetic acid, methanesulphonic acid and the like. The reaction is preferably effected at about room temperature, but it can also be carried out readily at temperatures below or above room temperature, conveniently at temperatures between about 0° C. and about 60° C.

In the aforementioned reaction of the compounds of formulae II and III in the presence of acid there are obtained corresponding compounds of formula I in which A is SR$^9$. The reaction of omeprazole (formula II; R$^1$ and R$^3$=CH$_3$; R$^{2'}$ and R$^6$=OCH$_3$; R$^5$, R$^7$ and R$^8$=H) and of timoprazole (formula II: R$^1$, R$^{2'}$, R$^3$, R$^5$, R$^6$, R$^7$ and R$^8$=H) with β-mercaptoethanol, ethyl mercaptan and benzyl mercaptan in the presence of hydrochloric acid is described in J. Biol. Chem. 260, 4591–4597 (1985).

Gaseous SO$_2$ can be used for the reaction in accordance with the invention of the compounds of formula II with SO$_2$. Conveniently, however, the SO$_2$ is produced in situ, for example from thionyl chloride or from a suitable salt of sulphurous acid such as sodium sulphite or sodium hydrogen sulphite. For example, the reaction can be carried out by taking water, then adding thereto thionyl chloride and subsequently a compound of formula II, whereupon the reaction mixture is warmed slightly for a short time (about 10 minutes). The reaction of compounds of formula II with SO$_2$ yields corresponding compounds of formula I in which A is —SO$_3$$^-$.

The reaction in accordance with the invention of a compound of formula II with an alkali metal thiosulphate is effected in aqueous acid, for example in dilute aqueous hydrochloric acid, whereby sodium thiosulphate pentahydrate can be used, for example, as the alkali metal thiosulphate. In place of hydrochloric acid there can also be used another acid, for example hydrobromic acid, dilute sulphuric acid, phosphoric acid, trifluoroacetic acid, methanesulphonic acid and the like. In place of sodium thiosulphate pentahydrate there can also be used another suitable alkali metal thiosulphate, for example potassium thiosulphate. The reaction is conveniently effected at room temperature, but it can also be carried out at temperatures above and below room temperature, for example at 0° C. to 60° C. The reaction in accordance with the invention of compounds of formula II With an alkali metal thiosulphate yields corresponding compounds of formula I in which A is —S—SO$_3$$^-$.

In compounds of formula I in which R$^2$ is (C$_1$–C$_7$)-alkoxy, the (C$_1$–C$_7$)-alkoxy group denoted by R$^2$ can in accordance with the invention be cleaved or replaced by another (C$_1$–C$_7$)-alkoxy group. The cleavage of the alkoxy group is effected, for example, by prolonged heating with aqueous hydrochloric acid, the temperature being about 40° C. to 90° C. and the reaction time being 1 hour to 2 weeks. In place of hydrochloric acid there can, however. also be used other suitable acids, for example methanesulphonic acid and the like. In this manner there are obtained compounds of formula I in which R$^2$ is a negatively charged oxygen atom, which can also be viewed as pyridone derivatives with the partial structure of formula Ia given above.

The replacement in accordance with the invention of a (C$_1$–C$_7$)-alkoxy group denoted by R$^2$ by another (C$_1$–C$_7$)-alkoxy group can be achieved by prolonged standing in the (C$_1$–C$_7$)-alkanol corresponding to the desired (C$_1$–C$_7$)-alkoxy group, which can be effected at room temperature, whereby, however, temperatures above and below room temperature can also be used, for example temperatures of about 0° C. to about 60° C. The reaction time amounts to 24 hours to 1 month depending on the temperature; when the reaction is carried out at room temperature, then a reaction time of about 1 to about 4 weeks, conveniently about 2 weeks, is indicated.

The esterification in accordance with the invention of a compound of formula I in which A is —SR$^9$ and R$^9$ contains one or more carboxyl group(s) can be effected, for example, by firstly preparing a corresponding reactive carboxylic acid derivative (e.g. a corresponding acid chloride or the like, which can be accomplished by means of thionyl chloride or the like, and then converting this derivative into the corresponding ester by treatment with the corresponding alcohol. The esterification can, however, also take place on the occasion of the reaction of a compound of formula II with a compound of formula III in which R$^9$ contains one or more carboxyl group(s), namely when the reaction is carried out in the presence of acid dissolved in the corresponding alcohol in the absence of water. If, for example, a compound of formula II is reacted with thiomalic acid in the presence of ethanolic hydrochloric acid, then there is obtained a corresponding compound of formula I in which A is —$SR^9$ and $R^9$ is 1,2-bis-(ethoxycarbonyl)ethyl, The hydrolysis in accordance with the invention of a compound of formula I in which A is —$SR^9$ and $R^9$ contains one or more ($C_1$-$C_7$)-alkoxycarbonyl group(s) can be effected, for example, under acidic conditions, e.g. by means of aqueous hydrochloric acid. This ester hydrolysis can also be effected on the occasion of the reaction of the compound of formula II with a compound of formula III, namely when $R^9$ in formula III contains one or more ($C_1$-$C_7$)—alkoxycarbonyl group(s) and the reaction is carried out in the presence of aqueous acid. If, for example, a compound of formula II is reacted with ethyl thioglycolate in the presence of aqueous hydrochloric acid, then there can be obtained a corresponding compound of formula I in which A is —$SR^9$ and $R^9$ is carboxymethyl, Depending on the nature of the starting materials and on the reaction conditions which are used the products obtained can be isolated as salts or as internal salts. If desired, basically substituted products can be converted into pharmaceutically acceptable acid addition salts, for example with hydrogen chloride, hydrogen bromide, phosphoric acid, sulphuric acid, citric acid, p-toluenesulphonic acid and the like.

The starting materials of formula II are known or can be prepared readily according to methods which ar known per se and which are familiar to any person skilled in the art; moreover, some of the Examples hereinafter contain detailed information concerning the preparation of certain compounds of formula II.

Compounds of formula III are known or can be prepared according to known methods.

As mentioned earlier, the (benzimidazol-2-yl)-pyridinium compounds of formula I have valuable pharmacodynamic properties.

Representative compounds of formula I were investigated with respect to their anti-ulcer activity, to their gastric acid secretion-inhibiting activity as well as to their toxicity The experimental procedure described hereinafter was used to determine the anti-ulcer activity:

Groups each comprising 8 male rats with a body weight of 130-150 g are used for each dosage of a test substance. Before the beginning of the experiment the animals receive no food for 24 hours, but receive water ad libitum. Various dosages of the substances to be tested (suspended in 0.5% tragacanth) or the vehicle alone (controls) are administered twice perorally, namely 1 hour before and 2 hours after the peroral administration of 20 mg/kg of indomethacin. In the control animals this dosage of indomethacin leads to lesions of the stomach within 5 hours. The animals are killed 6 hours after the first administration of the substanoe under investigation (or of the vehicle alone). The rats which remain protected from the occurrence of macroscopically visible lesions to the mucous membrane of the stomach are counted. The $ED_{50}$ is that dosage of a test substance at which 50% of the animals are protected from the occurence of such lesions.

The experimental procedure described hereinafter was used to determine the gastric acid secretion-inhibiting activity:

A part of the stomach fundus of female and male beagle hounds is separated from the remainder of the stomach in the form a pouch of the Heidenhain type (modification of the method described by Rudick et al. in J. Surgical Research 7,383-398 (1967)). In the pouch there is fitted a steel cannula which is conducted externally through the abdominal wall. Before each experiment the animals receive no food for 18 hours, but receive water ad libitum. They are conscious and standing during the experiment and their gastric acid secretion is stimulated by the intravenous infusion of 4-methylhistamine, a selective agonist of the histamine $H_2$-receptors. The gastric acid production is determined in 15 minute fractions of the stomach pouch juioe. As soon as the gastric acid production has a constant value, the substances to be tested are administered orally as a dry powder filled into gelatine capsules. The $ED_{50}$ is that dosage of a test substance which brings about a 50% inhibition of the gastric acid production caused by 4-methylhistamine in the treated animals in comparision to the controls.

In the following Table there are given for a series of representative compounds of formula I the results of the testing with respect to their anti-ulcer activity and to their gastric secretion-inhibiting activity. Moreover, this Table contains data concerning the acute toxicity ($LD_{50}$ in the case of single oral administration to mice).

| Compound | Anti-ulcer, $ED_{50}$ mg/kg p.o. | Gastric acid secretion-inhibition, $ED_{50}$ mg/kg p.o. | Toxicity, LD 50 mg/kg p.o. |
|---|---|---|---|
| A | 1.2 | 1.5 | >5000 |
| B | 2.5 | 2.8 | 1250-2500 |
| C | 3.0 | 3.0 | 1250-2500 |
| D | 1.9 | 6.8 | >5000 |
| E | 2.1 | 6.0 | >5000 |
| F | 1.7 | 1.6 | 1250-2500 |
| G | 2.3 | 1.5 | 312-625 |
| H | 1.8 | 6.2 | 1250-2500 |
| I | 2.3 | 3.9 | 312-625 |
| J | 2.4 | 2.2 | 1250-2500 |
| K | 2.3 | 6.5 | 312-625 |
| L | 1.6 | 3.4 | 312-625 |
| M | 1.6 | 4.6 | 312-625 |
| N | 1.5 | 3.7 | 312-625 |
| O | 2.3 | 2.9 | 312-625 |
| P | 1.9 | 4.1 | 312-625 |
| Q | 1.6 | 4.9 | 312-625 |

A=2-[(propyldithio)methyl]-4-methoxy-3-methyl-1-[5-(trifluoromethyl)-2-benzimidazolyl]pyridinium chloride B=2-[[[(R)-2-Amino-2-carboxyethyl]dithio]methyl]-4-methoxy-3-methyl-1-[5-(trifluoromethyl)-2-benzimidazolyl]pyridinium chloride C=2-[[[(R)-2-[(S)-4-Amino-4-carboxybutyramido]-2-[(carboxymethyl)carbamoyl]ethyl]dithio]methyl]-4-methoxy-3-methyl-1-[(5-trifluoromethyl)-2-benzimidazolyl]pyridinium chloride D=2-[(Hexyldithio)methyl]-4-methoxy-3-methyl-1-[5-(trifluoromethyl) -2-benzimidazolyl]pyridinium chloride E=2-[[(o-Chlorophenyl)dithio]methyl]-4-methoxy-3-methyl-1-[5-(trifluoromethyl)-2-benzimidazolyl]-pyridinium chloride F=2-[(Ethyldithio)methyl]-4-methoxy-3-methyl-1-[5-(trifluoromethyl)-2-benzimidazolyl]pyridinium chloride G=2-[[(2-Aminoethyl)dithio]methyl]-4-methoxy-3-methyl-b 1-[5-(trifluoromethyl)-2-benzimidazolyl]-pyridinium chloride H=2-[[(m-Chlorophenyl)dithio]methyl]-4-methoxy-3-methyl-1-(1,5,6,7-tetrahydro-5,5,7,7-tetramethyl-6-oxoindeno[5,6d]imidazol-2-yl)pyridinium chloride I=2-[[[(R)-2-Amino-2-carboxyethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride J=2-[[[1,2-Bis-(ethoxycarbonyl)ethyl]dithio]methyl]-4-methoxy-3-methyl-1-[5-(trifluoromethyl)-2-benzimidazolyl]pyridinium chloride K=2-[(Ethyldithio)methyl]-4-methoxy-3-methyl-1-(1,5,6,7-tetrahydro-5,5,7,7-tetramethyl-6-oxoindeno[5,6-d]-imidazol-2-yl)pyridinium chloride L=4-Methoxy-3-methyl-2-[(propyldithio)methyl]-1-(1,5,6,7-tetrahydro-5,5,7,7-tetramethyl-6-oxoindeno[5,6-d]-imidazol-2-yl)pyridinium chloride M=2-[[[(R)-2-Amino-2-(ethoxycarbonyl)ethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride N=Intramolecularly deprotonized 3-[[[2-(dimethylaminoethyl]dithio]methyl]-4-methoxy-3-methyl-1-(1,5,6,7-tetrahydro-5,5,7,7-tetramethyl-6-oxoindeno[5,6-d]imidazol-2-yl)pyridinium cation O=2-[[(2-Hydroxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride P=2-[[[(RS)-3-Amino-3-carboxypropyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride Q=2-[(Cyclopentyldithio)methyl]-4-methoxy-3-methyl-1-(1,5,6,7-tetrahydro-5,5,7,7-tetramethyl-6-oxoindeno[5,6-d]imidazol-2-yl)pyridinium chloride.

The compounds and salts defined earlier can be used as medicaments, e.g. in the form of pharmaceutical preparations. Oral administration in the form of solid pharmaceutical preparations such as tablets, coated tablets, dragees, hard gelatine capsules and soft gelatine capsules is preferred. There can also be oral administration in the form of liquid pharmaceutical preparations such as solutions, emulsions and suspensions, rectal administration, e.g. in the form of suppositories, or parenteral administration, e.g. in the form of injection solutions.

Medicaments containing one of the compounds and salts defined earlier are likewise an object of the present invention. The manufacture of such medicaments can be effected by bringing one or more of the compounds and salts defined earlier and, if desired, one or more other therapeutically active substances into a galenical administration form together with one or more therapeutically inert excipients.

For the manufacture of tablets coated tablets, dragees and hard gelatine capsules the compounds and salts defined earlier can be processed with pharmaceutically inert inorganic or organic excipients. As such excipients there can be used e.g. for tablets, dragees and hard gelatine capsules lactose, maize starch or derivatives thereof, talc, stearic acid or its salts or other conventional excipients. For the manufacture of pharmaceutical preparations which are resistant to gastric juice it is necessary to apply a gastric juice-resistant coating which can consist e.g. of hydroxypropylmethylcellulose phthalate.

For soft gelatine capsules there are suitable as excipients e.g. vegetable oils, waxes, fats, semi-solid and liquid polyols and the like.

For the manufacture of solutions and syrups there are suitable as excipients e.g. water, polyols, saccharose, invert sugar, glucose and the like.

For suppositories there are suitable as excipients e.g. natural or hardened oils, waxes, fats, semi-liquid or liquid polyols and the like.

For injection solutions there are suitable as excipients e.g. water, alcohols, polyols, glycerine, vegetable oils and other conventional excipients.

The pharmaceutical preparations can contain, in addition, preserving agents, solubilizers, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

In accordance with the invention the compounds and salts decribed earlier can be used in the control or prevention of illnesses, for example in the control or prevention of gastric ulcers and duodenal ulcers by the administration of effective amounts thereof to warmblooded animals in need of such treatment. The dosage for humans can vary within wide limits and, of course, will be fitted to the individual requirements in each particular case. For humans, in general, in the case of oral administration a daily dosage of about 30–400 mg should be appropriate and in the case of intravenous administration a daily dosage of about 1–50 mg should be appropriate.

The use of the compounds and salts defined earlier for the manufacture of medicaments for the control or prevention of gastric ulcers and duodenal ulcers is also an object of the invention.

In the following Examples, which illustrate the present invention but which are not intended to limit its extent in any manner, all temperatures are given in degrees Celsius.

EXAMPLE 1

(a) A solution of 24 g (0.22 mol) of 2,3-dimethylpyridine in 100 ml of methylene chloride is treated while cooling with ice with a solution of 46.6 g (0.27 mol) of m-chloroperbenzoic acid in 100 ml of methylene chloride. The reaction mixture is heated under reflux for 2 hours and concentrated in a rotary evaporator. The residue is chromatographed on silica gel with ethyl acetate/methylene chloride (3:1) as the elution agent, the medium pressure flash chromatography method being used and the pressure being produced with nitrogen gas. By recrystallization from ether there is obtained 2,3-dimethylpyridine 1-oxide of melting point 56°.

(b) A solution of 15 g (0.12 mol) of 2,3-dimethylpyridine 1-oxide in 75 ml of chloroform is boiled at reflux and treated as rapidly as possible with 37 ml of trichloroacetyl chloride (it is advantageous to add the acid chloride through the reflux condenser). The reaction mixture is heated under reflux for 2.5 hours, subsequently poured into a mixture of ice and sodium bicarbonate and the resulting solution is washed several times with methylene chloride. The organic phase is dried with sodium sulphate, filtered and concentrated. The residue is chromatographed on silica gel with methylene chloride, the medium pressure flash chromatography method being used and the pressure being produced with nitrogen gas. The 2-chloromethyl-3-methylpyridine obtained is processed directly.

(c) A solution of 24 g (0.17 mol) of 2-chloromethyl-3-methylpyridine in 200 ml of methylene chloride is treated while cooling with ice with a solution of 44 g (0.25 mol) of m-chloroperbenzoic acid in 200 ml of methylene chloride. The reaction mixture is heated under reflux for 2 hours and concentrated in a rotary evaporator. The residue is chromatographed on silica gel with ethyl acetate/methylene chloride (3:1) as the elution agent, the medium pressure flash chromatography method being used and the pressure being produced with nitrogen gas. The 2-chloromethyl-3-methylpyridine 1-oxide obtained is processed directly.

(d) 300 ml of concentrated sulphuric acid are added slowly while cooling with dry ice to 230 ml of concentrated nitric acid (68%; d=1.41), whereby the temperature of the mixture does not exceed 5°. A solution of 38.7 g (0.25 mol) of 2-chloromethyl-3-methylpyridine 1-oxide is added thereto and the mixture is stirred at 80° for 2 hours. The reaction mixture is poured on to a mixture of ice and methylene chloride, the aqueous phase is washed several times with methylene chloride and the methylene chloride solution is extracted with 10% sodium bicarbonate solution. The organic phase is dried with sodium sulphate and concentrated. The residue is recrystallized from ethyl acetate, there being obtained 2-chloromethyl-3-methyl-4-nitropyridine 1-oxide. The product exhibits a melting point of 126°-129°.

(e) A solution of 4.5 g (0.024 mol) of 2-chloromethyl-3-methyl-4-nitropyridine 1-oxide in 25 ml of methylene chloride and 25 ml of acetonitrile is treated with 5 ml of phosphorus trichloride and the mixture is stirred at room temperature for 20 minutes. The reaction mixture is poured on to a mixture of ice and 20 g of sodium carbonate and the resulting aqueous solution is washed several times with methylene chloride. The organic phase is dried and evaporated. The thus-obtained 2-chloromethyl-3-methyl-4-nitropyridine is processed directly.

(f) A solution of 11,5 g (0.062 mol) of 2-chloromethyl-3 -methyl-4-nitropyridine and 16 g (0.06 mol) of 5,7-dihydro-2-mercapto-5,5,7,7-tetramethylindeno[5,6-d]-imidazol-6(1H)-one in 200 ml of abs. acetone is treated with 13 g of finely ground potassium carbonate and the mixture is stirred at room temperature under argon for 18 hours, 100 ml of acetone are distilled off in vacuo, whereupon the residue is poured on to ice. The product which crystallizes out is filtered off and dissolved in methylene chloride; the solution obtained is washed with water, dried and concentrated. By recrystallization from ethyl acetate/ether there is obtained 5,7-dihydro-5,5,7,7-tetramethyl-2 -[[(3-methyl-4-nitro-2 -pyridyl)methyl]thio]indeno[5,6-d]imidazol-6(1H)-one of melting point 181°-183° (decomposition).

(g) A solution of 4.4 g (0.011 mol) of 5,7-dihydro-5,5,7,7-tetramethyl-2-[[(3-methyl -4-nitro-2-pyridyl)methyl)thio]indeno[5,6-d]imidazol-6(1H)-one in 100 ml of abs. methanol is treated with 3 g of sodium methylate, whereupon the mixture is boiled at reflux for 18 hours under argon. After concentrating the reaction mixture in vacuo the residue is treated with methylene chloride, whereupon the mixture is buffered by means of glacial acetic acid; the methylene chloride phase is extracted several times with a sodium bicarbonate solution, dried and evaporated. By recrystallisation from ethyl acetate there is obtained 5,7-dihydro-2-[[(4-methoxy-3 -methyl-2-pyridyl)methyl]thio]-5,5,7,7-tetramethylindeno[5,6-d]imidazol-6(1H)-one of melting point 222°-226°.

(h) A solution of 6 g (0.015 mol) of 5,7-dihydro-2-[[(4-methoxy-3-methyl-2-pyridyl)methyl]thio]-5,5,7,7-tetramethylindeno[5,6-d]imidazol-6(1H)-one in 90 ml of abs. methylene chloride is treated under argon at −40° to −50° within 10 minutes with a solution of 3.3 g (0.019 mol) of m-chloroperbenzoic acid in 50 ml of abs. methylene chloride. The solution is subsequently stirred for an additional 20 minutes extracted with a 10% sodium carbonate solution, dried and evaporated with the continuous replacement of methylene chloride by ethyl acetate. There thereby crystallizes 5,7-dihydro-2-[[(4-methoxy-3-methyl-2-pyridyl)methyl]sulphinyl]-5,5,7,7 -tetramethylindeno[5,6-d]imidazol-6(1H)-one which melts at 192°-194° with decomposition.

(i) A solution of 0.73 ml of n-propyl mercaptan in 30 ml of 1N aqueous hydrochloric acid is treated with 3 g of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 4-methoxy-3-methyl-2 -[(propyldithio)methyl-1-(1,5,6,7-tetrahydro -5,5,7,7-tetramethyl-6-oxoindeno[5,6-d]imidazol-2 -yl)-pyridinium chloride obtained exhibits a melting point of 235° (decomposition).

EXAMPLE 2

A solution of 1 g of methyl mercaptan in 40 ml of 1N aqueous hydrochloric acid is treated with 6 g of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 4-methoxy-3-methyl-2 -[(methyldithio)methyl-1-(1,5,6,7-tetrahydro -5,5,7,7-tetramethyl-6-oxoindeno[5,6-d]imidazol-2 -yl)pyridinium chloride obtained exhibits a melting point of 200° (decomposition).

EXAMPLE 3

A solution of 680 mg of ethyl mercaptan in 30 ml of 1N aqueous hydrochloric acid is treated with 4 g of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 2-[(ethyldithio)-methyl]-4-methoxy-3-methyl-1 -(1,5,6,7-tetrahydro-5,5,7,7 -tetramethylindeno5,6-d]imidazol-2-yl)pyridinium chloride obtained exhibits a melting point of 239° (decomposition).

EXAMPLE 4

A solution of 0.1 ml of isopropyl mercaptan in 20 ml of 0.1N aqueous hydrochloric acid is treated with 411 mg of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 2-[(isopropyldithio)methyl]-4-methoxy-3 -methyl-1-(1,5,6,7-tetrahydro-5,5,7,7-tetramethyl-6-oxoindeno[5,6-d]imidazol-2 -yl)-pyridinium chloride obtained exhibits a melting point of 150° (decomposition).

EXAMPLE 5

A solution of 1.2 g of sec.butyl mercaptan in 40 ml of 1N aqueous hydrochloric acid is treated with 5 g of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 2-[(sec-butyldithio)methyl]-4-methoxy-3 -methyl-1-(1,5,6,7-tetrahydro -5,5,7,7-tetramethyl-6-oxoindeno[5,6-d]imidazol-2 -yl)-pyridinium chloride obtained exhibits a melting point of 239° (decomposition).

EXAMPLE 6

A solution of 1.2 g of tert.butyl mercaptan in 40 ml of 1N aqueous hydrochloric acid is treated with 5 g of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 2-[(tert.-butyldithio)methyl]-4-methoxy-3 -methyl-1-(1,5,6,7-tetrahydro -5,5,7,7-tetramethyl-6-oxoindeno[5,6-d]imidazol-2 -yl)-pyridinium chloride obtained exhibits a melting point of 190° C. (decomposition).

EXAMPLE 7

A solution of 0.7 ml of pentanethiol in 20 ml of 1N aqueous hydrochloric and 20 ml of methanol is treated with 2 g of 5,7-dihydro-2-[[(4-methoxy-3-methyl-2 -pyridyl)methyl]sulphinyl]-5,5,7,7 -tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with a small amount of methanol and ether. The 4-methoxy-3-methyl-2-[(pentyldithio)methyl]-1 -(1,5,6,7-tetrahydro-5,5,7,7-tetramethyl-6 -oxoindeno[5,6-d]imidazol-2-yl)pyridinium chloride obtained exhibits a melting point of 160°-162° (decomposition).

EXAMPLE 8

A solution of 0.7 ml of hexanethiol in 20 ml of 1N aqueous hydrochloric acid and 80 ml of methanol is treated with 2 g of 5,7-dihydro-2-[[(4-methoxy-3-methyl-2-pyridyl) methyl]sulphinyl]-5,5,7,7 -tetramethylindeno5,6-d]imidaZol-6(1H)-one. A solution results. The reaction mixture is stirred at room temperature, a portion of the methanol is evaporated off and the mixture is then cooled briefly to about 5°, whereupon the crystalline product is filtered off and washed with cold water and ether. The 2-[(hexyldithio)methyl]-4 -methoxy-3-methyl-1-(1,5,6,7-tetrahydro -5,5,7,7-tetramethyl-6 -oxoindeno[5,6-d]imidazol-2-yl)pyridinium chloride obtained exhibits a melting point of 166°-167° (decomposition).

EXAMPLE 9

A solution of 1.1 g of dodecanethiol in 20 ml of 1N aqueous hydrochloric acid and 40 ml of methanol is treated with 2 g of 5,7-dihydro-2-[[(4-methoxy-3-methyl-2-pyridyl) methyl]sulphinyl]-5,5,7,7 -tetramethylindeno[5,6-d]imidazol-6(1H)-one. A solution results. The reaction mixture is stirred at room temperature, a portion of the methanol is evaporated off and the mixture is then cooled briefly to about 5°, whereupon the orystalline product is filtered off and washed with cold water and ether. The 2-[(dodecyldithio)methyl]-4-methoxy-3 -methyl-1-(1,5,6,7-tetrahydro-5,5,7,7 -tetramethyl-6-oxoindeno[5,6-d]imidazol-2 -yl)pyridinium chloride obtained exhibits a melting point of 145° (decomposition).

EXAMPLE 10

A solution of 2 ml of allyl mercaptan in 25 ml of 1N aqueous hydrochloric acid and 80 ml of methanol is treated with 4 g of 5,7-dihydro-2-[[(4-methoxy-3-methyl-2-pyridyl) methyl]sulphinyl]-5,5,7,7 -tetramethylindeno(5,6-d)imidazol-6(1H)-one. A solution results. The reaction mixture is stirred at room temperature, a portion of the methanol is evaporated off and the mixture is then cooled briefly to about 5°, whereupon the crystalline product is filtered off and washed with cold water and ether. The 2-[(allyldithio)methyl]-4 -methoxy-3-methyl-1-(1,5,6,7-tetrahydro -5,5,7,7-tetramethyl-6 -oxoinden[5,6-d]imidazol-2-yl)pyridinium chloride obtained exhibits a melting point of 180° (decomposition).

EXAMPLE 11

A solution of 490 mg of cyclopentanethiol in 20 ml of 1N aqueous hydrochloric acid and 20 ml of methanol is treated with 1.8 g of 5,7-dihydro-2-[[(4-methoxy-3-methyl-[2 -pyridyl)methyl]sulphinyl]-5,5,7,7 -tetramethylindeno[5,6-d]imidazol-6(1H)-one. A solution results. The reaction mixture is stirred at room temperature, a portion of the methanol is evaporated off and the mixture is then cooled briefly to about 5°, whereupon the crystalline product is filtered off and washed with cold water and ether. The 2-[(cyclopentyldithio)methyl]-4-methoxy-3-methyl-1-(1,5,6,7-tetrahydro-5,5,7,7 -tetramethyl-6-oxoindeno[5,6-d]imidazol-2-yl)pyridinium chloride obtained exhibits a melting point of 187° (decomposition).

EXAMPLE 12

A solution of 0.5 ml of 2-mercaptoethanol in 25 ml of 1N aqueous hydrochloric acid is treated with 2 g of 5,7-dihydro-2-[[(4-methoxy-3-methyl-2 -pyridyl)methyl]sulphinyl]-5,5,7,7 -tetramethylindeno[5,6-d]imidazol6(1H)-one. There immediately results a clear solution from which a solid then begins to crystallize out. The reaction mixture is stirred at room temperature for 1 hour and then cooled briefly to about 5°, whereupon the crystalline product is filtered off and washed with a small amount of water and ether. The 2-[[(2-hydroxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained exhibits a melting point of 148°-150° (decomposition).

EXAMPLE 13

A solution of 0.73 ml of methyl thioglycolate in 30 ml of 1N aqueous hydrochloric acid is treated with 3 g of 5,7-dihydro-2-[[(4-methoxy-3-methyl-2-pyridyl)methyl]sulphinyl]-5,5,7,7-tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 4-methoxy-2-[[[(methoxycarbonyl)methyl]dithio]methyl]-3-methyl-1-(1,5,6,7-tetrahydro-5,5,7,7-tetramethyl-6-oxoindeno[5,6-d]imidazol-2-yl)pyridinium chloride obtained exhibits a melting point of 162°–164° (decomposition).

EXAMPLE 14

A solution of 2 g of thiomalic acid in 50 ml of 1N aqueous hydrochloric acid is treated with 5 g 5,7-dihydro-2-[[(4-methoxy-3-methyl-2-pyridyl)methyl]sulphinyl]-5,5,7,7-tetramethylindeno[5,6-d]imidazol-6(1H)-one. There immediately results a clear solution from which a solid then begins to crystallize out. The reaction mixture is stirred at room temperature for 1 hour and then cooled briefly to about 5°, whereupon the crystalline product is filtered off and washed with a small amount of water and ether. The 2-[[(1,2-dicarboxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained exhibits a melting point of 183°–187° (decomposition).

EXAMPLE 15

A solution of 107 mg of thiopropionic acid in 10 ml of 1N aqueous hydrochloric acid is treated with 411 mg of 5,7-dihydro-2-[[(4-methoxy-3-methyl-2-pyridyl)methyl]sulphinyl]-5,5,7,7-tetramethylindeno[5,6-d]imidazol-6(1H)-one. There immediately results a clear solution from which a solid then begins to crystallize out. The reaction mixture is stirred at room temperature for a half hour and then cooled briefly to about 5°, whereupon the crystalline product is filtered off and washed with a small amount of water and ether. The 2-[[(2-carboxyethyl)dithio]methyl]-4-methoxy-3-methyl-1-(1,5,6,7-tetrahydro-5,5,7,7-tetramethyl-6-oxoindeno[5,6-d]imidazol-2-yl) pyridinium chloride obtained exhibits a melting point of 189°–190° (decomposition).

EXAMPLE 16

A solution of 0.57 g of thiolactic acid in 20 ml of 1N aqueous hydrochloric acid is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. There immediately results a clear solution from which a solid then begins to crystallize out. The reaction mixture is stirred at room temperature for 6 hours and then cooled briefly to about 5°, whereupon the crystalline product is filtered off and washed with cold water and ether. The 2-[[(1-carboxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained exhibits a melting point of 192° (decomposition).

EXAMPLE 17

A solution of 1.81 g of L-cysteine in 40 ml of 1N aqueous hydrochloric acid is treated with 6.1 g of 5,7-dihydro-2-[[(4-methoxy-3-methyl-2-pyridyl)methyl]sulphinyl]-5,5,7,7-tetramethylindeno[5,6-d]imidazol-6(1H)-one. A clear solution results immediately. The reaction mixture is stirred at 0–5° for a half hour and the solution is then concentrated. The residue is dissolved in methylene chloride and methanol, whereupon the solvent system is distilled off at normal pressure and continuously replaced by ethyl acetate. The crystalline product is chromatographed on Sephadex LH-20 with methylene chloride/methanol 1:1) and crystallized once more as described above. The thus-obtained 2-[[[(R)-2-amino-2-carboxyethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride exhibits a melting point of 170° (decomposition).

EXAMPLE 18

A solution of 0.97 g of ethyl L-cysteinate.HCl in 20 ml of 1N aqueous hydrochloric acid is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. A clear solution results immediately. The reaction mixture is stirred at room temperature for 1 hour and then concentrated. The residue is crystallized from methanol-ethyl acetate. The 2-[[[(R)-2-amino-2-(ethoxycarbonyl)ethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride dihydrochloride obtained exhibits a melting point of 184° (decomposition).

EXAMPLE 19

A solution of 0.74 g of D,L-homocysteine in 20 ml of 1N aqueous hydrochloric acid is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. A clear solution results immediately. The reaction mixture is stirred at room temperature for 1 hour and then concentrated. The residue is crystallized from methanol-ethyl acetate. The 2-[[[(RS)-3-amino-3-carboxypropyl))dithio]methyl]-4-methoxy-3-methyl-1-(1,5,6,7-tetrahydro-5,5,7,7-tetramethyl-6-oxoindeno[5,6-d]imidazol-2-yl)pyridinium chloride hydrochloride obtained exhibits a melting point of 200° (decomposition).

EXAMPLE 20

610 mg of thiophenol are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then concentrated by means of a water-jet pump until a precipitate begins to crystallize out. At this moment about 2 ml of ethyl acetate are added thereto and the reaction mixture is stirred further until crystallization is complete. The 4-methoxy-3-methyl-2-[(phenyldithio)methyl]-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 183° (decomposition).

EXAMPLE 21

A solution of 1.3 g of p-thiocresol is dissolved while heating in 30 ml of 1N aqueous hydrochloric acid and treated with 4 g of 5,7-dihydro-2-[[(4-methoxy-3-methyl-2-pyridyl)methyl]sulphinyl]-5,5,7,7-tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 4-methoxy-3-methyl-2-[[(4-methylphenyl)dithio]methyl]-1-(1,5,6,7-tetrahydro-5,5,7,7-tetramethyl-6-oxoindeno[5,6-d]imidazol-2-yl)pyridinium chloride obtained eXhibits a melting point of 174° (decomposition).

EXAMPLE 22

0.723 g of 3-chlorothiophenol are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then concentrated by means of a water-jet pump until a precipitate begins to crystallize out. At this moment about 20 ml of ethyl acetate are added thereto and the reaction mixture is stirred further until crystallization is complete. The 2-[[(m-chlorophenyl)dithio)methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 163°-165°. (decomposition).

EXAMPLE 23

A solution of 0.754 g of p-thiosalicylic acid in 195 ml of 1N aqueous hydrochloric acid is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 2-[[(o-carboxyphenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained exhibits a melting point of 190° (decomposition).

EXAMPLE 24

A solution of 1.3 g of p-fluorothiophenol in 30 ml of 1N aqueous hydrochloric acid and 100 ml of methanol is treated with 4.1 g of 5,7-dihydro-2-[[(4-methoxy-3-methyl-2-pyridyl)methyl]sulphinyl]-5,5,7,7-tetramethylindeno[5,6-d]imidazol-6(1H)-one. A clear solution results immediately. The solution is stirred under a water-jet vacuum, whereby the reaction product crystallizes. The reaction product is filtered off and washed with cold water. The 2-[[(p-fluorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained exhibits a melting point of 150° (decomposition).

EXAMPLE 25

0.8 g of p-chlorothiophenol is dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then concentrated by means of a water-jet pump until a precipitate begins to crystallize out. At this moment about 20 ml of ethyl acetate are added thereto and the reaction mixture is stirred further until crystallization is complete. The 2-[[(p-chlorophenyl)dithio)methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 170°-180° (decomposition).

EXAMPLE 26

0.7 g of 3-methoxythiophenol is dissolved in 20 ml of methanol and 2 ml of about 6N methanolic hydrochloric acid. The solution is treated with 2.05 g of 5,7-dihydro-2-[[(4-methoxy-3-methyl-2-pyridyl)methyl]sulphinyl]-5,5,7,7-tetramethylindeno[5,6-d]imidazol-6(1H)-one. stirred at room temperature and then concentrated by means of a water-jet pump until a precipitate begins to crystallize out. At this moment about 20 ml of ethyl acetate are added thereto and the reaction mixture is stirred further until crystallization is complete. The 4-methoxy-2-[[(m-methoxyphenyl)dithio)methyl]-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 158°-160° (decomposition).

EXAMPLE 27

0.8 g of pentafluorothiophenol is dissolved in 10 ml of methanol and 2 ml of about 6N methanolic hydrochloric acid. The solution is treated with 1.6 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then concentrated by means of a water-jet pump until a precipitate begins to crystallize out. At this moment about 20 ml of ether are added thereto and the reaction mixture is stirred further until crystallization is complete. The 4-methoxy-3-methyl-2-[[(pentafluorophenyl)dithio]methyl-1-(1,5,6,7-tetrahydro-5,5,7,7-tetramethyl-6-oxoindeno[5,6-d]imidazol-2-yl) pyridinium chloride obtained is filtered off and washed with cold ether; it exhibits a meltinq point of 153°-157° (decomposition).

EXAMPLE 28

0.6 ml of benzyl mercaptan is dissolved in 20 ml of methanol and 5 ml of about 6N methanolic hydrochloric acid. The solution is treated with 2.05 g of 5,7-dihydro-2-[[(4-methoxy-3-methyl-2-pyridyl)methyl]sulphinyl]-5,5,7,7-tetramethylindeno[5,6-d]imidazol-6(1H)-one. stirred at room temperature and then concentrated by means of a water-jet pump until a precipitate begins to crystallize out. At this moment about 20 ml of ether are added thereto and the reaction mixture is stirred further until crystallization is complete. The 2-[(benzyldithio)methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ether; it exhibits a melting point of 178°-180° (decomposition).

EXAMPLE 29

1.34 g ot triphenylmethyl mercaptan are dissolved in 30 ml of methanol and 20 ml of about 6N methanolic hydrochlorlc acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. stirred at room temperature and then concentrated by means of a water-jet pump until a precipitate begins to crystallize out. At this moment about 20 ml of water are added thereto and the reaction mixture is stirred further until crystallization is complete. The 4-methoxy-3-methyl-1 -(1,5,6,7-tetrahydro-5,5,7,7-tetramethyl-6 -oxoindeno[5,6-d]imidazol-2 -yl)-2-[(trityldithio)methyl]pyridinium chloride obtained is filtered off and washed with cold water; it exhibits a melting point of 170° (decomposition).

EXAMPLE 30

0.9 g of 2-mercaptopyridine is dissolved in 15 ml of about 6N methanolic hydrochloric acid. The solution is treated with 3 g of 5,7-dihydro-2-[[(4-methoxy-3-methyl-[2-pyridyl)methyl]sulphinyl]-5,5.7.7-tetramethylindeno[5.6-d]imidazol-6(1H )-one. stirred at room temperature and then concentrated by means of a water-jet pump until a precipitate begins to crystallize out. At this moment about 20 ml of ether are added thereto and the reaction mixture is stirred further until crystallization is complete. The 4-methoxy-3-methyl-2-(2-pyridydithiomethyl)-1-(1,5,6,7-tetrahydro-5,5,7,7-tetramethyl-6-oxoindeno[5.6-d]imidazol-2-yl)pyridinium chloride hydrochloride (1:1.5) obtained is filtered off and washed with cold methanol and ether; it exhibits a meltinq point of 151° (decomposition).

EXAMPLE 31

A solution of 0.9 9 of 2-mercaptopyrimidine in 30 ml of 1N aqueous hydrochloric acid is treated with 3 g of 5,7-dihydro-2-[[(4-methoxy-3 -methyl-2-pyridyl)methyl]-sulphinyl]-5,5,7,7 -tetramethylindeno[5,6-d]imidazol-6(1H )-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 2-[(2-pyrimidinyldithio)methyl]-4-methoxy-3 -methyl-1-(1,5,6,7-tetrahydro-5,5,7,7-tetramethyl-6 -oxoindeno[5,6-d]imidazol-2-yl)pyridinium chloride obtained exhibits a melting point of 173° (decomposition).

EXAMPLE 32

1.1 g of 2-amino-5-mercapto-1,3,4-thiadiazole are dissolved in 15 ml of about 6N methanolic hydrochloric acid. The solution is treated with 3 g of 5,7-dihydro-2-[[(4-methoxy-3 -methyl-2-pyridyl)methyl]sulphinyl]-5,5,7,7 -tetramethylindeno[5,6-d]imidazol-6(1H )-one. stirred at room temperature and then concentrated by means of a water-jet pump until crystallization is complete. The 2-[[5-amino-1,3,4-thiadiazol-2 -yl)dithio]methyl]-1-(1,5,6,7 -tetrahydro-5,5,7,7-tetramethyl-6 -oxoindeno[5,6-d]imidazol-2-yl)pyridinium chloride hydrochloride obtained is filtered off and washed with cold methanol; it exhibits a melting point of 161° (decomposition).

EXAMPLE 33

A solution of 0.8 g of 1,2,4-triazole-3-thiol in 30 ml of 1N aqueous hydrochloric acid is treated with 3 g of 5,7-dihydro-2-[[(4-methoxy-3 -methyl-2-pyridyl)methyl]sulphinyl]-5,5,7,7 -tetramethylindeno[5,6-d]imidazol-6(1H )-one. There immediately results a clear solution from which a solid then begins to crystallize out. The reaction mixture is stirred at room temperature for 4 hours and then cooled briefly to about 5°, whereupon the crystalline product is filtered off and washed with cold water and ether. The 4-methoxy-3 -methyl-1-(1,5,6,7-tetrahydro-5,5,7,7-tetramethyl-6 -oxoindeno[5,6-d]imidazol-2-yl) -2-[(1H -S -triazol-3-yldithio)methyl]pyridinium chloride obtained exhibits a melting point of 177° (decomposition).

EXAMPLE 34

0.876 g of furfuryl mercaptan is dissolved in 30 ml of about 6N methanolic hydrochloric acid. The solution is treated with 3 g of 5,7-dihydro-2-[[(4-methoxy-3 -methyl-2-pyridyl)methyl]sulphinyl]-5,5,7,7 -tetramethylindeno[5,6-d]imidazol-6(1H )-one. stirred at room temperature and then concentrated by means of a water-jet pump until a precipitate begins to crystallize out. At this moment about 20 ml of ethyl acetate are added thereto and the reaction mixture is stirred further until crystallization is complete. The 2-[(3-furfuryldithio)- methyl]-4-methoxy-3 -methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 174°–175° (decomposition).

EXAMPLE 35

851 mg of 6-mercaptopurine are dissolved in 100 ml of methanol and 50 ml of about 6N methanolic hydrochloric acid. The solution is treated with 2 g of 5,7-dihydro-2-[[(4-methoxy-3 -methyl-2-pyridyl)methyl]sulphinyl]-5,5,7,7 -tetramethylindeno[5,6-d]imidazol-6(1H )-one. stirred at room temperature and then concentrated by means of a water-jet pump until a precipitate begins to crystallize out. Ar this moment about 50 ml of ethyl acetate are added thereto and the reaction mixture is stirred further until crystallization is complete. The 4-methoxy-3-methyl-2 -[(purin-6-yldithio)methyl]-1-(1,5,6,7-tetrahydro -5,5,7,7-tetramethyl-6 -oxoindeno[5,6-d]imidazol-2-yl)pyridinium chloride hydrochloride obtained is filtered off and washed with cold ethyl acetate; it exhibits a melting point of 172° (decomposition).

EXAMPLE 36

A solution of 800 mg of 4,6-dimethyl-2-mercaptopyrimidine in 20 ml of 1N aqueous hydrochloric acid is treated with 2 g of 5,7-dihydro-2 -[[(4-methoxy-3 -methyl-2-pyridyl)methyl]sulphinyl]-5,5,7,7 -tetramethylindeno[5,6-d]imidazol-6(1H )-one. There immediately results a clear solution from which a solid then begins to crystallize out. The reaction mixture is stirred at room temperature for a half hour and then cooled briefly to about 5°, whereupon the crystalline product is filtered off and washed with cold water and ether. The 2-[[(4,6-dimethyl-2-pyrimidinyl)dithio]methyl]-4 -methoxy-3-methyl-1-(1,5,6,7-tetrahydro-5,5,7,7-tetramethyl-6 -oxoindeno[5,6-d]imidazol-2-yl)pyridinium chloride obtained exhibits a melting point of 170° (decomposition).

EXAMPLE 37

120 mg of furfuryl mercaptan are dissolved in 10 ml of methanol and 2 ml of about 6N methanolic hydrochloric acid. The solution is treated with 411 mg of 5,7-dihydro-2-[[(4-methoxy-3 -methyl-2-pyridyl)methyl]sulphinyl]-5,5,7,7 -tetramethylindeno[5,6-d]imidazol-6(1H )-one. stirred at room temperature and then concentrated by means of a water-jet pump until a precipitate begins to crystallize out. At this moment about 20 ml of ethyl acetate are added thereto and the reaction mixture is stirred further until crystallization is complete. The product obtained is filtered off. washed with cold ethyl acetate and dissolved in methylene chloride. whereupon the solution is extracted with 10% sodium bicarbonate solution. The organic solution is dried over sodium sulphate and concentrated. By crystallization of the residue from ethyl acetate there is obtained intramolecularly deprotonized 2-[(3-furfuryldithio)methyl]-4-methoxy-3-methyl-1-(1,5,6,7-tetrahydro-5,5,7,7 -tetramethyl-6-oxoindeno[5,6-d]imidazol-2-yl)pyridinium cation which exhibits a melting point of 155°-156° (decomposition).

EXAMPLE 38

150 mg of dlmethylaminoethanethiol hydrochloride are dissolved in 10 ml of methanol and 2 ml of about 6N methanolic hydrochloric acid. The solution is treated with 420 mg of 5,7-dihydro-2-[[(4-methoxy-3 -methyl-2-pyridyl)methyl]sulphinyl]-5,5,7,7 -tetramethylindeno[5,6-d]imidazol-6(1H )-one, stirred at room temperature and then concentrated by means of a water-jet pump until a precipitate begins to crystallize out. At this moment about 20 ml of ethyl acetate are added thereto and the reaction mixture is stirred further until crystallization is complete. The product obtained is filtered off, washed with cold ethyl acetate and taken up in a mixture of methylene chloride and 10% sodium bicarbonate solution. Extraction is carried out, the organic phase is dried over sodium sulphate and concentrated. By crystallization of the residue from ethyl acetate there is obtained intramolecularly deprotonized 2-[[[2-(dimethylamino)ethyl]dithio]methyl]-4 -methoxy-3-methyl-1-(1,5,6,7-tetrahydro-5,5,7,7 -tetramethyl-6 -oxindeno[5,6-d]imidazol-2-yl)pyridinium cation which exhibits a melting point of 146° (decomposition).

EXAMPLE 39

100 mg of 2-[(sec-butyldithio)methyl]-4 -methoxy-3-methyl-1-(1,5,6,7-tetrahydro-5,5,7,7 -tetramethyl-6-oxoindeno[5,6-d]imidazol-2-yl)pyridinium chloride are dissolved in 4 ml of 1N aqueous hydrochloric acid and heated at 110° (oil-bath temperature) for 24 hours. The reaction mixture is concentrated to dryness on a rotary evaporator, whereupon the residue is recrystallized twice from methylene chloride-ether. The 2-[(sec-butyldithio)methyl]-4-oxy-3 -methyl-1-(1,5,6,7 -tetrahydro-5,5,7,7-tetramethyl-6-oxoindeno[5,6-d]imidazol-2-yl)pyridinium obtained exhibits a melting point of 200° (decomposition).

EXAMPLE 40

40 ml of water are treated while cooling with ice with 5 ml of thionyl chloride and subsequently with 1.5 g of 2-[[(3,5-dimethyl-4 -methoxy-2-pyridyl)metbyl]sulphinyl]-5-methoxybenzimidazole. The reaction mixture is warmed slightly for 10 minutes and subsequently cooled with ice for 30 minutes, whereby a colourless precipitate crystallizes out. This precipitate is filtered off. washed with ice-cold water and dried. The intramolecularly deprotonized 4-methoxy-1-(5-methoxy-2 -benzimidazolyl)-3,5-dimethyl-2 -[(sulphothio)methyl]-pyridinium cation obtained exhibits a melting point 180°-183° (decomposition).

EXAMPLE 41

60 ml of water are treated while cooling with ice with 4 ml of thionyl chloride and subsequently with 2 g of 2-[[(4-methoxy-3-methyl-2 -pyridyl)methyl]sulphinyl]-5-(trifluoromethyl)benzimidazole. The reaction mixture is warmed slightly for 10 minutes and subsequently cooled wlth ice for 30 minutes. whereby a colourless precipitate crystallizes out. This precipitate is filtered off, washed With ice-cold water and dried. The intramolecularly deprotonized 4-methoxy-3-methyl-2 -[(sulphothio)methyl]-1-[5-(trifluoromethyl)-2-benzimidazolyl]pyridinium cation obtained exhibits a melting point 163°-164° (decomposition).

EXAMPLE 42

200 ml of water are treated while cooling with ice with 25 ml of thionyl chloride and subseguently with 10 g of 5,7-dihydro-2-[[(4-methoxy-3 -methyl-2-pyridyl)-methyl]sulphinyl]-5,5,7.7 -tetramethylindeno[5,6-d]imidazol-6(1H )-one. The reaction mixture is warmed slightly for 10 minutes and subsequently cooled with ice for 30 minutes, whereby a colourless precipitate crystallizes out. This precipitate is filtered off, washed with ice-cold water and dried. The intramolecularly deprotonized 4-methoxy-3-methyl-2 -[(sulphothio)methyl]-1-(1,5,6,7-tetrahydro-5,5,7,7 -tetramethyl-6-oxoindeno[5,6-d ]imidazol-2-yl)pyridinium cation obtained exhibits a melting point of 201°-203° (decomposition). By recrystallization from methylene chloride-methanol there is obtained a product of melting point 208°-209° (decomposition).

EXAMPLE 43

(a) A suspension of 5.2 g of 5.7-dihydro-2-mercapto-5,5,7,7 -tetramethylindeno[5,6-d]imidazol-6(1H )-one and 2.6 g of potassium t-butanolate is treated under argon with a solution of 3 g of 2-chloromethyl-3-methylpyridine in 30 ml of t-butanol and the mixture is stirred for 18 hours. After concentrating the mixture the residue is acidified with glacial acetic acid and dissolved in methylene chloride, whereupon 10% sodium bicarbonate solution is added thereto. The mixture is extracted and the methylene chloride solutlon is dried and concentrated. The thus-obtained crude product is chromatographed on silica gel and purified with methylene chloride/ethyl acetate (1:1), the medium pressure flash chromatography method being used and the pressure being produced with nitroqen gas. The 5,7-dihydro-5,5,7,7-tetramethyl-2-[[(3-methyl-2 -pyridyl)methyl]thio]indeno[5,6-d]imidazol-6(1H )-one which is obtained from ethyl acetate-n-hexane melts at 161°-164°.

(b) 2.5 g of 5,7-dihydro-5,5,7,7-tetramethyl-2-[[(3-methyl-2 -pyridyl)methyl]thio]indeno[5,6-d]imidazol-6(1H )-one are dissolved in 100 ml of chloroform and the solution is treated under argon with 1.5 g of m-chloroperbenzoic acid. whereupon the mixture is stirred for 15 minutes while cooling with ice. The solution is then poured into a mixture of sodium carbonate solution and ice. After repeated extraction the methylene chloride solution is dried and concentrated and the rasidue is crystallized from ether. The 5,7-dihydro-5,5,7,7-tetramethyl-2-[[(3-methyl-2 -pyridyl)methyl]sulphinyl]indeno[5,6-d]imidazol-6(1H )-one obtained exhibits a melting point of 176° (decomposition).

(c) 120 ml of water are treated while cooling with ice with 6.7 ml of thionyl chloride and subsequently with 2 g of 5,7-dihydro-5,5,7,7-tetramethyl-2-[[(3-methyl-2 -pyridyl)methyl]sulphinyl]indeno[5,6-d]imidazol-6(1H )-one. The reaction mixture is warmed slightly for 10 minutes and subsequently stirred at room temperature for 2 hours, whereby a colourless precipitate crystallizes out. This precipitate is filtered off, washed with ice-cold water and dried. The intramolecularly deprotonized 3-methyl-2-[(sulphothio)methyl]-1 -(1,5,6,7-tetrahydro-5,5,7,7-tetramethyl-6 -oxoindeno[5,6- d]imidazol-2-yl)pyridinium cation obtained exhibits a melting point of 194°–198° (decomposition).

EXAMPLE 44

(a) A solution of 183 mg (1.49 mmol) of 2,3-dimethylpyridine 1-oxide in 0.6 ml of conc. sulphuric acid is treated while coolіng with ice with 0.2 ml of 65% nitric acid (d=1.4). The reaction mixture is stirred at 9° for 24 hours and poured on to a mixture of ice and sodium carbonate, whereupon the resulting mixture is extracted with methylene chloride and the methylene chloride phase is dried and evaporated. The residue crystallized from ethanol/n-pentane, gives 2,3-dimethyl-4-nitropyridine 1-oxide of melting point 99°–102°.

(b) 25 g of 2,3-dimethyl-4-nitropyridine 1-oxide are dissolved in 1250 ml of n-propanol and the solution is stirred at 120° under argon for 16 days. The reaction mixture is concentrated, whereupon the residue is treated with methylene chloride-water and extracted. The organic phases are dried and concentrated. The residue is chromatographed on silica gel and purified with methylene chloride-methanol (20:1, 10:1), the medium pressure flash chromatography method being used and the pressure being produced with nitrogen gas. The 2,3-dimethyl-4-propoxypyridine 1-oxide obtained is processed directly.

(c) A solution of 23 ml of trichloroacetyl chloride in 50 ml of isopropyl acetate is added dropwise during 1 hour to a solution, boiling at reflux under argon, of 13 g of 2,3-dimethyl-4-propoxypyridine 1-oxide in 250 ml of isopropyl acetate. At the beginning the reaction exhibits a very exothermic character. During the addition of the first mol equivalent of trichloroacetyl chloride a vigorous evolution of carbon dioxide is observed. The solution is subsequently stirred under argon for a further 15 minutes at reflux temperature (oil-bath 130°), cooled to 10° with ice. treated with 100 ml of ether and stirred for 1 hour while cooling with ice. The crystalline precipitate which separates during the entire reaction is filtered off under suction and washed with ice-cold isopropyl acetate and ether. Crystalline reaction product can again be obtained from the mother liquor. The 2-chloromethyl-3-methyl-4-propoxypyridine hydrochloride obtained is processed directly.

(d) A solution of 11.5 g of 2-chloromethyl-3-methyl-4-propoxypyridine hydrochloride in 100 ml of methylene chloride is treated with 100 ml of 10% sodium carbonate solution. The aqueous solution is extracted three times with 100 ml of methylene chloride each time. The organic phase is dried over sodium sulphate. filtered and concentrated. The residue is dissolved in 180 ml of abs. acetone, treated with 10 g of 5 7-dihydro-2-mercapto-5,5,7,7 -tetramethylindeno[5,6-d]imidazol-6(1H )-one and with 18 g of qround potassium carbonate. The reaction mixture is stirred under argon for 18 hours. The solvent volume is concentrated to about 20 ml. The residual reaction mixture is poured on to ice-water and the whole is stirred vigorously for 20 minutes. After suction filtration and washing the reaction product the filter residue is dissolved in methylene chloride and washed with saturated sodium chloride solution. The organic phase is dried over sodium sulphate, filtered over Dicalite Speedex and concentrated. The product is chromatographed on a silica gel column with methylene chloride/ethyl acetate (1:1). The purified 5.7-dihydro-5,5,7,7 -tetramethyl-2-[[(3 -methyl-4-propoxy-2 -pyridyl)methyl]thio]indeno[5,6-d]imidazol-6(1H )-one melts at 162°–163°, crystallized from ether.

(e) 4.2 g of 5,7-dihydro-5,5,7,7-tetramethyl-2 -[[(3-methyl-4-propoxy-2 -pyridyl)methyl]thio]indeno[5,6-d]imidazol-6(1H )-one are dissolved in 50 ml of methylene chloride and treated at −40° under argon with 2.2 g of m-chloroperbenzoic acid in 15 ml of methylene chloride. The reaction mixture is stirred for 15 minutes. The solution is then poured into a mixture of sodium carbonate solution and ice. After repeated extraction the methylene chloride solution is dried and concentrated, and the residue is crystallized from ether. The 5,7-dihydro-5,5,7,7-tetramethyl-2-[[(3-methyl-4 -propoxy-2-pyridyl)methyl]sulphinyl]indeno[5,6-d]imidazol-6(1H )-one obtained exhibits a melting point of 171° (decomposition).

(f) 80 ml of water are treated while cooling with ice with 4 ml of thionyl chloride and subsequently with 2 of 5,7 -dihydro-5,5,7,7-tetramethyl-2-[[(3-methyl-4 -propoxy-2pyridyl)methyl]sulphinyl]indeno[5,6-d]imidazol-6(1H )one. The reaction mixture is warmed slightly for 10 minutes and subsequently cooled for 30 minutes with ice, whereby a precipitate crystallizes out. This precipitate is filtered off, washed with ice-cold water and dried. The intramolecularly deprotonized 3-methyl-4-propoxy-1-(1,5,6,7-tetrahydro-5,5,7,7 -tetramethyl-6-oxoindeno[5,6-d]imidazol-2-yl)-2 -[(sulphothio)methyl]pyridinium cation obtained is recrystallized from n-propanol and exhibits a melting point of 214° (decomposition).

EXAMPLE 45

(a) A mixture of 10.5 g of sodium ethylate 20 g of sodium carbonate and 400 ml of ethanol is stirred at 50° under argon for 30 minutes and then treated with 7 g (0.017 mol) of 5,7-dihydro-5,5,7,7-tetramethyl-2-[[(3-methyl-4-nitro-2-pyridyl)methyl]thio]indeno[5,6-d]imidazol-6(1H )-one. After stirring at 50° for 5 hours under argon the reaction mixture is concentrated in vacuo. The residue is treated with methylene chloride and buffered by means of glacial acetic acid; the methylene chloride solutіon is extracted with sodium bicarbonate solution, dried and concentrated. The residue is chromatographed on silica gel while eluting with methylene chloride/ethyl acetate (3:1). the medium pressure flash chromatography method being used and the pressure being produced with nitrogen gas. There is obtained 2-[[(4-ethoxy-3-methyl-2 -pyridyl)methyl)thio)-5.7-dihydro-5,5,7,7 -tetramethylindeno[5,6-d]imidazol-6 1H )-one which melts at 175°–176° after recrystallization from ether.

(b) A solution of 2 g (0.0049 mol) of 2-[[(4-ethoxy-3-methyl-2-pyridyl)methyl]thio]-5,7-dihydro-5,5,7,7-tetramethylindeno[5,6-d]imidazol-6(1H )-one in 35 ml of abs. methylene chloride is treated at −40° to −50° under argon within 10 minutes with 1.1 g (0.0064 mol) of m-chloroperbenzoic acid in 10 ml of abs. methylene chloride. The solution is subsequently stirred for an additional 20 minutes. extracted with 10% sodium carbonate solution, dried and concentrated with the continuous replacement of methylene chloride by ethyl acetate. There thereby crystallizes 2-[[(4-ethoxy-3-methyl-2 -pyridyl)methyl]sulphinyl]-5,7-dihydro -5,5,7,7-tetramethylindeno[5,6-d]imidazol-6(1H )-one which melts at 180° with decomposition.

(c) 80 ml of water are treated while cooling with ice with 4 ml of thionyl chloride and then with 2 g of 2-[[(4-ethoxy-3 -methyl-2-pyridyl)methyl]sulphinyl]-5,7-dihydro -5,5,7,7-tetramethylindeno[5,6-d]imidazol-6(1H )-one. The reaction mixture is warmed slightly for 10 minutes and subsequently cooled with ice for 30 minutes, whereby a colourless precipitate crystallizes out. This precipitate is filtered off, washed with ice-cold water and dried. The product is dissolved in methylene chloride, filtered and treated with ethanol. The solvent mixture is evaporated up to crystallization. The intramolecularly deprotonized 4-ethoxy-3-methyl-2 -[(sulphothio)methyl]-1-(1,5 6,7 -tetrahydro-5,5,7,7-tetramethyl-6 -oxoindeno[5,6-d]imidazol-2-yl)pyridinium cation obtained by filtration exhibits a melting point of 199°–204° (decomposition).

EXAMPLE 46

(a) A solution of 45 ml of 2,3-lutidine (2,3-dimethylpyridine) and 4.3 g of copper(I) iodide in 500 ml of tetrahydrofuran is cooled to −20° and treated under argon with 31 ml of ethyl chloroformate. The reaction mixture is heated to 30° and treated dropwise within 30 minutes with 125 ml of t-butylmagnesium chloride (2.6 molar, in tetrahydrofuran). Whereby the reaction temperature amounts to 40°–45°. The ethyl 4-tert-butyl-2,3-dimethyl-1(4H)-pyridinecarboxylate obtained as the intermediate can be isolated as follows: the reaction mixture is cooled to −10° and treated with 300 ml of aqueous (20%) ammonium chloride solution, whereupon 500 ml of ether are added and the organic solution is washed several times with a 20% ammonium chloride/ammonia (1:1) solution. 2N hydrochloric acid and 10% sodium carbonate solution. The organic phase is dried and concentrated, and the residue is purified on a silica gel column. whereby the medium pressure flash chromatography method (solvent: n-hexane/ether [20:1]) is used and the pressure is produced with nitrogen gas. The ethyl 4-tert-butyl-2,3-dimethyl-1(4H)-pyridinecarboxylate (2.1 g) obtained is processed directly by heating it at 170° for 1.5 hours with 420 mg of sublimed sulphur. The reaction mixture is dissolved in 200 ml of ether, whereupon the solution is extracted with 2N HCl and the aqueous solution is washed with ether, made alkaline with a 10% sodium carbonate solution and extracted with methylene chloride. The organic solution is dried and concentrated at normal pressure. The 4-tert-butyl-2,3-dimethylpyridine obtained is processed directly.

(b) A solution of 10.5 g of 4-tert-butyl-2,3-dimethylpyridine in 120 ml of methylene chloride is treated at room temperature with 14.4 g of m-chloroperbenzoic acid. The reaction mixture is made basic with a saturated sodium carbonate solution and extracted. The organic solution is dried and concentrated. The residue is purified on a silica gel column, whereby the medium pressure flash chromatography method (solvent: methylene chloride/ethyl acetate, with increasing ethyl acetate concentrations) is used and the pressure is produced with nitrogen gas. The 4-tert-butyl-2,3-dimethylpyridine N-oxide obtained is processed directly.

(c) A solution of 9.8 g of 4-tert-butyl-2,3-dimethylpyridine N-oxide in 120 ml of abs. chloroform is boiled at reflux under argon and treated through the condenser with 25.5 ml of trichloroacetyl chloride. After 22 hours the reaction mixture is poured on to ice, whereupon 10% sodium bicarbonate solution is added, the mixture is extracted with methylene chloride and the methylene chloride solution is dried and concentrated. The thus-obtained crude product is chromatographed on silica gel (solvent: methylene chloride/ether [10:1]). The 2-chloromethyl-4-tert-butyl-3-methylpyridine obtained is processed directly.

(d) A solution of 4.4 g of 2-chloromethyl-4-tert-butyl-3-methylpyridine in 150 ml of acetone is treated with 5.7 g of 5,7-dihydro-2-mercapto-5,5,7,7 -tetramethylindeno[5,6-d]imidazol-6(1H )-one and 5 g of ground potassium carbonate. The reaction mixture is stirred under argon for 18 hours, whereupon the solvent volume is concentrated to about 20 ml. The reaction mixture is treated with methylene chloride/water and extracted. The organic phase is dried and concentrated and the residue is crystallized from ether. The 2-[[(4-tert-butyl-3 -methyl-2-pyridyl)methyl]thio]-5,7-dihydro-5,5,7,7 -tetramethylindeno[5,6-d]imidazol-6(1H )-one obtained exhibits a melting point of 156°–158°.

(e) 1.1 g of crude 2-[[(4-tert-butyl-3-methyl-2 -pyridyl)methyl]thio]-5,7-dihydro-5,5,7,7 -tetramethylindeno[5,6-d]imidazol-6(1H )-one are dissolved in 20 ml of methylene chloride and the solution is treated slowly at −40° under argon with 600 mg of m-chloroperbenzoic acid in 5 ml of methylene chloride. The reaction mixture is stirred for 15 minutes. The solution is then poured into a mixture of sodium carbonate solution and ice. After repeated extraction the organic solution is dried and concentrated, and the residue is crystallized from ethyl acetate. The 2-[[(4-tert-butyl-3 -methyl-2-pyridyl)methyl]sulphinyl]-5,7 -dihydro-5,5,7,7-tetramethylindeno[5,6-d]imidazol-6(1H )-one obtained exhibits a melting point of 200°–204°(decomposition).

(f) 20 ml of water are treated while cooling with ice with 2 ml of thionyl chloride and with 900 mg of 2-[[(4-tert-butyl-3-methyl-2 -pyridyl)methyl]sulphinyl]-5,7-dihydro-5,5,7,7 -tetramethylindeno[5,6-d]imidazol-6(1H )-one. The reaction mixture is warmed slightly for 10 minutes and subsequently cooled with ice for 30 minutes, whereby a colourless precipitate crystallizes out. This precipitate is filtered off, washed with ice-cold water and dried. The intramolecularly deprotonized 4-tert-butyl-3-methyl-2-[(sulphothio)methyl]-1 -(1,5,6,7-tetrahydro-5,5.7,7-tetramethyl-6 -oxoindeno[5,6-d]imidazol-2-yl)pyridinium cation obtained exhibits a melting point of 209°–210° (decomposition).

EXAMPLE 47

(a) A solution of 6.75 g of 2,3-lutidine and 475 mg of copper(I) iodide in 150 ml of abs. tetrahydrofuran is cooled to −20° and treated under argon with 3.4 ml of ethyl chloroformate. The reaction mixture is heated to 30° and treated dropwise within 10 minutes with 14 ml of methylmagnesium chloride (3 molar, in tetrahydrofuran). The ethyl 2,3,4-trimethyl-1 (4H)-pyridinecarboxylate obtained as the intermediate can be isolated as follows: The reaction mixture is cooled to −10° and treated with 38 ml of aqueous (20%) ammonium chloride solution, whereupon 100 ml of ether are added and the organic solution is washed several times with a 20% ammonium chloride/ammonia (1:1) solution, 2N hydrochloric acid and 10% sodium carbonate solution. The organic solution is dried and concentrated, and the residue is purified on a silica gel column, the medium pressure flash chromatography method (solvent: n-hexane/ether [20:1]) being used and the pressure being produced with nitrogen gas.

The intermediate product (975 mg) obtained is processed directly by heating it at 140° for 1 hour with 160 mg of sublimed sulphur. The reaction mixture is dissolved in 100 ml of ether, whereupon the solution is extracted with 2N HCl and the aqueous solution is washed with ether, made alkaline with a 10% sodium carbonate solution and extracted with methylene chloride. The organic solution is dried and concentrated at normal pressure. The 2,3,4-trimethylpyridine obtained is processed directly.

(b) A solution of 14 g of 2,3,4-trimethylpyridine in 140 ml of methylene chloride is treated cautiously while cooling with ice with 21 g of m-chloroperbenzoic acid. The reaction mixture is boiled at reflux for 1 hour, then made basic with a saturated soda solution and subsequently extracted. The organic phase is dried and concentrated. The residue is purified on a silica gel column, the medium pressure flash chromatography method (solvent: methylene chloride/methanol [5:1]) being used and the pressure being produced with nitrogen gas. The 2,3,4-trimethylpyridine N-oxide obtained is processed directly.

(c) A solution of 13.3 g of 2,3,4-trimethylpyridine N-oxide in 130 ml of abs. chloroform is boiled at reflux under argon and treated through the condenser with 33.2 ml of trichloroacetyl chloride. After 18 hours the reaction mixture is poured on to ice, whereupon 10% sodium bicarbonate solution is added, the mixture is extracted with methylene chloride and the methylene chloride solution is dried and concentrated. The thus-obtained crude product is chromatographed on silica gel (solvent: methylene chloride/ether [5:1]). The 2-chloromethyl-3,4-dimethylpyridine obtained is processed directly.

(d) A solution of 4.5 g of 2-chloromethyl-3,4-dimethylpyridine in 80 ml of acetone is treated with 7.3 g of 5,7-dihydro-2-mercapto-5,5,7,7-tetramethylindeno[5,6-d]-imidazol-6(1H)-one and 5.4 g of ground potassium carbonate. The reaction mixture is stirred under argon for 18 hours, whereupon the solvent volume is concentrated to about 15 ml. The reaction mixture is poured on to ice-water; the solid is filtered off, washed with water and recrystallized from acetonitrile. The 2-[[(3,4-dimethyl-2-pyridyl)methyl]thio]-5,7-dihydro-5,5,7,7-tetramethylindeno[5,6-d]imidazol-6(1H)-one obtained exhibits a melting point of 163°-165°.

(e) 3.8 g of 2-[[(3,4-dimethyl-2-pyridyl)methyl]thio]5,7-dihydro-5,5,7,7-tetramethylindeno[5,6-d]imidazol-6(1H)-one are dissolved in 50 ml of abs. methylene chloride and the solution is treated slowly at −40° under argon with 2.2 g of m-chloroperbenzoic acid in 30 ml of methylene chloride. The reaction mixture is stirred for 20 minutes. The solution is then poured into a mixture of sodium carbonate solution and ice. After repeated extraction the organic solution is dried and concentrated, and the residue is crystallized from methylene chloride/ethyl acetate. The 2-[[3,4-dimethyl-2-pyridyl)methyl]sulphinyl]-5,7-dihydro-5,5,7,7-tetramethylindeno[5,6-d]imidazol-6(1H)-one obtained exhibits a melting point of 197°-200° (decomposition).

(f) 30 ml of water are treated while cooling with ice with 3 ml of thionyl chloride and subsequently with 1.5 g of 2-[[(3,4-dimethyl-2-pyridyl)methyl]sulphinyl]-5,7-di-hydro-5,5,7,7-tetramethylindeno[5,6-d]imidazol-6(1H)-one. The reaction mixture is warmed slightly for 10 minutes and subsequently cooled with ice for 30 minutes, whereby a colourless precipitate crystallizes out. This precipitate is filtered off, washed with ice-cold water and dried. The intramolecularly deprotonized 3,4-dimethyl-2-[(sulphothio)methyl]-1-(1,5,6,7-tetrahydro-5,5,7,7-tetramethyl-6-oxoindeno[5,6-d]imidazol-2-yl)pyridinium cation obtained exhibits a melting point of 156° (decomposition) after recrystallization from methylene chloride/methanol.

EXAMPLE 48

(a) A solution of 7.3 g (0.039 mol) of 2-chloromethyl-3-methyl-4-nitropyridine and 7.5 g (0.039 mol) of 5H-1,3-dioxolo[4,5-f]benzimidazole-6-thiol in 200 ml of abs. acetone is treated with 8 g of finely ground potassium carbonate, whereupon the mixture is stirred at room temperature under argon for 2 hours. The mixture is poured on to ice and the resulting crystals are filtered off, washed thoroughly with water and dissolved in acetonitrile. The solution obtained is filtered while hot. Upon cooling the filtrate there crystallizes 6-[[(3-methyl-4-nitro-2-pyridyl)methyl]thio]-5H-1,3-dioxolo[4,5-f]-benzimidazole of melting point 204°-205° (decomposition).

(b) A solution of 500 mg (1.45 mmol) of 6-[[(3-methyl-4-nitro-2-pyridyl)methyl]thio]-5H-1,3-dioxolo[4,5-f]-benzimidazole in 20 ml of abs. methanol is treated with 300 mg of sodium methylate, whereupon the mixture is boiled at reflux under argon for 18 hours. The reaction mixture is buffered by means of glacial acetic acid and concentrated in vacuo. The residue is treated with methylene chloride/sodium bicarbonate solution, whereupon the organic solution is dried and concentrated. By recrystallization from ethyl acetate there is obtained 6-[[(4-methoxy-3-methyl-2-pyridyl)methyl)-thio)-5H-1,3-dioxolo[4,5-f]benzimidazole of melting point 215°-220°.

(c) A solution of 330 mg (1 mmol) of 6-[[(4-methoxy-3-methyl-2-pyridyl)methyl]thio]-5H-1,3-dioxolo[4,5-f]-benzimidazole in 5 ml of chloroform is treated portionwise with 200 mg (1.2 mmol) of m-chloroperbenzoic acid While cooling with ice and stirring. After 15 minutes the reaction mixture is extracted with 10% sodium carbonate solution, dried and concentrated. The residue is chromatographed on silica gel with methylene chloride/methanol (8.5:1.5) as the elution agent, the medium pressure flash chromatography method being used and the pressure being produced with nitrogen. By recrystallization from ether there is obtained 6-[[(4-methoxy-3-methyl-2-pyridyl)methyl]sulphinyl]-5H-1,3-dioxolo[4,5-f]-benzimidazole of melting point 185°-186° (decomposition).

(d) 10 ml of water are treated while cooling with ice with 1 ml of thionyl chloride and subsequently with 500 mg of 6-[[(4-methoxy-3-methyl-2-pyridyl)methyl]sulphinyl]-5H-1,3-dioxolo[4,5-f]benzimidazole. The reaction mixture is diluted with 40 ml of water and subsequently cooled with ice for 30 minutes, whereby a colourless precipitate crystallizes out. This precipitate is filtered off, washed with ice-cold water and dried. The intramolecularly deprotonized 1-(5H-[1,3]dioxolo[4,5-f]-benzimidazol-6-yl)-4-methoxy-3-methyl-2-[(sulphothio)methyl]pyridinium cation obtained exhibits a melting point of 201° (decomposition).

EXAMPLE 49

(a) A solution of 2.5 g (0.015 mol) of 2,3-dimethyl-4-nitropyridine 1-oxide in 50 ml of abs. methanol is treated with 0.883 g of sodium methylate, whereupon the mixture is stirred at room temperature under argon for 2 days. The reaction mixture is concentrated and the residue is extracted with methylene chloride and saturated sodium chloride solution. The methylene chloride phase is dried and evaporated. The residue, crystallized from methylene chloride/ ether, gives 4-methoxy-2,3-dimethylpyridine 1-oxide of melting point 80°-83°.

(b) A solution of 500 mg (3.26 mmol) of 4-methoxy-2,3-dimethylpyridine 1-oxide in 20 ml of 1.2-dichloroethane is boiled at reflux and treated with 8.3 g of trichloroacetyl chloride. After 35 minutes the reaction mixture is poured on to ice, 10% sodium carbonate solution is added, the mixture is extracted with methylene chloride and the methylene chloride solution is dried and concentrated. The thus-obtained 2-chloromethyl-3-methyl-4-methoxypyridine is processed directly as the crude product.

(c) A solution of 4.5 g of 2-chloromethyl-4-methoxy-3-methylpyridine in 80% ml of acetone is treated with 7.3 g of 5,6,7,8-tetrahydro-5,5,8,8-tetramethyl-1H-naphth[2,3-d]imidazole-2-thiol and 5.4 g of ground potassium carbonate. The reaction mixture is stirred under argon for 18 hours, whereupon the solvent volume is concentrated to about 15 ml and poured on to ice-water. The solid is filtered off and washed with water. When recrystallized from methylene chloride/n-hexane the 5,6,7,8-tetrahydro-5,5,8,8-tetramethyl-2 -[[(4-methoxy-3-methyl-2-pyridyl)methyl]thio]-1H-naphth[2,3-d]]imidazole obtained exhibits a melting point of 170°.

(d) 3.1 g of 5 6,7,8-tetrahydro-5,5,8,8-tetramethyl-2-[[(4-methoxy-3 -methyl-2-pyridyl)methyl]thio]-1H-naphth[2.3-d]imidazole are dissolved in 40 ml of chloroform and treated while cooling with ice with 1.5 g of m-chloroperbenzoic acid, whereupon the mixture is stirred for 10 minutes and then poured into a mixture of sodium carbonate solution and ice. After repeated extraction the organic solution is dried and concentrated. The residue is chromatographed on silica gel (solvent: methylene chloride/methanol [20:1]). The 5,6,7,8-tetrahydro-5,5,8,8-tetramethyl-2-[[(4-methoxy-3 -methyl-2-pyridyl)methyl]sulphinyl]-1H -naphth[2,3-d]imidazole obtained is crystallized from ether and then exhibits a melting point of 167° (decomposition).

(e) 83 ml of water are treated while cooling with ice with 12.4 ml of thionyl chloride and with 4.8 g of 5,6,7,8-tetrahydro-5,5,8,8 -tetramethyl-2-[[(4-methoxy-3-methyl-2-pyridyl)methyl]sulphinyl]-1H -naphth[2,3-d]imidazole. The reaction mixture is treated with a small amount of methanol until complete solution occurs. Thereupon, the solution is warmed slightly for 10 minutes and stirred at room temperature for 2 hours, whereby a colourless precipitate crystallizes out. This precipitate is filtered off, washed with ice-cold water and dried. The intramolecularly deprotonized 4-methoxy-3-methyl-2-[(sulphothio)methyl]-1 -(5,6,7,8-tetrahydro-5,5,8,8 -tetramethyl-1H-naphth[2,3-d]imidazol-2-yl)pyridinium cation obtained exhibits a melting point of 206°-208° (decomposition).

EXAMPLE 50

A solution of 4.1 g of 5,7-dihydro-2-[[(4-methoxy-3-methyl-2 -pyridyl)methyl]sulphinyl]-5,5,7,7 -tetramethylindeno[5.6-d]imidazol-6(1H )-one in 300 ml of 1N aqueous hydrochloric acid is treated with an aqueous solution of 2.8 g of sodium thiosulphate pentahydrate. There immediately results a clear solution from which a solid then begins to crystallize out. The reaction mixture is stirred at room temperature and then cooled briefly to about 5°, whereupon the crystalline product is filtered off and washed with cold water and ether. The intramolecularly deprotonized 4-methoxy-3-methyl-2 -[sulphodithio)methyl]-1-(1,5,6,7-tetrahydro-5 5,7,7-tetramethyl- 6-oxoindeno[5,6-d]imidazol-2-yl)pyridinium cation obtained exhibits a melting point of 198°-199° (decomposition) after recrystallization from methanol.

EXAMPLE 51

A solution of 3.4 g of 2-[[(4-methoxy-3-methyl-2-pyridyl)methyl]sulphinyl]-5 -(trifluoromethyl)benzimidazole in 50 ml of 1N aqueous hydrochloric acid is treated with an aqueous solution of 2.5 g of sodium thiosulphate pentahydrate. There immediately results a clear solution from which a solid then begins to crystallize out. The reaction mixture is stirred at room temperature and then cooled briefly to about 5°, whereupon the crystalline product is filtered off and washed with cold water and ether. The reaction mixture is purified on a silica gel column, (solvent: methylene chloride/methanol [10:1]) and crystallized from ethyl acetate. The intramolecularly deprotonized [4-methoxy-3-methyl-2-[[(sulphodithio)methyl]-5 -(trifluoromethyl)-2-benzimidazolyl]pyridinium cation obtained exhibits a melting point of 186° (decomposition) after recrystallization from methanol.

EXAMPLE 52

A sOlution of 1.2 g of intramolecularly deprotonized 4-methoxy-1-(5-methoxy-2-benzimidazolyl)-3,5 -dimethyl-2-[(sulphothio)methyl]pyridinium cation in 20 ml of methylene chloride and 200 ml of ethanol is left to stand in an open flask for 2 weeks. The product mixture obtained is purified on a silica gel column (solvent: methylene chloride/methanol, 9:1). The purified intramolecularly deprotonized 4-ethoxy-1-(5-methoxy-2-benzimidazolyl)-3,5 -dimethyl-2-[(sulphothio)methyl]-pyridinium cation is crystallized from ethanol and then melts at 161°-168° (decomposition).

EXAMPLE 53

500 mg of 2-[[(o-carboxyphenyl)dithio]methyl]-4-methoxy-3-methyl-1 -(1,5,6,7-tetrahydro-5,5,7,7 -tetramethyl-6-oxoindeno[5.6-d]imidazol-2-yl)pyridinium chloride are stirred at room temperature with 0.5 ml of thionyl chloride, whereupon the reaction mixture is partially concentrated, treated with methanol and warmed slightly for 30 minutes. The crystallized-out material is filtered off under suction, washed with methanol and purified on silica gel with methylene chloride-methanol (10:1), the medium pressure flash chromatography method being used and the pressure being produced with nitrogen gas. The intramolecularly deprotonized 4-methoxy-2 -[[(o-methoxycarbonylphenyl)dithio]methyl]-3 -methyl-1-(1,5,6,7-tetrahydro-5 5,7,7-tetramethyl-6 -oxoindeno[5,6-d]imidazol-2-yl)pyridinium cation obtained exhibits a melting point of 132° (decomposition) after crystallization from ethyl acetate.

EXAMPLE 54

A solution of 700 mg of ethyl mercaptan in a mixture of 20 ml of 1N aqueous hydrochloric acid and 100 ml of water is treated at room temperature with 3.4 g of 2-[[(3,5-dimethyl-4-methoxy-2 -pyridyl)methyl]sulphinyl]-5-methoxybenzimidazole.

The solution is stirred for 30 minutes and extracted three times with methylene chloride; the organic solution is dried and concentrated. The residue is heated on a steam-bath and subsequently stirred at room temperature until a solid has crystallized out completely. The crystalline product is filtered off, washed with cold ethyl acetate and dried.

The 2-[(ethyldithio)methyl]-1 -(5-methoxy-2-benzimidazolyl)-3,5-dimethyl-4-oxy-pyridinium obtained exhibits a melting point of 190°–191°.

The 2-[(ethyldithio)methyl]-1 -(5-methoxy-2-benzimidazolyl)-3,5-dimethyl-4 -methoxy-pyridinium chloride which results as the intermediate is not isolated

EXAMPLE 55

850 mg of p-nitrothiophenol are dissolved in 20 ml of about 6N methanolic hydrochloric acid on a steam-bath. The solution is treated with 2 g of 5,7-dihydro-2-[[(4-methoxy-3-methyl-2 -pyridyl)methyl]sulphinyl]-5,5,7,7 -tetramethylindeno[5,6-d]imidazol-6(1H )-one and the mixture is concentrated by means of a water-jet pump until a precipitate crystallizes out. The 4-methoxy-3-methyl-2 -[[(p-nitrophenyl)dithio]methyl]-1 -(1,5,6,7-tetrahydro-5,5,7,7-tetramethyl-6 -oxoindeno[5,6-d]imidazol-2-yl)-pyridinium chloride obtained is filtered off and washed with cold methanol; it exhibits a melting point of 185° (decomposition).

EXAMPLE 56

A solution of 820 mg of D-penicillamine in 20 ml of 1N aqueous hydrochloric acid is treated with 2 g of 5,7-dihydro-2-[[(4-methoxy-3 -methyl-2-pyridyl)methyl]sulphinyl]-5,5,7,7 -tetramethylindeno[5,6-d]imidazol-6(1H )-one. There results a clear solution which is concentrated and treated with ethyl acetate. The reaction product crystallizes out, whereupon it is filtered off and washed with ethyl acetate. The 2-[[[(S)-2-amino-2 -carboxy-1,1-dimethylethyl]dithio]methyl]-4 -methoxy-3-methyl-1-(1,5,6,7-tetrahydro-5,5,7,7 -tetramethyl-6-oxoindeno[5,6-d]imidazol-2-yl)pyridinium chloride hydrochloride obtained exhibits a melting point of 183° (decomposition).

EXAMPLE 57

A solution of 307 mg of L-glutathione in 10 ml of 1N agueous hydrochloric acid is treated with 412 mg of 5,7-dihydro-2-[[(4-methoxy-3 -methyl-2-pyridyl)methyl]sulphinyl]-5,5,7,7 -tetramethylindeno[5,6-d]imidazol-6(1H )-one. There results a clear solution which is concentrated and treated with ethyl acetate. The reaction product crystallizes out, whereupon it is filtered off and washed with ethyl acetate. The 2-[[[(R)-2-[(S)-4-amino-4-carboxybutyramido]-2 -[(carboxymethylcarbamoyl)ethyl]dithio]methyl]-4 -methoxy-3-methyl-1-(1,5,6,7 -tetrahydro-5,5,7,7-tetramethyl-6 -oxoindeno[5,6-d]imidazol-2-yl)pyridinium chloride hydrochloride obtained exhibits a melting point of 202° (decomposition); $[\alpha]_D^{20} = -68.3°$ (methanol, 1%).

EXAMPLE 58

780 mg of 4-fluorobenzyl mercaptan are dissolved in 20 ml of about 6N methanolic hydrochloric acid. The solution is treated with 2 g of 5,7-dihydro-2-[[(4-methoxy-3 -methyl-2-pyridyl)methyl]sulphinyl]-5,5,7,7 -tetramethylindeno[5,6-d]imidazol-6(1H )-one, stirred at room temperature and then partially concentrated by means of a water-jet pump. About 20 ml of ethyl acetate are subsequently added thereto and the reaction mixture is stirred further until crystallization is complete. The 2-[[p-fluorobenzyl)dithio]methyl]-4 -methoxy-3-methyl-1-(1,5,6,7-tetrahydro-5,5,7,7 -tetramethyl-6-oxoindeno[5,6-d]imidazol-2-yl)pyridinium chloride obtained is filtered off and Washed with cold ethyl acetate; it exhibits a melting point of 160° (decomposition).

EXAMPLE 59

625 mg of 3-aminothiophenol are dissolved in 250 ml of tetrahydrofuran; gaseous hydrogen chloride is subsequently conducted in until the crystallized-out solid again passes into solution. The resulting solution is treated with 2 g of 5,7-dihydro-2-[[(4-methoxy-3 -methyl-2-pyridyl)methyl]sulphinyl]-5,5,7,7 -tetramethylindeno[5,6-d]imidazol-6(1H )-one and stirred at room temperature, whereby a solid begins to crystallize. A portion of the solvent is evaporated off, and the crystallized-out solid is filtered off and washed with tetrahydrofuran and ether. The 2-[[(m-aminophenyl)dithio]methyl]-1 -(1,5,6,7-tetrahydro-5,5,7,7-tetramethyl-6 -oxoindeno[5,6-d]imidazol-2-yl)-4-methoxy-3-methyl-pyridinium chloride hydrochloride obtained exhibits a melting point of 180°–210° (decomposition).

EXAMPLE 60

400 mg of cysteamine are dissolved in 50 ml of a 3.5N solution of gaseous hydrogen chloride in tetrahydrofuran. The solution is treated with 2 g of 5,7-dihydro-2-[[(4-methoxy-3 -methyl-2-pyridyl)methyl]sulphinyl]-5,5,7,7 -tetramethylindeno[5,6-d]imidazol-6(1H )-one, whereby there crystallizes out a solid which is filtered off and washed with tetrahydrofuran. The 2-[[(2-aminoethyl)dithio]methyl]-4 -methoxy-3-methyl-1-(1,5,6,7-tetrahydro-5,5,7,7 -tetramethyl-6-oXoindeno[5.6-d]imidazol-2-yl)pyridinium chloride hydrochloride obtained exhibits a melting point of 197°–200° (decomposition).

EXAMPLE 61

625 mg of 2-aminothiophenol are dissolved in 250 ml of tetrahydrofuran. The solution is stirred and warmed and gaseous hydrogen chloride is conducted in until the crystallized-out solid has again dissolved. The solution is treated with 2 g of 5,7-dihydro-2-[[(4-methoxy-3-methyl-2 -pyridyl)methyl]sulphinyl]-5,5,7,7 -tetramethylindeno[5,6-d]imidazol-6(1H )-one. whereby a solid crystallizes out. The solvent is partially removed, and the solid is filtered off and washed with tetrahydrofuran. The 2-[[(o-aminophenyl)dithio]methyl]-4 -methoxy-3-methyl-1-(1,5,6,7-tetrahydro-5,5,7,7 -tetramethyl-6-oxoindeno[5,6-d]imidazol-2-yl)pyridinium chloride dihydrochloride obtained exhibits a melting point of 159° (decomposition).

EXAMPLE 62

A solution of 820 mg of D,L-penicillamine in 20 ml of 1N aqueous hydrochloric acid is treated With 2 g of 5.7-dihydro-2-[[(4-methoxy-3-methyl-2 -pyridyl)methyl]sulphinyl]-5,5,7,7-tetramethylindeno[5,6-d]imidazol-6(1H )-one. There results a clear solution which is concentrated and treated with ethyl acetate. The crystallized-out solid is filtered off and washed with ethyl acetate. The 2-[[[(RS)-2-amino-2-carboxy-1,1 -dimethylethyl]dithio]methyl]-4-methoxy-3 -methyl-1-(1,5,6,7-tetrahydro-5,5,7,7-tetramethyl-6 -oxoindeno[5,6-d]imidazol-2-yl)pyridinium chloride obtained exhibits a melting point of 176° (decomposition).

EXAMPLE 63

680 mg of o-thiocresol are dissolved in 30 ml of about 6N methanolic hydrochloric acid. The solution is treated with 2 g of 5,7-dihydro-2-[[(4-methoxy-3-methyl-2 -pyridyl)methyl]sulphinyl]-5,5,7,7-tetramethylindeno[5,6-d]-imidazol-6(1H )-one, stirred at room temperature and then partially concentrated by means of a water-jet pump. About 20 ml of ethyl acetate are subsequently added thereto and the reaction mixture is stirred further until crystallization is complete. The 4-methoxy-3-methyl-1 (1,5,6,7-tetrahydro-5,5,7,7-tetramethyl-6 -oxoindeno[5,6-d]imidazol-2-yl)-2 -[(o-tolyldithio)methyl]pyridinium chloride obtained is filtered off and washed with cold ethyl acetate; it exhibits a melting point of 179° (decomposition).

EXAMPLE 64

850 mg of p-methoxybenzyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 4-methoxy-2-[[(p-methoxybenzyl)dithio]methyl]-3-methyl-1-(1,5,6,7-tetrahydro-5,5,7,7-tetramethyl-6-oxoindeno[5,6-d]imidazol-2-yl)pyridinium chloride hydrochloride obtained is filtered off and washed with cold ethyl acetate; it exhibits a melting point of 159°-160° (decomposition).

EXAMPLE 65

1 g of m-trifluoromethylbenzyl mercaptan is dissolved in 10 ml of methanol and in 10 ml of about 6N methanolic hydrochloric acid. The solution is treated with 2 g of 5,7-dihydro-2-[[(4-methoxy-3-methyl-2-pyridyl)methyl]-sulphinyl]-5,5,7,7 -tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 4-methoxy-3-methyl-1-(1,5,6,7-tetrahydro-5,5,7,7-tetramethyl-6-oxoindeno[5,6-d]imidazol-2-yl)-2-[[[m-(trifluoromethyl)benzyl]dithio]methyl]pyridinium chloride obtained is filtered off and washed with cold ethyl acetate; it exhibits a melting point of 162° (decomposition).

EXAMPLE 66

0.8 ml of 2-phenyl-ethyl mercaptan is dissolved in 30 ml of a 3.5N solution of gaseous hydrogen chloride in tetrahydrofuran. The solution is treated with 2 g of 5,7-dihydro-2-[[(4-methoxy-3-methyl-2-pyridyl)methyl]-sulphinyl]-5,5,7,7 -tetramethylindeno[5,6-d]imidazol-6(1H)-one, stirred at room temperature and then concentrated by means of a water-jet pump until a precipitate begins to crystallize out. The precipitate is filtered off and washed with tetrahydrofuran. The 4-methoxy-3-methyl-2-[(phenethyldithio)methyl]-1-(1,5,6,7-tetrahydro-5,5,7,7-tetramethyl-6 -oxoindeno[5,6-d]imidazol-2-yl)pyridinium chloride obtained exhibits a melting point of 165° (decomposition).

EXAMPLE 67

870 mg of 4-chlorobenzyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7 -tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 2-[[(p-chlorobenzyl)dithio]methyl]-4-methoxy-3-methyl-1-(1,5,6,7-tetrahydro-5,5,7,7 -tetramethyl-6-oxoindeno[5,6-d]imidazol- 2-yl)pyridinium chloride obtained is filtered off and washed with cold ethyl acetate; it exhibits a melting point of 178° (decomposition).

EXAMPLE 68

730 mg of 2-mercapto-5-methyl-1,3,4-thiadiazole are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7 -tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 4-methoxy-2-[[(5-methyl-1,3,4-thiadiazol-2-yl)dithio]methyl]-3-methyl-1-(1,5,6,7-tetrahydro-5,5,7,7-tetramethyl-6-oxoindeno[5,6-d]imidazol-2-yl)pyridinium chloride dihydrochloride obtained is filtered off and washed with cold ethyl acetate; it exhibits a melting point of 145° (decomposition).

EXAMPLE 69

930 mg of m-nitrobenzyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7 -tetramethylindeno[5,6-d]imidazol-6(1H)-one. stirred at room temperature and then partially concentrated by means of a water-jet pump. About 20 ml of ethyl acetate are subsequently added thereto and the reaction mixture is stirred further until crystallization is complete. The 4-methoxy-3-methyl-2-[[(m-nitrobenzyl)dithio]methyl]-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 166° (decomposition).

EXAMPLE 70

1.06 g of 3,4-dichlorobenzyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7 -tetramethylindeno[5,6-d]imidazol-6(1H)-one, stirred at room temperature and then partially concentrated by means of a water-jet pump. About 20 ml of ethyl acetate are subseguently added thereto and the reaction mixture is stirred further until crystallization is complete. The 2-[[(3,4-dichlorobenzyl)dithio]methyl]-4-methoxy-3-methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 180° (decomposition).

EXAMPLE 71

106 mg of 2,4-dichlorobenzyl mercaptan are dissolved in 5 ml of about 6N methanolic hydrochloric acid. The solution is treated with 200 mg of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then partially concentrated by means of a water-jet pump. About 2 ml of ethyl acetate are subseguently added thereto and the reaction mixture is stirred further until crystallization is complete. The 2-[[(2,4-dichlorobenzyl)dithio]methyl]-4-methoxy-3-methyl-1-(1,5,6,7-tetrahydro-5,5,7,7-tetramethyl-6-oxoindeno-[5,6-d]imidazol-2-yl)pyridinium chloride obtained is filtered off and washed with cold ethyl acetate: it exhibits a melting point of 183° (decomposition).

EXAMPLE 72

600 mg of 2-chloroallyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 2-[[(2-chloroallyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 176° (decomposition).

EXAMPLE 73

930 mg of o-nitrobenzyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 4-methoxy-3-methyl-2-[[(o-nitrobenzyl)dithio]methyl]-1-(1,5,6,7-tetrahydro-5,5,7,7-tetramethyl-6-oxoindeno-[5,6-d)imidazol-2-yl)pyridinium chloride obtained is filtered off and washed with cold ethyl acetate; it exhibits a melting point of 175° (decomposition).

EXAMPLE 74

630 mg of 3-mercapto-4-methyl-4H-1,2,4-triazole are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. stirred at room temperature and then partially concentrated by means of a water-jet pump. About 20 ml of ethyl acetate are subsequently added thereto and the reaction mixture is stirred further until crystallization is complete. The 4-methoxy-2-[[(4-methyl-4H-1,2,4-triazol-3-yl) dithio]methyl]-3-methyl-1-(1,5,6,7-tetrahydro-5,5,7,7-tetramethyl-6-oxoindeno[5,6-d]imidazol-2-yl)pyridinium chloride dihydrochloride obtained is filtered off and washed with cold ethyl acetate; it exhibits a melting point of 190° (decomposition).

EXAMPLE 75

920 mg of 4-acetylamino-thiophenol are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 2-[(p-acetanilidodithio)methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 200° (decomposition).

EXAMPLE 76

770 mg of 2-methoxy-thiophenol are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno-[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 4-methoxy-2-[[(o-methoxyphenyl)dithio]methyl]-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 176° (decomposition).

EXAMPLE 77

980 mg of 3,4-dichlorothiophenol are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 2-(((3,4-dichlorophenyl) dithio]methyl]-4-methoxy-3-methyl-1-(1,5,6,7-tetrahydro-5,5,7,7-tetramethyl-6-oxoindeno-[5,6-d]imidazol-2-yl)pyridinium chloride obtained is filtered off and washed with cold ethyl acetate; it exhibits a melting point of 182° (decomposition).

EXAMPLE 78

870 mg of o-chlorobenzyl mercaptan are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one, stirred at room temperature and partially concentrated by means of a water-jet pump. About 20 ml of ethyl acetate are subsequently added thereto and the reaction mixture is stirred further until crystallization is complete. The 2-[[(o-chlorobenzyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 183° (decomposition).

EXAMPLE 79

90 mg of m-trifluoromethyl-thiophenol are dissolved in 5 ml of a 3.5N solution of gaseous hydrogen chloride in tetrahydrofuran. The solution is treated with 200 mg of 5,7-dihydro-2-[[(4-methoxy-3-methyl-2-pyridyl)methyl]sulphinyl]-5,5,7,7-tetramethylindeno[5,6-d]imidazol-6(1H)-one, partially concentrated and treated with ethyl acetate. The crystallized-out solid is filtered off and washed with ethyl acetate. The 4-methoxy-3-methyl-1-(1,5,6,7-tetrahydro-5,5,7,7-tetramethyl-6-oxoindeno[5,6-d]imidazol-2-yl)-2-[[[m-(trifluoromethyl)phenyl]dithio]methyl]pyridinium chloride obtained exhibits a melting point of 166° (decomposition).

EXAMPLE 80

980 mg of 1-phenyl-5-mercapto-tetrazole are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7 -tetramethylindeno[5,6-d]imidazol-6(1H)-one, stirred at room temperature and then partially concentrated by means of a water-jet pump. About 20 ml of ethyl acetate are subsequently added thereto and the reaction mixture is stirred further until crystallization is complete. The 4-methoxy-3-methyl-2-[[(1-phenyl-1H -tetrazol-5-yl)dithio]methyl]-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 150° (decomposition).

EXAMPLE 81

940 mg of 4-hydroxy-2-mercapto-6-propylpyrimidine are dissolved in 20 ml of about 6N methanolic hydrochloric acid. The solution is treated with 2 g of 5 7-dihydro-2-[[(4-methoxy-3-methyl-2-pyridyl)methyl]sulphinyl]-5,5,7,7 -tetramethylindeno[5,6-d]imidazol-6(1H )-one. stirred at room temperature and then partially concentrated by means of a water-jet pump. About 20 ml of ethyl acetate are subsequently added thereto and the reaction mixture is stirred further until crystallization is complete. The 2-[[(4-hydroxy-6-propyl-2-pyrimidinyl)dithio]methyl]-4-methoxy-3-methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 170° (decomposition).

EXAMPLE 82

A solution of 750 mg of 2-mercaptobenzimidazole in 10 ml of 1N aqueous hydrochloric acid and 30 ml of methanol is treated with 2.05 g of 5,7-dihydro-2-[[(4-methoxy-3-methyl-2-pyridyl)methyl]sulphinyl]-5,5,7,7 -tetramethylindeno[5,6-d]imidazol-6(1H )-one. There results a clear solution which is concentrated and treated with ethyl acetate. The crystallized-out solid is filtered off and washed with ethyl acetate. The 2-[(2-benzimidazolyldithio)methyl]-4-methoxy-3-methyl-1-(1,5,6,7-tetrahydro-5,5,7,7 -tetramethyl-6-oxoindeno[5,6-d]imidazol-2-yl)pyridinium chloride hydrochloride obtained exhibits a melting point of 161°–175° (decomposition).

EXAMPLE 83

1.04 g of 4-bromothiophenol are dissolved in 20 ml of about 6N methanolic hydrochloric acid. The solution is treated with 2 g of 5,7-dihydro-2-[[(4-methoxy-3-methyl-2-pyridyl)methyl]sulphinyl]-5,5,7,7 -tetramethylindeno[5,6-d]imidazol-6(1H )-one, stirred at room temperature and then partially concentrated by means of a Water-jet pump. About 20 ml of ethyl acetate are subsequently added thereto and the reaction mixture is stirred further until crystallization is complete. The 2-[[(p-bromophenyl)dithio]methyl]-4-methoxy-3-methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 170° (decomposition).

EXAMPLE 84

A solution of 610 mg of 4-mercaptopyridine in 15 ml of 1N aqueous hydrochloric acid and 30 ml of methanol is treated with 2 g of 5,7-dihydro-2-[[(4-methoxy-3-methyl-2-pyridyl)methyl]sulphinyl]-5,5,7,7-tetramethylindeno[5,6-d]imidazol-6(1H )-one. There results a clear solution which is concentrated and treated with ethyl acetate. The crystallized-out solid is filtered off and washed with ethyl acetate. The 4-methoxy-3-methyl-2-[(4-pyridyldithio)methyl]-1 -(1,5,6,7-tetrahydro-5,5,7,7-tetramethyl-6-oxoindeno[5,6-d]imidazol-2-yl)pyridinium chloride hydrochloride obtained exhibits a melting point of 180° (decomposition).

EXAMPLE 85

77 mg of 4-methoxy-thiophenol are dissolved in 5 ml of about 6N methanolic hydrochloric acid. The solution is treated with 200 mg of 5,7-dihydro-2-[[(4-methoxy-3-methyl-2 -pyridyl)methyl]sulphinyl]-5,5,7,7 -tetramethylindeno[5,6-d]imidazol-6(1H)-one. stirred at room temperature and then partially concentrated by means of a water-jet pump. About 20 ml of ethyl acetate are subsequently added thereto and the reaction mixture is stirred further until crystallization is complete. The 2-[[(p-methoxyphenyl)dithio]methyl]-4 -methoxy-3-methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 166° (decomposition).

EXAMPLE 86

A solution of 3.59 g of 1-octadecanethiol in 45 ml of 1N aqueous hydrochloric acid and 170 ml of methanol is treated With 4.5 g of 5,7-dihydro-2-[[(4-methoxy-3-methyl-2 -pyridyl)methyl]sulphinyl]-5,5,7,7 -tetramethylindeno[5,6-d]imidazol-6(1H)-one. A clear solution results. The reaction mixture is stirred at room temperature, partially concentrated and the solution is cooled briefly to about 5°, whereupon the crystalline solid is filtered off and washed with water. The 4-methoxy-3-methyl-2 -[(octadecyldithio)methyl]-1 -(1,5,6,7-tetrahydro-5,5,7,7-tetramethyl-6 -oxoindeno[5,6-d]imidazol-2-yl)pyridinium chloride obtained exhibits a melting point of 150° (dec.).

EXAMPLE 87

A solution of 0.98 g of 2-mercapto-5-nitrobenzimidazole in 20 ml of 1N aqueous hydrochloric acid and 70 ml of methanol is treated with 2 g of 5,7-dihydro-2-[[(4-methoxy-3 -methyl-2-pyridyl)methyl]sulphinyl]-5,5,7,7-tetramethylindeno[5,6-d]imidazol-6(1H)-one. A clear solution results. The reaction mixture is stirred at room temperature, concentrated. The residue is dissolved in methanol/ethyl acetate and the solution is cooled briefly to about 5°, whereupon the crystalline solid is filtered off and washed with ethyl acetate. The 4-methoxy-3-methyl-2-[[(5-nitro-2 -benzimidazolyl)dithio]methyl]-1-(1,5,6,7-tetrahydro -5,5,7,7-tetramethyl-6 -oxoindeno[5,6-d]imidazol-2-yl)pyridinium chloride obtained exhibits a melting point of 188° (dec.).

EXAMPLE 88

A solution of 1.61 g of tert.octyl mercaptan in 30 ml of 1N aqueous hydrochloric acid and 160 ml of methanol is treated with 4 g of 5,7-dihydro-2-[[(4-methoxy-3 -methyl-2-pyridyl)methyl]sulphinyl]-5,5,7,7-tetramethylindeno[5,6-d]imidazol-6(1H)-one. A clear solution results. The reaction mixture is stirred at room temperature, partially concentrated and the solution is cooled briefly to about 5°, whereupon the crystalline solid is filtered off and washed with water. The 4-methoxy-3-methyl-2-[(tert.octyldithio)methyl]-1 -(1,5,6,7-tetrahydro-5,5,7,7-tetramethyl-6 -oxoindeno[5,6-d]imidazol-2-yl)pyridinium chloride obtained exhibits a melting point of 150° (dec.).

EXAMPLE 89

A solution of 1.09 g of n-heptyl mercaptan in 30 ml of 1N aqueous hydrochloric acid and 180 ml of methanol is treated with 3 g of 5,7-dihydro-2-[[(4-methoxy-3 -methyl-2-pyridyl)methyl]sulphinyl]-5,5,7,7-tetramethylindeno[5,6-d]imidazol-6(1H)-one. A clear solution results. The reaction mixture is stirred at room temperature, partially concentrated and the mixture is cooled briefly to about 5°, whereupon the crystalline solid is filtered off and washed with water. The 2-[(heptyldithio)methyl]-4-methoxy-3-methyl-1 -(1,5,6,7-tetrahydro-5,5,7,7 -tetramethyl-6-oxoindeno[5,6-d]imidazol-2-yl)pyridinium chloride obtained exhibits a melting point of 150° (dec.).

EXAMPLE 90

0.8 g of cyclohexylmercaptan is dissolved in 25 ml of about 6N methanolic hydrochloric acid. The solution is treated with 2.5 g of 5,7-dihydro-2 -[[(4-methoxy-3-methyl-2-pyridyl)methyl]sulphinyl]-5,5,7,7 -tetramethylindeno[5,6-d]imidazol-6(1H)-one, stirred at room temperature and then concentrated by means of a water-jet pump until a precipitate begins to crystallize out. At this moment about 20 ml of ethyl acetate are added thereto and the reaction mixture is stirred further until crystallization is complete. The 2-[(cyclohexyldithio)-methyl]-4 -methoxy-3-methyl-1 -(1,5,6,7-tetrahydro-5,5,7,7-tetramethyl-6 -oxoindeno[5,6-d]imidazol-2-yl)pyridinium chloride obtained is filtered off and washed with cold ethyl acetate; it exhibits a melting point of 200° C. (dec.).

EXAMPLE 91

0.98 g of 2.5-dichlorothiophenol is dissolved in 50 ml of about 6N methanolic hydrochloric acid. The solution is treated with 2 g of 5,7-dihydro-2 -[[(4-methoxy-3- methyl-2-pyridyl)methyl]sulphinyl]-5,5,7,7 -tetramethylindeno[5,6-d]imidazol-6(1H)-one, stirred at room temperature and then concentrated by means of a water-jet pump until a precipitate begins to crystallize out. At this moment about 20 ml of ethyl acetate are added thereto and the reaction mixture is stirred further until crystallization is complete. The 2-[[(2,5-dichlorophenyl)dithio]methyl]-4 -methoxy-3-methyl-1-(1,5,6,7-tetrahydro-5,5,7,7-tetramethyl-6-oxoindeno[5,6-d]imid chloride obtained is filtered off and washed with cold ethyl acetate; it exhibits a melting point of 169° (dec.).

EXAMPLE 92

0.98 g of 2,6-dichlorothiophenol is dissolved in 50 ml of about 6N methanolic hydrochloric acid. The solution is treated with 2 g of 5,7-dihydro-2 -[[(4-methoxy-3- methyl-2-pyridyl)methyl]sulphinyl]-5,5,7,7 -tetramethylindeno[5,6-d]imidazol-6(1H)-one, stirred at room temperature and then concentrated by means of a water-jet pump until a precipitate begins to crystallize out. At this moment about 20 ml of ethyl acetate are added thereto and the reaction mixture is stirred further until crystallization is complete. The 2-[[(2,6-dichlorophenyl)dithio]methyl]-4 -methoxy-3-methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 168° (dec.).

EXAMPLE 93

0.71 g of 1-octanethiol is dissolved in 50 ml of about 6N methanolic hydrochloric acid. The solution is treated with 2 g of 5 7-dihydro-2 -[[(4-methoxy-3-methyl-2-pyridyl)methyl]sulphinyl]-5,5,7,7 -tetramethylindeno[5,6-d]-imidazol-6(1H)-one, stirred at room temperature and then concentrated by means of a water-jet pump until a precipitate begins to crystallize out. At this moment about 20 ml of ether are added thereto and the reaction mixture is stirred further until crystallization is complete. The 4-methoxy-3-methyl-2-[(octyldithio)methyl]-1 -(1,5,6,7-tetrahydro-5,5,7 7-tetramethyl-6 -oxoindeno[5,6-d]imidazol-2-yl)pyridinium chloride obtained is filtered off and washed with cold ether; it exhibits a melting point of 164° (dec.).

EXAMPLE 94

A solution of 750 mg of thiomalic acid in 15 ml of 1N aqueous hydrochloric acid is treated with 1.73 g of 6-[[(4-methoxy-3-methyl-2 -pyridyl)methyl]sulphinyl]-5H -1,3-dioxolo[4,5-f]benzimidazole. There immediately results a solution which is warmed briefly to 40° and from which a solid begins to crystallize out. The reaction mixture is stirred at room temperature for 4 hours and then cooled briefly to about 5°, whereupon the crystalline product is filtered off and washed with cold water and ether. The 2-[[(1,2-dicarboxyethyl)dithio]methyl]-4-methoxy-3 -methyl-1-(5H-1,3 -dioxolo[4,5-f]benzimidazol-2-yl)pyridinium chloride obtained exhibits a melting point of 192° (dec.).

EXAMPLE 95

A solution of 590 mg of hexanethiol in 15 ml of 1N aqueous hydrochloric acid is treated with 1.73 g of 6-[[(4-methoxy-3-methyl-2 -pyridyl)methyl]sulphinyl]-5H -1,3 -dioxolo[4,5-f]benzimidazole. The solution is heated to 40°-50° and after about 10 minutes, the water is distilled off. The residue is taken up in methanol, the solution is concentrated, the residue is taken up in ethyl acetate and left to crystallize at about 5°, whereupon the crystalline product is filtered off and washed with cold ethyl acetate. The 1-(5H-1,3-dioxolo[4,5-f]benzimidazol-2 -yl)- -2-[(hexyldithio)methyl]-4-methoxy-3 -methylpyridinium chloride obtained exhibits a melting point of 135° (dec.).

EXAMPLE 96

A solution of 2 g of 1-dodecanethiol in 20 ml of 1N aqueous hydrochloric acid and 100 ml of methanol is treated with 3.4 g of 6-[[(4-methoxy-3-methyl-2 -pyridyl)methyl]sulphinyl]-5H-1,3 -dioxolo[4,5-f]benzimidazole. A clear solution results. The reaction mixture is stirred at room temperature, the solvent is evaporated, the residue is dissolved three times in methanol and the solvent is evaporated each time, whereupon the reaction product is crystallized from ethyl acetate and washed with cold ethyl acetate. The 1-(5H-1,3-dioxolo[4,5-f]benzimidazol-6 -yl)-2-[(dodecyldithio)methyl]-4-methoxy-3 -methyl]pyridinium chloride obtained exhibits a melting point of 138°-140° (dec.).

EXAMPLE 97

A solution of 560 mg of 2-mercaptopyrimidine in 15 ml of 1N aqueous hydrochloric acid and 1 ml of 5N aqueous hydrochloric acid is treated with 50 ml of methanol and 1.7 g of 6-[[(4-methoxy-3-methyl-2 -pyridyl)methyl]sulphinyl]-5H-1,3 -dioxolo[4,5-f]benzimidazole. After stirring at 40° for 30 minutes the solvent mixture is evaporated, the residue is dissolved three times in methanol and the solvent is evaporated each time. The reaction product is crystallized from a small amount of methanol/ethyl acetate and washed with cold ethyl acetate. The 1-(5H-1,3-dioxolo[4,5-f]benzimidazol-6 -yl)-4-methoxy-3-methyl-2 -[(2-pyrimidinyldithio)methyl]pyridinium chloride hydrochloride obtained exhibits a melting point of 158°-160° (dec.).

EXAMPLE 98

A solution of 0.35 g of L-cysteine in 5.8 ml of 1N aqueous hydrochloric acid and 35 ml of water is treated with 1 g of 2-[[(3,5-dimethyl-4-methoxy-2 -pyridyl)methyl]sulphinyl]-5-methoxybenzimidazole and dissolved in an ultrasound bath. The solution is lyophilized. The 2-[[(2-amino-2-carboxyethyl)dithio]methyl]-4 -methoxy-1-(5-methoxy-2-benzimidazolyl)-3,5 -dimethylpyridinium chloride hydrochloride obtained is stored at −20°. The cation of the salt is determined in MS-FAB*) (matrix: 3-nitro-benzyl alcohol) and gives the mass 449.
Mass spectroscopy with fast atom bombardment

EXAMPLE 99

A solution of 870 mg of thiomalic acid in 6 ml of 1N aqueous hydrochloric acid and 10 ml of water is treated with 2 g of 2-[[(3,5-dimethyl-4-methoxy-2 -pyridyl)methyl]sulphinyl]-5-methoxybenzimidazole and dissolved in an ultrasound bath. The solution is lyophilized. The 2-[[(1,2-dicarboxyethyl)dithio]methyl]-4 -methoxy-1-(5-methoxy-2 -benzimidazolyl)-3,5-dimethylpyridinium chloride obtained is stored at −20° and gives the following microanalysis:
Calc: C 47.98; H 4.66; N 7.99; S 12.20; Cl 8.90 Found: C 47.69; H 4.66; N 7.87; S 12.24; Cl 8.65. (the substance analyzed contained 0.32 molecular equivalent of HCl).

EXAMPLE 100

A solution of 650 mg of 2-mercaptopyrimidine in 12 ml of 1N aqueous hydrochloric acid and 10 ml of water is treated with 2 g of 2-[[(3,5-dimethyl-4-methoxy-2-pyridyl)methyl]sulphinyl]-5-methoxybenzimidazole and dissolved in an ultrasound bath. The solution is lyophilized. The 4-methoxy-1-(5-methoxy-2 -benzimidazolyl)-3,5-dimethyl-2 -[(2-pyrimidinyldithio)methyl]pyridinium chloride hydrochloride obtained is stored as -20°. The cation of the salt is determined in MS-FAB (matrix: 3-nitro-benzyl alcohol) and gives the mass 440.

EXAMPLE 101

A solution of 0.39 g of D,L-homocysteine in 6.9 ml of 1N aqueous hydrochloric acid and 30 ml of water is treated With 1 g of 2-[[(3,5-dimethyl-4-methoxy-2 -pyridyl)methyl]sulphinyl]-5-methoxybenzimidazole and dissolved in an ultrasound bath. The solution is lyophilized. The 2-[[(3-amino-3-carboxypropyl)dithio]methyl]-4 -methoxy-1-(5-methoxy-2-benzimidazolyl)-3,5 -dimethylpyridinium chloride hydrochloride obtained is stored at −20°. The cation of the salt is determined in MS-FAB (matrix: 3-nitro-benzyl alcohol) and gives the mass 463.

EXAMPLE 102

(a) To 500 ml of a 5% solution of methyl lithium in ether are added dropwise at room temperature under argon 1200 ml of ether, subsequently 35.6 g of 3,5-lutidine (3,5-dimethylpyridine) and subsequently 400 ml of toluene. The ether is distilled off completely, whereupon the solution is stirred at 100° for 4 hours. Ice is then added portionwise thereto while cooling with methanol/ice until evolution of heat no longer occurs. The toluene phase is separated from precipitated solid and extracted with 66 ml of semi-concentrated hydrochloric acid. The separated aqueous phase is adjusted to a pH of about 10 with 3N sodium hydroxide solution while cooling and extracted twice with 300 ml of ether. The ether extracts are dried over sodium sulphate and evaporated. The residue is distilled in vacuo at 20 mm/72°-74°; there is obtained 2,3,5-collidine (2,3,5-trimethylpyridine) which has a purity of 99.15% according to gas chromatography.

(b) 420 ml of 30% hydrogen peroxide are added dropwise at room temperature to 246.4 g of 2,3,5-collidine and 2400 ml of glacial acetic acid. The solution is stirred at 80° overnight. The reaction mixture is then cooled to 40°, a further 420 ml of 30% hydrogen peroxide are added thereto and the mixture is heated to 80° for a further 24 hours. After evaporation in vacuo the residue is dissolved in 300 ml of water, whereupon the solution is made basic with conc. sodium hydroxide solution while cooling, saturated with sodium chloride and extracted three times with 1 l of methylene chloride. The organic phases are dried over sodium sulphate and evaporated in vacuo. The residue is crystallized from ether/petroleum ether; there is obtained 2,3,5-trimethylpyridine 1-oxide of melting point 42°-44°.

(c) 65 ml of fuming nitric acid (d = 1.5) are added dropwise to 210 ml of conc. sulphuric acid while cooling. 96.5 g of 2,3,5-trimethylpyridine 1-oxide are subsequently added portionwise at 0°-5°, whereupon the mixture is stirred at room temperature for 1 hour, then heated to 90° within 3 hours and left at this temperature overnight. After cooling the solution is poured on to 1.5 kg of ice, whereupon the mixture is adjusted to pH 3 with conc. sodium hydroxide solution and extracted three times with 500 ml of methylene chloride. The combined organic phases are washed with 1 l of water, dried over sodium sulphate and evaporated in vacuo. The residue is crystallized from ether/petroleum ether and there is obtained 2,3,5-trimethyl-4-nitropyridine 1-oxide of melting point 76°-78°.

(d) 22.6 g of sodium are dissolved in 4 l of methanol under argon. 120 g of 2,3,5-trimethyl-4-nitropyridine 1-oxide are then added portionwise thereto and the solution is left to boil under reflux overnight. The pH is adjusted to 7 by means of 5N hydrogen chloride in ethyl acetate while cooling and the mixture is then evaporated in vacuo. The residue is taken up in 1.5 l of methylene chloride, the solution is filtered throuqh siliceous earth, which is rinsed with 0.5 l of methylene chloride, the combined filtrates are evaporated in vacuo and the residue is crystallized from petroleum ether. There is obtained 4-methoxy-2,3,5-trimethylpyridine 1-oxide of melting point 48°-50°.

(e) 215 ml of acetic anhydride are added dropwise at room temperature to a solution of 81.5 g of 4-methoxy-2,3,5-trimethylpyridine 1-oxide in 290 ml of chloroform.

After boiling under reflux for 4 hours the solution is evaporated, the residue is dissolved in 200 ml of toluene and again evaporated. The residue is taken up in 500 ml of ethyl acetate and shaken out three times with 250 ml of saturated sodium bicarbonate solution. The organic phase is dried over sodium sulphate and evaporated in vacuo. The crude product remaining behind as the residue is chromatographed on 400 g of silica gel with ether. There is obtained (4-methoxy-3,5-dimethyl-2-pyridyl)methyl acetate in the form of an oil.

(f) 94.9 g of (4-methoxy-3,5-dimethyl-2-pyridyl)-methyl acetate are dissolved in 570 ml of ethanol. 285 ml of 3N sodium hydroxide solution are then added dropwise thereto at 0° and the mixture is stirred at room temperature for 3 hours. The ethanol is subsequently removed in vacuo, whereupon the residual aqueous solution is extracted three times with 300 ml of methylene chloride. The organic extracts are dried over sodium sulphate and evaporated in vacuo. The residue is crystallized from petroleum ether and there is obtained 4-methoxy-3,5-dimethyl-2-pyridylmethanol of melting point 49°–51°.

(g) 75.8 g of 4-methoxy-3,5-dimethyl-2-pyridylmethanol dissolved in 200 ml of methylene chloride are added dropwise at 0° to 38 ml of thionyl chloride in 400 ml of methylene chloride. After stirring at room temperature for 16 hours 1800 ml of ether are added dropwise thereto while cooling and the mixture is stirred further at room temperature for 2 hours. The precipitated crystals are filtered off under suction and washed with ether. There is obtained 2-(chloromethyl)-4-methoxy-3,5-dimethylpyridine hydrochloride of melting point 130°–131°.

(h) 18.0 g (69.2 mmol) of 5,7-dihydro-2 -mercapto-5,5,7,7-tetramethylindeno[5,6-d]imidazol-6(1H)-one are suspended in 400 ml of alcohol and treated with 15.6 g (70.2 mmol) of 2-(chloromethyl)-4-methoxy-3,5-dimethylpyridine hydrochloride while cooling with ice. Thereafter, a solution of 5.6 g of sodium hydroxide in 150 ml of water is added dropwise thereto, the mixture is left to boil at reflux overnight and subseguently evaporated to dryness in vacuo. The residue is dissolved in 1000 ml of methylene chloride; the solution is washed firstly with 500 ml of 1.5N sodium hydroxide solution and then with 3×500 ml of water, dried over sodium sulphate and evaporated in vacuo. The crude product is purified on 300 g of silica gel with ethyl acetate/methylene chloride (1:1) as the elution agent. Crystallization from methylene chloride/petroleum ether gives 5,7-dihydro-2-[[(4-methoxy-3,5 -dimethyl-2ether -pyridyl)-methyl]thio]-5,5,7,7 -tetramethylindeno[5,6-d)-imidazol-6(1H)-one of melting point 166°–168°.

(i) 8.3 g of 5,7-dihydro-2-[[(4-methoxy-3,5 -dimethyl-2-pyridyl)methyl]thio]-5,5,7,7 -tetramethylindeno[5,6-d]-imidazol-6(1H)-one are dissolved in 1000 ml of methylene chloride and cooled to −10° with an ice/methanol bath. 4.3 g of m-chloroperbenzoic acid, recrystallized from methylene chloride/petroleum ether, are then introduced within 25 minutes. The solution is stirred further at −10° for 45 minutes and then poured into a mixture of 100 ml of 2N sodium carbonate solution and ice. The aqueous phase is extracted twice with 300 ml of methylene chloride. The combined organic phases are washed neutral three times with 200 ml of water, dried over sodium sulphate and concentrated in vacuo at 35° to a volume of 150 ml. 5.7-Dihydro-2-[[(4-methoxy-3,5-dimethyl-2 -pyridyl)methyl]sulphinyl]-5,5,7,7 -tetramethylindeno[5,6-d]imidazol-6(1H)-one of melting point 192°–194° crystallizes upon adding petroleum ether.

(j) 576 mg of 2-chlorothiophenol are dissolved in 5 ml of a 3.5N solution of gaseous hydrogen chloride in tetrahydrofuran and 10 ml of tetrahydrofuran. The solution is treated with 1.7 g of 5,7-dihydro-2 -[[(4-methoxy-3,5-dimethyl-2-pyridyl)methyl]sulphinyl]-5,5,7,7 -tetramethylindeno[5,6-d]imidazol-6(1H) stirred at 40° for 10 minutes and the solvent is partially evaporated by means of a water-jet pump. After adding t-butyl methyl ether the reaction product is crystallized, filtered off and washed with t-butyl methyl ether. The 2-[[(o-chlorophenyl)dithio]methyl]-4 -methoxy-3,5-dimethyl-1-(1,5,6,7-tetrahydro-5,5,7,7 -tetramethyl-6-oxoindeno[5,6-d]imidazol-2-yl) pyridinium chloride obtained exhibits a melting point of 170°–176° (decomposition).

EXAMPLE 103

2.4 g of n-hexyl mercaptan are dissolved in 10 ml of a 3.5N solution of gaseous hydrogen chloride in tetrahydrofuran and 20 ml of tetrahydrofuran. The solution is treated with 8.5 g of 5,7-dihydro-2-[[(4-methoxy-3,5-dimethyl-2 -pyridyl)methyl]sulphinyl]-5,5,7,7 -tetramethylindeno[5,6-d]imidazol-6(1H)-one; there thereby crystallizes a solid which is again brought into solution completely by stirring at 40°–50°. The solvent is subsequently partially evaporated by means of a water-jet pump and replaced by t-butyl methyl ether. The reaction product is crystallized, filtered off and washed with t-butyl methyl ether. The 2-[(hexyldithio)methyl]-4-methoxy-3,5-dimethyl--(1,5,6,7-tetrahydro-5,5,7,7 -tetramethyl-6-oxoindeno[5,6-d]imidazol-2-yl)pyridinium chloride obtained exhibits a melting point of 123°–125° (decomposition).

EXAMPLE 104

750 mg of thiomalic acid are dissolved in 5 ml of 3.5N solution of gaseous hydrogen chloride in tetrahydrofuran. The solution is treated with 2.1 g of 5,7-dihydro-2-[[(4-methoxy-3,5-dimethyl-2 -pyridyl)methyl]sulphinyl]-5,5,7,7-tetramethylindeno[5,6 -d]imidazol-6(1H)-one, stirred at 40° for a half hour and the solvent is partially evaporated by means of a water-jet pump. The solution is subsequently treated with ethyl acetate, whereby the reaction product crystallizes, is filtered off and washed with ethyl acetate. The 2-[[(1,2-dicarboxyethyl)dithio]methyl]-4 -methoxy-3,5-dimethyl-1 -(1,5,6,7-tetrahydro-5,5,7,7-tetramethyl-6 -oxoindeno[5,6-d]imidazol-2-yl)pyridinium chloride obtained exhibits a melting point of 187°–189° (decomposition).

EXAMPLE 105

434 mg of m-chlorothiophenol are dissolved in 3 ml of a 4N solution of gaseous hydrogen chloride in tetrahydrofuran and 10 ml of tetrahydrofuran. The solution is treated with 1.28 g of 5,7-dihydro-2-[[(4-methoxy-3,5-dimethyl-2 -pyridyl)metbyl]sulphinyl]-5,5,7,7-tetramethylindeno[5,6 d]imidazol-6(1H)-one. stirred at 40° for 10 minutes and the solvent is partially evaporated by means of a water-jet pump. After adding t-butyl methyl ether the reaction product is crystallized, filtered off and washed with t-butyl methyl ether. The 2-[[(m-chlorophenyl)dithio]methyl]-4 -methoxy-3,5-dimethyl-1-(1,5,6,7-tetrahydro-5,5,7,7-tetramethyl-6-oxoindeno[5,6-d]imidazol-2-yl)pyridinium chloride obtained exhibits a melting point of 155°–160° (decomposition).

EXAMPLE 106

3.3 ml of n-hexanethiol are dissolved in 22 ml of a 3.5N solution of gaseous hydrogen chloride in tetrahydrofuran and 50 ml of tetrahydrofuran. The solution is treated with 9 g of 5,6,7,8-tetrahydro-2 -[[(4-methoxy-3-methyl-2 -pyridyl)methyl]sulphinyl]-5,5,8,8-tetramethyl-1H -naphth[2,3-d]imidazole, stirred at room temperature for about 15 minutes and the solvent is evaporated by means of a water-jet pump. The residue is crystallized with ether, filtered off and washed with ether. The 2-[(hexyldithio)methyl]-4 -methoxy-3-methyl-1-(5,6,7,8-tetrahydro-5,5,8,8 -tetramethyl-1H-naphtho[2,3-d]imidazol-2-yl)pyridinium chloride obtained exhibits a melting point of 153° (decomposition).

EXAMPLE 107

145 mg of 2-chlorothiophenol are dissolved in 2 ml of a 3.5N solution of gaseous hydrogen chloride in tetrahydrofuran and 3 ml of tetrahydrofuran. The solution is treated with 412 mg of 5,6,7,7,8-tetrahydro-2 -[[(4-methoxy-3-methyl-2 -pyridyl)methyl]sulphinyl]-5,5,8,8-tetramethyl-1H -naphth[2,3-d]imidazole, stirred briefly at room temperature and the solvent is evaporated by means of water-jet pump. The residue is crystallized with t-butyl methyl ether, filtered off and washed with t-butyl methyl ether. The 2- ((o-chlorophenyl)dithio)-methyl)-4 -methoxy-3-methyl-1-(5,6,7,8-tetrahydro-5,5,8,8 -tetramethyl-1H-naphtho[2,3-d]imidaZol-2-yl)pyridinium chloride obtained exhibits a meltinq point of 175° (decomposition).

EXAMPLE 108

750 mg of thiomalic acid are dissolved in 5 ml of a 3.5N solution of gaseous hydrogen chloride in tetrahydrofuran. The solution is treated with 2.1 g of 5,7-dihydro-2-[[(4-methoxy-3,5 -dimethyl-2-pyridyl)methyl]sulphiryl]-5,5,7,7 -tetramethylindeno[5,6-d]imidazol-6(1H)-one, stirred at 40° and the solvent is partially evaporated by means of a water-jet pump. After adding ethyl acetate the reaction product crystallizes and is filtered off and washed with ethyl acetate. The 2-[[(1,2-dicarboxyethyl)dithio]methyl]-4 -methoxy-3,5-dimethyl-1-(1,5,6,7-tetra-hydro-5,5,7,7 -tetramethyl-6-oxoindeno[5,6-d]imidazol-2-yl)pyridinium chloride obtained exhibits a melting point of 189° (decomposition).

EXAMPLE 109

(a) A solution of 5 g of 5-methoxy-2 [[(4-methoxy-3-methyl-2-pyridyl)methyl]thio]benzimidazole in 80 ml of abs. methylene chloride is treated under argon at −30° within 10 minutes with a solution of 3 g of m-chloroperbenzoic acid in 30 ml of abs. methylene chloride. The solution is subsequently stirred for an additional 10 minutes, extracted with 10% sodium carbonate solution, dried and evaporated. The residue is dissolved in ethyl acetate and crystallized with ether. The 5-methoxy-2-[[(4-methoxy-3 -methyl-2-pyridyl)methyl]-sulphinyl]benzimidazole obtained exhibits a melting point of 120° (decomposition).

(b) A solution of 713 mg of n-hexyl mercaptan and 2 g of 5-methoxy-2-[[(4-methoxy-3 -methyl-2-pyridyl)methyl]sulphinyl]benzimidazole in 6 ml of 1N aqueous hydrochloric acid is evaporated, whereupon the residue is dissolved in methanol and the solution is concentrated once more. The reaction product is crystallized from methanol/ethyl acetate. The 2-[(hexyldithio)methyl]-4 -methoxy-1-(5-methoxy-2-benzimidazolyl)-3-methyl-pyridinium chloride obtained exhibits a melting point of 135° (decomposition).

EXAMPLE 110

677 mg of 2-mercaptopyrimidine are dissolved in 60 ml of abs. methanol and 12 ml of about 6N methanolic hydrochloric acid. The solution is treated with 2 g of 5-methoxy-2-[[(4-methoxy-3 -methyl-2-pyridyl)methyl]sulphinyl]benzimidazole, stirred at room temperature, then partially concentrated by means of a water-jet pump and ethyl acetate is added thereto until a precipitate begins to crystallize out. The reaction mixture is stirred further until crystallization is complete. The 4-methoxy-1-(5-methoxy-2-benzlmidazolyl)-3 -methyl-2-[(2-pyrimidinyldithio)methyl]pyrldinium chloride hydrochloride obtained is filtered off and washed with cold ethyl acetate; it exhibits a melting point of 144° (decomposition).

EXAMPLE 111

930 mg of thiosalicylic acid are dissolved in 6 ml of a 3.5N solution of gaseous hydrogen chloride in tetrahydrofuran and 60 ml of tetrahydrofuran. The solution is treated with 2 g of 5-methoxy-2-[[(4-methoxy-3 -methyl-2-pyridyl)methyl]sulphinyl]benzimidazole. The reaction mixture is stirred at 40°–50° and treated with water until the separated precipitate passes completely into solution. The solvent is partially evaporated and replaced continuously by ethyl acetate. The crystalline reaction product is filtered off and washed with ethyl acetate. The 2-[[(o-carboxyphenyl)dithio]methyl]-4 -methoxy-1-(5-methoxy-2-benzimidazolyl)-3-methyl-pyridinium chloride obtained exhibits a melting point of 163° (decomposition).

EXAMPLE 112

770 mg of thiosalicylic acid are dissolved in 5 ml of a 3N solution of gaseous hydrogen chloride in tetrahydrofuran and 15 ml of tetrahydrofuran and treated with 1.7 g of 6-[[(4-methoxy-3-methyl-2 -pyridyl)methyl]sulphinyl]-5H-1,3 -dioxolo[4,5-f]benzimidazole. Subsequently, 5 ml of 1N aqueous hydrochloric acid are added thereto and the reaction mixture is boiled briefly, whereby a clear solution results. The majority of the solvent mixture is evaporated; the reaction product is crystallized out by adding ethyl acetate, filtered off and washed with ethyl acetate. The 2-[[(o-carboxyphenyl)-dithio]methyl]-1 -(5H-1,3-dioxolo[4,5-f]benzimidaZol-6-yl)-4 -methoxy-3-methylpyridinium chloride obtained exhibits a melting point of 208° (decomposition).

EXAMPLE 113

1 ml of ethyl mercaptan is dissolved in 25 ml of methanol and 10 ml of about 3N methanolic hydrochloric acid. The solution is treated with 2 g of 6-[[(4-methoxy-3-methyl-2 -pyridyl)methyl]sulphinyl]-5H -1,3-dioxolo[4,5-f]benzimidazole, stirred at reflux temperature for 15 minutes and the solvent is then evaporated by means of a water-jet pump, whereby the methanol is replaced continuously by ethyl acetate. The reaction mixture is stirred further until crystallization is complete. The 1-[5H-1,3-dioxolo[4,5-f]benzimidazol-2-yl]-2 -[(ethyldithio)methyl]-4-methoxy-3-methylpyridinium chloride hydrochloride obtained is filtered off and washed with cold ethyl acetate; it exhibits a melting point of 158°–160° (decomposition).

EXAMPLE 114

904 mg of thiomalic acid are dissolved in 6 ml of a 3.5N solution of gaseous hydrogen chloride in tetrahydrofuran. The solution is treated with 2 g of 5-methoxy-2-[[(4-methoxy-3 -methyl-2-pyridyl)methyl]sulphinyl]-benzimidazole and the suspension is stirred at 50° for 90 minutes. The separated black sediment is filtered off. The filtrate is partially freed from solvent in a water-jet vacuum, whereupon ethyl acetate is added. The reaction product is crystallized, filtered off and washed with a small amount of ethyl acetate. The 2-[[(1,2-dicarboxyethyl)dithio]methyl]-4 -methoxy-1-(5-methoxy-2-benzimidazolyl)-3-methylpyridinium chloride obtalned exhibits a melting point of 170° (dec.).

EXAMPLE 115

750 mg of 2-chlorothiophenol are dissolved in 5 ml of about 3N methanolic hydrochloric acid and 5 ml of methanol. The solution is treated with 1.5 g of 5-methoxy-2-[[(4-methoxy-3 -methyl-2-pyridyl)methyl]sulphinyl] -benzimidazole and stirred at 50° for a half hour. The solvent is partially removed in a water-jet vacuum and replaced by ethyl acetate. The reaction product is crystallized, filtered off and washed with a small amount of ethyl acetate. The 2-[[(o-chlorophenyl)dithio]methyl]-4-methoxy-1 -(5-methoxy-2-benzimidazolyl)-3-methylpyridinium chloride is filtered off and washed with cold ethyl acetate; it exhibits a melting point of 138° (dec.).

EXAMPLE 116

112 mg of 2-mercaptopyrimidine are dissolved in 1 ml of 3N methanolic hydrochloric acid and 15 ml of methanol. The solution is treated with 425 mg of 5,7-dihydro-2-[[(4-methoxy-3,5-dimethyl -2-pyridyl)methyl]sulphinyl]-5,5,7,7-tetramethylindeno[5,6-d]imidazol-6(1H)-one, stirred at 40° for 5 minutes and the methanol is then evaporated up to a few milliliters by means of a water-jet pump. About 10 ml of t-butyl methyl ether are added thereto and the reaction product is crystallized. The 4-methoxy-3,5-dimethyl-2 -[(2-pyrimidinyldithio)methyl]-1-(1,5,6,7-tetrahydro -5,5,7,7-tetramethyl-6-oxoindeno[5,6-d]imidazol-2 -yl)pyridinium chloride obtained is filtered off and washed with cold t-butyl methyl ether; it exhibits a melting point of 170° (dec.).

EXAMPLE 117

0.5 ml of ethyl mercaptan is dissolved in 4 ml of a 3N solution of gaseous hydrogen chloride in tetrahydrofuran and 5 ml of tetrahydrofuran. The solution is treated with 1.2 g of 5,7-dihydro-2-[[(4-methoxy-3,5-dimethyl -2-pyridyl)methyl]sulphinyl]-5,5,7,7-tetramethylindeno5,6-d]imidazol-6(1H)-one and stirred at 40° for 10 minutes. The tetrahydrofuran is partially removed in a water-jet vacuum; crystallization occurs upon adding ethyl acetate/ether. The 2-[(ethyldithio)methyl]-4-methoxy-3,5-dimethyl-1 -(1,5,6,7-tetrahydro-5,5,7,7 -tetramethyl-6-oxoindeno[5,6-d]imidazol-2-yl)pyridinium chloride obtained is filtered off and washed with ether; it exhibits a melting point of 195° (dec.).

EXAMPLE 118

760 mg of 2-bromothiophenol are dissolved in 10 ml of 3N methanolic hydrochloric acid and 10 ml of methanol. The solution is treated with 1.6 g of 5,7-dihydro-2-[[(4-methoxy-3-methyl -2-pyridyl)methyl]sulphinyl]-5,5,7,7-tetramethylindeno(5,6-d)imidazol-6(1H)-one and stirred at 40° for 5 minutes. The methanol is partially removed in a water-jet vacuum and replaced by ethyl acetate. The crystalline 2-[[(o-bromophenyl)dithio]methyl]-4 -methoxy-3-methyl-1-(1,5,6,7-tetrahydro-5,5,7,7 -tetramethyl-6-oxoindeno[5,6-d]imidazol-2-yl)pyridinium chloride obtained is filtered off and washed with cold ethyl acetate; it exhibits a melting point of 175°–178° (dec.).

EXAMPLE 119

720 mg of 2,3-dichlorothiophenol are dissolved in 8 ml of 3N methanolic hydrochloric acid and 12 ml of methanol. The solution is treated with 1.64 g of 5,7-dihydro-2-[[(4-methoxy-3-methyl -2-pyridyl)methyl]-sulphinyl]-5,5,7,7-tetramethylindeno[5,6-d]imidazol-6(1H)-one and stirred at room temperature for 5 minutes. The methanol is partially removed in a water-jet vacuum and replaced by ethyl acetate. The crystalline 2-[[(2,3-dichlorophenyl)dithio]methyl]-4 -methoxy-3-methyl-1-(1,5,6,7-tetrahydro-5,5,7,7 -tetramethyl-6-oxoindeno[5,6-d]imidachloride obtained is filtered off and washed with cold ethyl acetate; it exhibits a melting point of 180° (dec.).

EXAMPLE 120

630 mg of m-fluorothiophenol are dissolved in 10 ml of 3N methanolic hydrochloric acid and 20 ml of methanol. The solution is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one and stirred at room temperature for 5 minutes. The methanol is partially removed in a water-jet vacuum and replaced by ethyl acetate. The crysralline 2-[[(m-fluorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 173° (dec.).

EXAMPLE 121

720 mg of 2,4-dichlorothiophenol are dissolved in 8 ml of 3N methanolic hydrochloric acid and 20 ml of methanol. The solution is treated with 1.65 g of 5,7-dihydro-2-[[(4-methoxy-3-methyl-2-pyridyl)methyl]sulphinyl]-5,5,7,7-tetramethylindeno[5,6-d]imidazol-6(1H)-one and stirred at 50° for 5 minutes. The methanol is partially removed in a water-jet vacuum and replaced by ethyl acetate; the reaction product even begins to crystallize from methanol. The 2-[[(2,4-dichlorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 197° (dec.).

EXAMPLE 122

195 mg of m-bromothiophenol are dissolved in 1 ml of 3N methanolic hydrochloric acid and 5 ml of methanol. The solution is treated with 411 mg of 5,7-dihydro-2-[[(4 -methoxy-3-methyl-2-pyridyl)methyl]sulphinyl]-5,5,7,7-tetramethylindeno[-5,6-d]imidazol-6(1H)-one and stirred at room temperature for 5 minutes. The methanol is partially removed in a water-jet vacuum and replaced by ethyl acetate. The crystalline 2-[[(m-bromophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride obtained is filtered off and washed with cold ethyl acetate; it exhibits a melting point of 160° (dec.).

EXAMPLE 123

750 mg of 3-chlorothiophenol are dissolved in 5 ml of 3N methanolic hydrochloric acid and 20 ml of methanol. The solution is treated with 1.725 g of 6-[[(4-methoxy-3-methyl-2-pyridyl)methyl]sulphinyl]-5H -1,3-dioxolo[4,5-f]benzimidazole and heated on a water-bath until a clear solution results. The solution is subsequently stirred at 45° for 30 minutes, treated with ethyl acetate and partially concentrated. The crystalline 2-[[(m-chlorophenyl)dithio]methyl]-1 -(5H-1,3-dioxolo[4,5-f]benzimidazol-6-yl)-4-methoxy-3-methyl-pyridinium chloride obtained is filtered off and washed with cold ethyl acetate: it exhibits a melting point of 191° (dec.).

EXAMPLE 124

1 ml of n-propyl mercaptan is dissolved in 5 ml of 3N methanolic hydrochloric acid and 20 ml of methanol. The solution is treated with 1.7 g of 6-[[(4-methoxy-3-methyl-2-pyridyl)methyl]sulphinyl]-5H -1,3-dioxolo[4,5-f]benzimidazole and heated under reflux for 15 minutes until all has dissolved. The reaction mixture is subsequently stirred at 40°-45° for 20 minutes, whereupon the solvent is partially evaporated and replaced by ethyl acetate. The crystalline 1-(5H-1,3-dioxolo[4,5-f)benzimidazol- 6-yl)-4-methoxy-3-methyl-2[(propyldithio)methyl]pyridinium chloride obtained is filtered off and washed with cold ethyl acetate: it exhibits a melting point of 165° (dec.).

EXAMPLE 125

(a) 14.8 g (76.7 mmol) of 5H-1,3-dioxolo[4,5-f]benzimidazole-6-thiol are suspended in 300 ml of alcohol and treated with 170 g (76.5 mmol) of 2-chloromethyl-4-methoxy-3,5-dimethylpyridine hydrochloride while cooling with ice. Thereafter, a solution of 6.0 g of sodium hydroxide in 150 ml of water is added dropwise thereto, the mixture is left to boil at reflux overnight and subsequently evaporated to dryness in vacuo. The residue is dissolved in 1000 ml of methylene chloride. The solution is washed firstly with 500 ml of 1.5N sodium hydroxide solution and then with 3×500 ml of water, dried over sodium sulphate and evaporated in vacuo. The crude product is purified on 300 g of silica gel with ethyl acetate/methylene chloride (1:1) as the elution agent. Crystallization from methylene chloride/petroleum ether gives 6-[[(4-methoxy-3,5-dimethyl-2-pyridyl)methyl]thio]-5H-1,3-dioxolo[4,5-f]benzimidazole of melting point 178°-179°.

(b) 13.3 g of 6-[[(4-methoxy-3,5-dimethyl-2-pyridyl)-methyl]thio]-5H -1,3-dioxolo[4,5-f]benzimidazole are dissolved in 300 ml of methylene chloride and cooled to −10° with an ice/methanol bath. 7.5 g of m-chloroperbenzoic acid, recrystallized from methylene chloride/petroleum ether, are then introduced within 30 minutes. The solution is stirred at −10° for a further 120 minutes and then poured into a mixture of 300 ml of 2N sodium carbonate solution and ice. The aqueous phase is extracted twice with 300 ml of methylene chloride. The combined organic phases are washed neutral three times with 250 ml of water, dried over sodium sulphate and concentrated in vacuo at 35° to a volume of 150 ml. Addition of petroleum ether brings about crystallization of 6-[[(4-methoxy-3,5-dimethyl-2-pyridyl)methyl]sulphinyl]-5H-1,3 -dioxolo[4,5-f]benzimidazole; m.p. 192°-194°.

(c) 0.5 ml of n-propyl mercaptan are dissolved in 4 ml of 3N methanolic hydrochloric acid and 20 ml of methanol. The solution is treated with 1.8 g of 6-[[(4-methoxy-3,5-dimethyl-2-pyridyl)methyl]sulphinyl]-5H-1,3 -dioxolo[4,5-f]benzimidazole and stirred at 45° for 20 minutes. Subsequently, the solvent is partially removed in a water-jet vacuum and replaced by ethyl acetate. The crystalline 1-(5H-1,3-dioxolo[4,5-f]benzimidazol-6-yl)-4-methoxy-3,5-dimethyl-2-[(propyldithio)methyl]-pyridinium chloride obtained is filtered off and washed with cold ethyl acetate; it exhibits a melting point of 111°-120° (dec.).

EXAMPLE 126

906 mg of 3-chlorothiophenol are dissolved in 6 ml of 3N methanolic hydrochloric acid and 20 ml of methanol. The solution is treated with 2 q of 5-methoxy-2-[[(4-methoxy-3-methyl-2-pyridyl)methyl)sulphinyl]benzimidazole and stirred at 40° for 2 hours. Subsequently, the solvent is partially removed in a water-jet vacuum and replaced by ethyl acetate. The crystalline 2-[[(m-chlorophenyl)dithio]methyl]-4-methoxy-3-methyl-1-(5-methoxy-2-benzimidazolyl)pyridinium chloride obtained is filtered off and washed with cold ethyl acetate; it exhibits a melting point of 137° (dec.).

EXAMPLE 127

508 mg of n-propyl mercaptan are dissolved in 6 ml of 3N methanolic hydrochloric acid and 20 ml of methanol. The solution is treated with 2 g of 5-methoxy-2-[[(4-methoxy-3-methyl-2-pyridyl)methyl]sulphinyl]benzimidazole and stirred at 40° for 10 minutes. Subsequently, the solvent is partially removed in a water-jet vacuum and replaced by ethyl acetate. The crystalline 4-methoxy-1-(5-methoxy-2-benzimidazolyl)3-methyl-2-[(propyldithio)methyl]-pyridinium chloride is filtered off and washed with cold ethyl acetate; it exhibits a melting point of 144° (dec.).

EXAMPLE 128

408 mg of n-propyl mercaptan are dissolved in 5 ml of a 3.5N solution of gaseous hydrogen chloride in tetrahydrofuran and 20 ml of tetrahydrofuran. The solution is treated with 2 g of 5,6,7,8-tetrahydro-2-[[(4-methoxy-3-methyl-2pyridyl)methyl]sulphinyl]-5,5,8,8-tetramethyl-1H-naphth[2,3-d]imidazole and stirred at room temperature for 5 minutes. Subsequently, the tetrahydrofuran is partially removed in a water-jet vacuum and replaced by ethyl acetate. The crystalline 4-methoxy-3-methyl-2-[(propyldithio)methyl]-1(5,6,7,8-tetrahydro-5,5,8,8-tetramethyl-1H-naphth[2,3-d)imidazol-2-yl)pyridinium chloride obtained is filtered off and washed with cold ethyl acetate; it exhibits a melting point of 163° (dec.).

EXAMPLE 129

1 ml of ethyl mercaptan is dissolved in 10 ml of 3N methanolic hydrochloric acid and 50 ml of methanol. The solution is treated with 2 g of 5,6,7,8-tetrahydro-2-[[(4methoxy-3-methyl-2-pyridyl)methyl]sulphinyl]-5,5,8,8-tetramethyl-1H-naphth[2,3d]imidazole and stirred at room temperature for 10 minutes. Subsequently, the solvent is partially removed in a water-jet vacuum and replaced by ether. The crystalline 2-[(ethyldithio) methyl]-4-methoxy-3-methyl-1-(5,6,7,8-tetrahydro-5,5,8,8-tetramethyl-1H -naphth[2,3-d]imidazol- 2-yl)pyridinium chloride obtained is filtered off and washed with cold ether; it exhibits a melting point of 160° (dec.).

EXAMPLE 130

1.84 ml of thiosalicylic acid are stirred in 100 ml of 20% alcoholic hydrochloric acid and treated with 2.6 g of 2-[(2-pyridylmethyl)sulphinyl]benzimidazole while cooling with ice. The mixture is stirred further at room temperature overnight and then suction filtered. The crystals are washed with ether and dried at 40° in vacuo. The crude product is recrystallized from alcohol/abs. ether. There is obtained 1-(2-benzimidazolyl)-2-[[(o-carboxyphenyl)dithio]methyl]pyridinium chloride of melting point 142°–145°.

EXAMPLE 131

2.6 g of 2-[(2-pyridylmethyl)sulphinyl]benzimidazole are placed in 50 ml of dioxan and 50 ml of 3N hydrochloric acid and treated with 2.02 g of dodecanethiol. After stirring at room temperature for 30 minutes the mixture is evaporated in vacuo. The residue is dissolved in alcohol and, after the addition of toluene, again evaporated, then brought to crystallization with ether, filtered off under suction and washed with ether. There is obtained 1-(2-benzimidazolyl)-2-[(dodecyldithio)methyl]pyridinium chloride of melting point 117°–120°.

EXAMPLE 132

1.18 g of 1-hexanethiol are placed in 30 ml of methanol and 70 ml of 3N hydrochloric acid and treated while cooling with ice at between 5°–10° with 2.6 g of 2-[(2-pyridylmethyl)sulphinyl]benzimidazole. The mixture is stirred at 5°–10° for 3 hours and then, after adding 30 ml of 3N hydrochloric acid, at room temperature for a further 1.5 hours and subsequently evaporated at 20° in a high vacuum. After crystallization from ethyl acetate/abs. ether the residue gives 1-(2-benzimidazolyl)-2-[(hexyldithio)methyl]pyridinium chloride of melting point 125°–127°.

EXAMPLE 133

1.0 g of 2-mercaptoethanol are placed in 30 ml of methanol and 70 ml of 3N hydrochloric acid and treated while cooling with ice at between 5°–10° with 2.6 g of 2-[(2-pyridylmethyl)sulphinyl]benzimidazole. The mixture is stirred at 5°–10° for 3 hours and then, after adding 30 ml of 3N hydrochloric acid, at room temperature for a further 1.5 hours and subsequently evaporated at 20° in a high vacuum. After crystallization from methanol/abs. ether the residue gives 1-(2-benzimidazolyl)-2-[[(2-hydroxyethyl)dithio]methyl]pyridinium chloride of melting point 130°–132°.

EXAMPLE 134

0.7 ml of tert.butyl mercaptan are placed in 30 ml of methanol and 70 ml of 3N hydrochloric acid and treated while cooling with ice at between 5°–10° with 2.6 g of 2-[(2-pyridylmethyl)sulphinyl]benzimidazole. The mixture is stirred at 5°–10° for 3 hours and then, after adding 30 ml of 3N hydrochloric acid, at room temperature for a further 1.5 hours and subseguently evaporated at 20° in a high vacuum. After crystallization from methanol/abs. ether the residue gives 1-(2-benzimidazolyl)-2-[(2-tert. butyldithio]methyl]pyridinium chloride of melting point 192°–194°.

EXAMPLE 135

2.6 g of 2-[(2-pyridylmethyl)sulphinyl]benzimidazole are placed in 250 ml of 20% alcoholic hydrochloric acid. 1.24 g of p-thiocresol in 50 ml of alcohol are added dropwise thereto. The mixture is stirred at room temperature for 2 hours and then suction filtered. The filtrate is evaporated in vacuo and the residue is crystallized from alcohol/ether. There is obtained 1-(2-benzimidazolyl)-2-[(p-tolyldithio)methyl]pyridinium chloride of melting point 124°–126°.

EXAMPLE 136

2.6 g of 2-[(2-pyridylmethyl)sulphinyl]benzimidazole are dissolved in 30 ml of tetrahydrofuran and treated with 1.0 ml of n-propyl mercaptan. 10 ml of 3N hydrochloric acid are added at an internal temperature of 40°. The mixture is stirred at 40° for 5 minutes and then evaporated in vacuo. The residue is crystallized from ethanol/ether. There is obtained 1-(2-benzimidazolyl)-2-[(propyldithio)methyl]pyridinium chloride of melting point 144°–145°.

EXAMPLE 137

2.6 g of 2-[(2-pyridylmethyl)sulphinyl]benzimidazole are dissolved in 30 ml of tetrahydrofuran and treated with 1.5 g of thiomalic acid. 10 ml of 3N hydrochloric acid are added at an internal temperature of 40°. After stirring at 40° tor 5 minutes the mixture is evaporated in vacuo. The residue is crystallized from methanol/tert.butyl methyl ether/ethyl acetate. There is obtained 1-(2-benzimidazolyl)-2-[[(1,2-dicarboxyethyl)dithio]methyl]pyridinium chloride of melting point 113°–115°.

EXAMPLE 138

2.6 g of 2-[(2-pyridylmethyl)sulphinyl]benzimidazole are dissolved in 50 ml of acetonitrile and treated with 1.0 ml of ethyl mercaptan. 50 ml of 3N hydrochloric acid are added at an internal temperature of 40°. The mixture is stirred at room temperature overnight and then evaporated in vacuo. The residue is crystallized from methanol/abs. ether and there is obtained 1-(2-benzimidazolyl)-2-[(ethyldithio)methyl]pyridinium chloride of melting point 113°–115°.

EXAMPLE 139

(a) 64.8 g of 2-benzimidazolethiol are suspended in 400 ml of alcohol and treated with 95.9 g of 2-chloromethyl-4-methoxy-3.5-dimethylpyridine hyrochloride while cooling with ice. Thereafter, a solution of 34.5 g of sodium hydroxide in 1.5 l of water is added dropwise thereto, the mixture is left to boil at reflux overnight and subsequently evaporated to dryness in vacuo. The residue is dissolved in 2.0 l of methylene chloride. The solution is washed firstly with 600 ml of 1.5N sodium hydroxide solution and then 3× with 2.2 l of water, dried over sodium sulphate and evaporated in vacuo. The crude product is purified on 1300 g of silica gel with ethyl acetate/methylene chloride (1:1) as the elution agent. Crystallization from methylene chloride/petroleum ether gives 2-[[(4-methoxy-3,5 -dimethyl-2-pyridyl)methyl]thio]benzimidazole of melting point 129°–131°.

(b) 53.5 g of 2-[[(4-methoxy-3,5-dimethyl-2 -pyridyl)methyl]thio]benzimidazole are dissolved in 1.2 l of methylene chloride and 100 ml of methanol and then cooled to −20°. 33.4 g of m-chloroperbenzoic acid, recrystallized from methylene chloride/petroleum ether, are then introduced within 10 minutes. The solution is stirred for a further 60 minutes at −20° and then poured into a mixture of 250 ml of 2N sodium carbonate solution and ice. The organic phase is washed neutral with water, dried over sodium sulphate and evaporated in vacuo. Crystallization from methylene chloride/methanol/petroleum ether gives 2-[[(4-methoxy-3,5-dimethyl-2-pyridyl)methyl]sulphinyl]benzimidazole of melting point 157°–159°.

(c) 3.15 g of 2-[[(4-methoxy-3,5-dimethyl-2-pyridyl)methyl]sulphinyl]benzimidazole are dissolved in 30 ml of tetrahydrofuran at 40°, treated with 1 ml of n-propyl mercaptan and with 10 ml of 3N hydrochloric acid and stirred for 5 minutes. The mixture is subsequently evaporated in vacuo. The residue is crystallized from methanol/ether and there is obtained 1-(2-benzimidazolyl)-4-methoxy-3,5-dimethyl-2-[(propyldithio)methyl]-pyridinium chloride of melting point 175°–177°.

EXAMPLE 140

2.6 g of thiosalicylic acid in 50 ml of 20% alcoholic hydrochloric acid are treated with 2.6 g of 2-[[(4-methoxy-3-methyl-2-pyridyl)methyl]sulphinyl]-5-(trifluoromethyl)benzimidazole while stirring. The mixture is stirred at room temperature overnight, then suction filtered and the residue is washed with abs. ether. Crystallization from alcohol/abs. ether gives 2-[[(o-carboxyphenyl)dithio]methyl]-4-methoxy-3-methyl-1-[5-(trifluoromethyl)-2-benzimidazolyl]pyridinium chloride of melting point 180°–182°.

EXAMPLE 141

2.48 g of p-thiocresol are placed in 10 ml of alcohol and treated with 3.69 g of 2-[[(4-methoxy-3-methyl-2-pyridyl)methyl]sulphinyl]-5-(trifluoromethyl)benzimidazole. 50 ml of 20% alcoholic hydrochloric acid are added dropwise thereto while cooling with ice and stirring. The mixture is stirred at room temperature overnight, then, suction filtered and the residue is washed with abs. ether. Crystallization from alcohol/ether gives 4-methoxy-3-methyl-2-[(p-tolyldithio)methyl]-1-[5-(tri-fluoromethyl)-2-benzimidazolyl]-pyridinium chloride of melting point 138°–14°.

EXAMPLE 142

73.0 g of thiomalic acid are placed in 50 ml of alcohol and treated with 3.69 g of 2-[[(4-methoxy-3-methyl-2-pyridyl)methyl]sulphinyl]-5-(trifluoromethyl)benzimidazole. 50 ml of 20% alcoholic hydrochloric acid are added dropwise thereto while cooling with ice and stirring. The mixture is stirred at room temperature overnight and then evaporated at 20° in a high vacuum. Crystallization from alcohol/abs. ether gives 2-[[(1,2-bis-(ethoxycarbonyl)ethyl]dithio]methyl]-4-methoxy-3-methyl-1-[5-(trifluoromethyl)-2-benzimidazolyl]-pyridinium chloride of melting point 96°–97°.

EXAMPLE 143

2.2 g of 2-[[(4-methoxy-3-methyl-2-pyridyl)methyl]-sulphinyl]-5-(trifluoromethyl)benzimidazole are dissolved in 30 ml of tetrahydrofuran and treated with 0.6 ml of n-propyl mercaptan. 6 ml of 3N hydrochloric acid are added thereto at an internal temperature of 40°. After stirring for 5 minutes the mixture is evaporated in vacuo, the residue is dissolved in alcohol and the impurities are precipitated with ether. The solution is filtered and the filtrate is evaporated in vacuo. The residue is crystallized from tert.butyl methyl ether/ether and there is obtained 2-[(propyldithio)methyl]-4-methoxy-3-methyl-1-[5-(trifluoromethyl)-2-benzimidazolyl]-pyridinium chloride of melting point 152°–153°.

EXAMPLE 144

3.69 g of 2-[[(4-methoxy-3-methyl-2-pyridyl)methyl]-sulphinyl]-5-(trifluoromethyl)benzimidazole are dissolved in 50 ml of acetonitrile and treated with 1.5 g of thiomalic acid. 50 ml of 3N hydrochloric acid are added at an internal temperature of 40° and the mixture is stirred further at room temperature overnight and subsequently evaporated in vacuo. The residue is crystallized from abs. ether and there is obtained 2-[[(1,2-dicarboxyethyl)dithio]methyl]-4-methoxy-3-methyl-1-[5-(trifluoromethyl)-2-benzimidazolyl]pyridinium chloride of melting point 110°–115°.

EXAMPLE 145

5.16 g of 2-[[(4-methoxy-3-methyl-2-pyridyl)methyl]-sulphinyl]-5-(trifluoromethyl)benzimidazole are dissolved in 100 ml of methanol and treated with 1.65 g of hexanethiol. 85 ml of 3N hydrochloric acid are added at an internal temperature of 40°. The mixture is stirred at this temperature for 15 minutes; it is then evaporated in vacuo. Crystallization from tert.butyl methyl ether/ether gives a product of melting point 130°–132° which is recrystallized from ethyl acetate/ether/petroleum ether (low-boiling) and then melts at 116°–118°. Repeated recrystallization from alcohol/ether gives 2-[(hexyldithio)methyl]-4-methoxy-3-methyl-1-[5-(trifluoromethyl)-2-benzimidazolyl]pyridinium chloride of melting point 124°–125°.

EXAMPLE 146

3.69 g of 2-[[(4-methoxy-3-methyl-2-pyridyl)methyl]-sulphinyl]-5-(trifluoromethyl)benzimidazole are dissolved in 60 ml of tetrahydrofuran and treated with 1.44 g of 2-chlorothiophenol. 12 ml of 3N hydrochloric acid are added at an internal temperature of 40°. The mixture is stirred at 40° for 5 minutes and then at room temperature for 1 hour and subsequently evaporated in vacuo. The residue is recrystallized from methanol/ether and there is obtained 2-[[(o-chlorophenyl)dithio]methyl]-4-methoxy-3-methyl-1-[5-(trifluoromethyl)-2-benzimidazolyl]pyridinium chloride of melting point 148°–150°.

EXAMPLE 147

3.69 g of 2-[[(4-methoxy-3-methyl-2-pyridyl)methyl]-sulphinyl]-5-(trifluoromethyl)benzimidazole are dissolved in 100 ml of acetonitrile and treated with 1.44 g of 3-chlorothiophenol. A solution of 18 ml of 3N hydrochloric acid and 18 ml of methanol is added thereto at 55° and the mixture is stirred further for 10 minutes. After evaporation in vacuo the residue is crystallized from methanol/ethyl acetate/abs. ether. There is obtained 2-[[(m-chlorophenyl)dithio]methyl]-4-methoxy-3-methyl-1-[5-(trifluoromethyl)-2-benzimidazolyl]-pyridinium chloride of melting point 76°–80°.

EXAMPLE 148

3.69 g of 2-[[(4-methoxy-3-methyl-2-pyridyl)methyl]-sulphinyl]-5-(trifluoromethyl)benzimidazole are dissolved in 100 ml of acetonitrile and treated with 1.12 g of 2-pyrimidinethiol. A solution of 18 ml of 3N hydrochloric acid and 18 ml of methanol is added thereto at 55° and the mixture is stirred further at this temperature for 10 minutes. After evaporation in vacuo the residue is crystallized from tert.butyl methyl ether. There is obtained 4-methoxy-3-methyl-1-[5-(trifluoromethyl)-2-benzimidazolyl]-2-[(2-pyrimidinyldithio)methyl]-pyridinium chloride of melting point 95°–100°.

EXAMPLE 149

3.69 g of 2-[[(4-methoxy-3-methyl-2-pyridyl)methyl]-sulphinyl]-5-(trifluoromethyl)benzimidazole are dissolved 50 ml of tetrahydrofuran and treated with 1.21 g of L-cysteine. 20 ml of 3% hydrochloric acid are added at an internal temperature of 40° and stirred for 10 minutes. After evaporation in vacuo the residue is crystallized from tert.butyl methyl ether/ether. There is obtained 2-[[[(R)-2-amino-2-carboxyethyl]dithio]methyl]-4-methoxy-3-methyl-1-[5-(trifluoromethyl)-2-benzimidazolyl]pyridinium chloride of melting point 168°–170°.

EXAMPLE 150

3.69 g of 2-[[(4-methoxy-3-methyl-2-pyridyl)methyl]-sulphinyl]-5-(trifluoromethyl)benzimidazole are dissolved in 50 ml of tetrahydrofuran and treated with 1 ml of ethyl mercaptan. 12 ml of 3N hydrochloric acid are added at an internal temperature of 40°. After stirring at 40° for 10 minutes the mixture is evaporated in vacuo. The foamy residue is stirred in tert.butyl methyl ether in vacuo for several hours, whereby a crystalline mass precipitates. There is obtained 2-[(ethyldithio)methyl]-4-methoxy-3-methyl-1-[5-(trifluoromethyl)-2-benzimidazolyl]pyridinium chloride of melting point 130°–132°.

EXAMPLE 151

3.69 g of 2-[[(4-methoxy-3-methyl-2 -pyridyl)methyl]-sulphinyl]-5-(trifluoromethyl)benzimidaZole are dissolved in 50 ml of tetrahydrofuran and treated With 0.8 ml of 2-mercaptoethanol. 20 ml of 3N hydrochloric acid are added at an internal temperature of 40°. After stirring at 40° for 10 minutes the mixture is evaporated in vacuo. The foamy residue is stirred overnight in tert.butyl methyl ether/abs. ether. There is obtained 2-[[(2-hydroxyethyl)dithio]methyl]-4 -methoxy-3-methyl-1-[5-(trifluoromethyl)-2-benzimidazolyl]pyridinium chloride of melting point 55°–60°.

EXAMPLE 152

3.69 g of 2-[[(4-methoxy-3-methyl-2-pyridyl)methyl]-sulphinyl]-5-(trifluoromethyl)benzimidazole are dissolved in 5ml of tetrahydrofuran and treated With 3.07 g of L-glutathione. 25 ml of 3N hydrochloric acid are added at an internal temperature of 40°. The mixture is stirred at 40° for 10 minutes and then evaporated in vacuo. The residue is crystallized from tert.butyl methyl ether/abs. ether. There is obtained 2-[[[(R)-2-[(S)-4-amino-4-carboxybutyramido]-2-[(carboxymethyl)carbamoyl]ethyl]dithio]methyl]-4 -methoxy-3-methyl-1 -[5-(trifluoromethyl)-2-benzimidazolyl]-pyridinium chloride of melting point 95°–100°.

EXAMPLE 153

3.69 g of 2-[[(4-methoxy-3-methyl-2-pyridyl)methyl]-sulphinyl]-5-(trifluoromethyl)benzimidazole are dissolved in 50 ml of tetrahydrofuran and treated with 0.92 g of thioglycolic acid. 20 ml of 3N hydrochloric acid are added at an internal temperature of 40°. The mixture is stirred at 40° for 10 minutes and then evaporated in vacuo. The residue is crystallized from tert.butyl methyl ether and there is obtained 2-[[[(carboxymethyl)dithio]methyl]-4-methoxy-3-methyl-1-(5-(trifluoromethyl)-2-benzimidazolyl)pyridinium chloride of melting point 105°–110°.

EXAMPLE 154

3.69 g of 2-[[(4-methoxy-3-methyl-2-pyridyl)methyl]-sulphinyl]-5-(trifluoromethyl)benzimidazole are dissolved in 50 ml of tetrahydrofuran and treated with 0.77 g of cysteamine. 25 ml of 3N hydrochloric acid are added at an internal temperature of 40°. The mixture is stirred at 40° for 10 minutes and then evaporated in vacuo. The residue is crystallized from tert.butyl methyl ether. There is obtained 2-[[(2-aminoethyl)dithio]methyl]-4-methoxy-3-methyl-1-[5-(trifluoromethyl)-2-benzimidazolyl]pyridinium chloride of melting point 105°–110°.

EXAMPLE 155

3.69 g of 2-[[(4-methoxy-3-methyl-2-pyridyl)methyl]-sulphinyl]-5-(trifluoromethyl)benzimidazole are dissolved in 50 ml of tetrahydrofuran and treated with 1.20 g of ethyl thioglycolate. 25 ml of 3N hydrochloric acid are added at an internal temperature of 40°. The mixture is stirred at 40° and then evaporated in vacuo. The residue is crystallized from tert.butyl methyl ether/abs. ether. There is obtained 2-[[[(ethoxycarbonyl)methyl]-dithio]methyl]-4-methoxy-3-methyl-1-[5-(trifluoromethyl)-2-benzimidazolyl]pyridinium chloride of melting point 125°–130°.

EXAMPLE 156

(a) 21.8 g of 5-(trifluoromethyl)-2-benzimidazolethiol are suspended in 400 ml of alcohol and treated with 22.2 g of 2-chloromethyl-4-methoxy-3,5-dimethylpyridine hydrochloride while cooling with ice. Thereafter, a solution of 8.0 g of sodium hydroxide in 300 ml of water is added dropwise thereto, the mixture is left to boil at reflux overnight and subsequently evaporated to dryness in vacuo. The residue is dissolved in 1.5 l of methylene chloride. The solution is washed firstly with 200 ml of 1.5N sodium hydroxide solution and then 3 x with 700 ml of water, dried over sodium sulphate and evaporated in vacuo. The crude product is purified on 360 g of silica gel with ethyl acetate/methylene chloride (1:1) as the elution agent. Crystallization from methylene chloride/petroleum ether gives 2-[[(4-methoxy-3,5-dimethyl-2-pyridyl)methyl]thio]-5-(trifluoromethyl)-benzimidazole of melting point 164°–166°.

(b) 31.4 g of 2-[[(4-methoxy-3,5-dimethyl-2-pyridyl)-methyl]thio]-5-(trifluoromethyl)benzimidazole are dissolved in 1.3 l of methylene chloride and 50 ml of methanol and then cooled to −20°. 16.9 g of m-chloroperbenzoic acid, recrystallized from a methyene chloride/-petroleum ether, are then introduced within 10 minutes. The solution is stirred further at −20° for 60 minutes and then poured into a mixture of 120 ml of 2N sodium carbonate solution and ice. The organic phase is washed neutral with water, dried over sodium sulphate and evaporated in vacuo. Crystallization from methylene chloride/methanol/petroleum ether gives 2-[[(4-methoxy-3,5-dimethyl-2-pyridyl)methyl]sulphinyl]-5-(trifluoromethyl)benzimidazole of melting point 152°–154°.

(c) 3.83 g of 2-[[(4-methoxy-3,5-dimethyl-2-pyridyl)-methyl]sulphinyl]-5-(trifluoromethyl)benzimidazole are dissolved in 100 ml of acetonitrile and treated with 1.5 g of thiomalic acid. 25 ml of 3N hydrochoric acid are added dropwise thereto at 55°. The solution is stirred at this temperature for 10 minutes and then evaporated in vacuo. Crystallization from acetonitrile/abs. ether gives 2-[((1,2-dicarboxyethyl)dithio]methyl]-4-methoxy-3,5-dimethyl-1-[5-(trifluoromethyl)-2-benzimidazolyl]-pyridinium chloride of melting point 110°–115°.

EXAMPLE 157

(a) 6.54 g of 5-(trifluoromethyl)-2-benzimidazolethiol are suspended in 200 ml of alcohol and treated with 5.34 g of 2-chloromethyl-3-methylpyridine hydrochloride while cooling with ice. Thereafter. a solution of 2.4 g of sodium hydroxide in 100 ml of water is added dropwise thereto, the mixture is left to boil at reflux overnight and subsequently evaporated to dryness in vacuo. The residue is dissolved in 950 ml of methylene chloride. The solution is washed firstly with 200 ml of 1.5N sodium hydroxide solution and then 3 x with 250 ml of water. dried over sodium sulphate and evaporated in vacuo. The crude product is purified on 100 g of silica gel with ethyl acetate/methylene chloride (1:1) as the elution agent. Crystallization from methylene chloride/petroleum ether gives 2-[[3-methyl-2-pyridyl)methyl]thio]-5-(trifluoromethyl)benzimidazole of melting point 180°–182°.

(b) 6.7 g of 2-[[(3-methyl-2 -pyridyl)methyl]thio]-5-(trifluoromethyl)benzimidazole are dissolved in 250 ml of methylene chloride and 20 ml of methanol and then cooled to −20°. 4.7 g of m-chloroperbenzoic acid, recrystallized from methylene chloride/petroleum ether, are then introduced within 10 minutes. The solution is stirred further at −20° for 60 minutes and then poured into a mixture of 100 ml of 2N sodium carbonate solution and ice. The organic phase is washed neutral with water, dried over sodium sulphate and evaporated in vacuo. Crystallization from methylene chloride/methanol/petroleum ether gives 2-[[(3-methyl-2-pyridyl)-methyl]sulphinyl]-5 -(trifluoromethyl)benzimidazole of melting point 156°–158°.

(c) To 120 ml of 1N hydrochloric acid and 1.18 g of n-hexanethiol there are added firstly 3.39 g of 2-[[(3-methyl-2-pyridyl)methyl]sulphinyl]-5 -(trifluoromethyl)benzimidazole and then 60 ml of methanol. The mixture is stirred at room temperature for 12 hours and then evaporated in vacuo. The residue is crystallized from tert.butyl methyl ether/ether. There is obtained 2-[(hexyldithio)methyl]-3-methyl-1 -[5-(trifluoromethyl)-2-benzimidazolyl]pyridinium chloride of melting point 152°–153°.

EXAMPLE 158

3.39 g of 2-[[(3-methyl-2-pyridyl)methyl]sulphinyl]5 -(trifluoromethyl)benzimidazole are dissolved in 50 ml of tetrahydrofuran and treated With 1.21 g of L-cysteine. 40 ml of 3N hydrochloric acid are added at an internal temperature of 40°. After stirring at 4° for 5 minutes and at room temperature for 48 hours the mixture is evaporated in vacuo. The residue is crystallized from tert.butyl methyl ether/abs ether. There is obtained 2-[[(2-amino-2-carboxyethyl)dithio]methyl]-3-methyl-1-[5-(trifluoromethyl)-2-benzimidazolyl]-pyridinium chloride of melting point 116°–120°.

EXAMPLE 159

3.39 g of 2-[[(3-methyl-2 -pyridyl)methyl]sulphinyl]-5-(trifluoromethyl)benzimidazole are dissolved in 50 ml of tetrahydrofuran and treated with 1.0 ml of n-propyl mercaptan. 40 ml of 3N hydrochloric acid are added at an internal temperature of 40°. After stirring at 40° for 5 minutes 50 ml of methanol are added thereto and the mixture is stirred further at room temperature for 48 hours. The mixture is subsequently evaporated in vacuo. The residue is crystallized from tert.butyl methyl ether/abs. ether. There is obtained 2-[(propyldithio)methyl]-3-methyl-1-[5-(trifluoromethyl)-2-benzimidazolyl]pyridinium chloride of melting point 144°–146°.

EXAMPLE 160

3.39 g of 2-[[(3-methyl-2 -pyridyl)methyl]sulphinyl]-5-(trifluoromethyl)benzimidazole are dissolved in 50 ml of tetrahydrofuran and treated with 0.78 g of 2-mercaptoethanol. 20 ml of 3N hydrochloric acid are added at an internal temperature of 40°. After stirring at 40° for 10 minutes the mixture is evaporated in vacuo. The residue is crystallized from tert.butyl methyl ether. There is obtained 2-[[(2-hydroxyethyl)dithio]methyl]-3-methyl-1-[5-(trifluoromethyl)-2-benzimidazolyl]-pyridinium chloride of melting point 70°–75°.

EXAMPLE 161

3.39 g of 2-[[(3-methyl-2-pyridyl)methyl]sulphinyl]-5-(trifluoromethyl)benzimidazole are dissolved in 50 ml of tetrahydrofuran and treated With 1 ml of ethyl mercaptan. 40 ml of 3N hydrochloric acid are added at an internal temperature of 40°. After stirring at 40° for 5 minutes and at 20° for 1 hour 50 ml of methanol are added thereto, the mixture is stirred further at 20° for 24 hours and subsequently evaporated in vacuo. The residue is crystallized from tert.butyl methyl ether/abs. ether. There is obtained 2-[(ethyldithio)methyl]-3-methyl-1-[5-(trifluoromethyl)-2-benzimidazolyl]pyridinium chloride of melting point 142°–144°.

EXAMPLE 162

3.39 g of 2-[[(3-methyl-2-pyridyl)methyl]sulphinyl]-5-(trifluoromethyl)benzimidazole are dissolved in 50 ml of tetrahydrofuran and treated with 0.77 g of cysteamine. 40 ml of 3N hydrochloric acid are added at an internal temperature of 40°. After stirring at 40° for 10 minutes and at room temperature overnight the mixture is evaporated in vacuo. The residue is crystallized from tert.butyl methyl ether/ether. There is obtained 2-[[(2-aminoethyl)dithio]methyl]-3 -methyl-1-[5-(trifluoromethyl)-2-benzimidazolyl]pyridinium chloride of melting point 95°–100°.

EXAMPLE 163

3.39 g of 2-[[(3-methyl-2 -pyridyl)methyl]sulphinyl]-5-(trifluoromethyl)benzimidazole are dissolved in 200 ml of ethyl methyl ketone and treated with 1.20 g of ethyl thioglycolate. 30 ml of 1N hydrochloric acid are added at an internal temperature of 40°. After stirring at 40° for 10 minutes the mixture is evaporated in vacuo. The residue is crystallized from acetone/ether. There is obtained 2-[[[(ethoxycarbonyl)methyl]dithio]methyl]-3 -methyl-1-[5-(trifluoromethyl)-2-benzimidazolyl]-pyridinium chloride of melting point 144°–146°.

EXAMPLE 164

3.39 g of 2-[[(3-methyl-2 -pyridyl)methyl]sulphinyl]-5-(trifluoromethyl)benzimidazole are dissolved in 150 ml of tetrahydrofuran and treated with 0.92 g of thioglycolic acid. 20 ml of 3N hydrochloric acid are added at an internal temperature of 40°. After stirring at 40° overnight the mixture is evaporated in vacuo. The residue is crystallized from acetone/tert.butyl methyl ether/ether. There is obtained 2-[[(carboxymethyl)dithio]methyl]-3-[5-(trifluoromethyl)-2 -benzimidazolyl]-pyridinium chloride of melting point 110°-115°.

EXAMPLE 165

3.39 g of 2-[[(3-methyl-2 -pyridyl)methyl]sulphinyl]-5-(trifluoromethyl)benzimidazole are dissolved in 250 ml of ethyl methyl ketone and treated with 1.84 g of thiosalicylic acid. 90 ml of 3N hydrochloric acid are added at an internal temperature of 40°. After stirring at 40° for 10 minutes and at room temperature overnight the mixture is evaporated in vacuo. The residue is crystallized from tert.butyl methyl ether/ether. There is obtained 2-[[(o-tert.butyl-carboxyphenyl)dithio] methyl]-3-methyl-1-[5-(trifluoromethyl 2-benzimidazolyl]-pyridinium chloride of melting point 186°-188°.

EXAMPLE 166

3.39 g of 2-[[(3-methyl-2 -pyridyl)methyl]sulphinyl]-5-(trifluoromethyl)benzimidazole are dissolved in 250 ml of ethyl methyl ketone and treated with 1.5 g of thiomalic acid. 90 ml of 3N hydrochloric acid are added at an internal temperature of 40°. After stirring at 40° for 10 minutes and at room temperature overnight the mixture is evaporated in vacuo. The residue is crystallized from tert.butyl methyl ether/ether. There is obtained 2-[[(1,2-dicarboxyethyl)dithio]methyl]-3-methyl-1-[5-(trifluoromethyl)-2-benzimidazolyl]pyridinium chloride of melting point 115°-120°.

EXAMPLE 167

160 ml of 3N hydrochloric acid and 1.44 g of 2-chlorothiophenol are provided and treated with 3.39 g of 2-[[(3-methyl-2 -pyridyl)methyl]sulphinyl]-5-(trifluoromethyl)benzimidazole while cooling with ice/methanol. The mixture is then stirred at room temperature overnight and subsequently suction filtered, and the filter residue is washed with water. There is obtained 2-[[(o-chlorophenyl)dithio]methyl]-3-methyl-1-[5-(trifluoromethyl)-2-benzimidazolyl]pyridinium chloride of melting point 68°-70°.

EXAMPLE 168

160 ml of 3N hydrochloric acid and 1.12 g of 2-pyrimidinethiol are cooled with ice-methanol and treated with 3.39 g of 2-[[(3-methyl-2 -pyridyl)methyl]sulphinyl]-5-(trifluoromethyl)benzimidazole. The mixture is stirred at this temperature for 3 hours and then evaporated in vacuo. The residue is crystallized from tert.butyl methyl ether/ether. There is obtained 2-[(2-Pyrimidinyldithio)methyl]-3-methyl-1 -[5-(trifluoromethyl)-2-benzimidazolyl)pyridinium chloride of melting point 135°-140°.

EXAMPLE 169

120 ml of 1.5N hydrochloric acid and 1.44 g of 3-chlorothiophenol are cooled with ice/methanol, treated with 3.39 g of 2-[[(3-methyl-2-pyridyl)methyl]sulphinyl]-5-(trifluoromethyl)benzimidazole and stirred for 30 minutes. After adding 100 ml of 3N hydrochloric acid the mixture is stirred at room temperature overnight. After evaporation in vacuo the residue is crystallized from tert.butyl methyl ether/ether. There is obtained 2-[[(m-chlorophenyl) dithio]methyl)]-3 -methyl-1-[5-(trifluoromethyl)-2-benzimidazolyl]pyridinium chloride of melting point 70°-75°.

EXAMPLE 170

(a) 6.54 g of 5-(trifluoromethyl)-2-benzimidazolethiol are suspended in 400 ml of alcohol and treated with 5.76 g of 2-chloromethyl-3,5-dimethylpyridine hydrochloride while cooling with ice. Thereafter, a solution of 2.4 g of sodium hydroxide in 100 ml of water is added dropwise thereto, the mixture is left to boil at reflux overnight and subsequently evaporated to dryness in vacuo. The residue is dissolved in 800 ml of methylene choride. The solution is washed firstly with 200 ml of 1.5N sodium hydroxide solution and then 3×with 250 ml of water, dried over sodium sulphate and evaporated in vacuo. The crude product is purified on 110 g of silica gel with ethyl acetate/methylene chloride (1:1) as the elution agent. Crystallization from methylene chloride/petroleum ether gives 2-[[(3,5-dimethyl-2 -pyridyl)methyl]thio]-5-(trifluoromethyl)benzimidazole of melting point 137°-138°.

(b) 5.5 g of 2- [[(3,5-dimethyl-2-pyridyl)methyl]thio]-5-(trifluoromethyl)benzimidazole are dissolved in 200 ml of methylene chloride and 10 ml of methanol and then cooled to −20°. 4.0 g of m-chloroperbenzoic acid, recrystallized from methylene chloride/petroleum ether, are introduced within 10 minutes. The solution is stirred further at −20° for 60 minutes and then poured into a mixture of 200 ml of 2N sodium carbonate solution and ice. The organic phase is washed neutral with water, dried over sodium sulphate and evaporated in vacuo. Crystallization from methylene chloride/methanol/petroleum ether gives 2-[[(3,5-dimethyl-2-pyridyl)methyl]sulphinyl]-5-(trifluoromethyl)benzimidazole of melting point 166°-168°.

(c) 2.9 g of 2-[[(3,5-dimethyl-2 -pyridyl)methyl]sulphinyl]-5-trifluoromethyl)benzimidazole are dissolved in 50 ml of tetrahydrofuran and treated with 1 ml of n-propyl mercaptan. 10 ml of 3N hydrochloric acid are added thereto at an internal temperature of 40°. The mixture is stirred firstly at 40° for 10 minutes and then at room temperature overnight and subsequently evaporated in vacuo. The residue is crystallized from tert.butyl methyl ether/ether. There is obtained 2-[(propyldithio)methyl]-3,5-dimethyl-1-[5-(trifluoromethyl)-2-benzimidazolyl]Pyridinium chloride of melting point 110°-112°.

EXAMPLE 171

3.53 g of 2-[[(3,5-dimethyl-2-pyridyl)methyl]sulphinyl]-5 -(trifluoromethyl)benzimidazole are dissolved in 50 ml of tetrahydrofuran and treated with 1.18 g of n-hexanthiol. 40 ml of 3N hydrochloric acid are added thereto at an internal temperature of 40°. The mixture is stirred at 40° overnight and subsequently evaporated in vacuo. The residue is crystallized from tert.butyl methyl ether/ether. There is obtained 2-[(n-hexyldithio)methyl)-3,5-dimethyl-1-[5-(trifluoromethyl)-2-benzimidazolyl]pyridinium chloride of melting point 80°-85°.

EXAMPLE 172

3.53 g of 2-[[3,5-dimethyl-2-pyridyl)methyl]sulphinyl]-5-(trifluoromethyl)benzimidazole are dissolved in 50 ml of tetrahydrofuran and treated with 1.12 g of L-cysteine. 40 ml of 3N hydrochloric acid are added thereto at an internal temperature of 40°. The mixture is stirred firstly at 40° for 10 minutes and then at room temperature overnight and subsequently evaporated in vacuo. The residue is crystallized from tert.butyl methyl ether/ether. There is obtained 2-[[[(R)-2-amino-2-carboxyethyl]dithio]methyl]-3,5-dimethyl-1-[5-(trifluoromethyl)-2-benzimidazolyl]pyridinium chloride of melting point 148°–150°.

EXAMPLE 173

3.53 g of 2-[[(3,5-dimethyl-2-pyridyl)methyl]sulphinyl]-5-(trifluoromethyl)benzimidazole are dissolved in 50 ml of tetrahydrofuran and treated with 1.2 g of ethyl thioglycolate. 40 ml of 3N hydrochloric acid are added thereto at an internal temperature of 40°. The mixture is stirred at 40° overnight and subsequently evaporated in vacuo. The residue is crystallized from tert.butyl methyl ether/ether. There is obtained 2-[[[(carboxymethyl)dithio]methyl]-3,5-dimethyl-1-[5-(trifluoromethyl)-2-benzixdazolyl]pyridinium chloride of melting point 75°–80°.

EXAMPLE 174

3.53 g of 2-[[(3,5-dimethyl-2-pyridyl)methyl]sulphinyl]-5-(trifluoromethyl)benzimidazole are dissolved in 50 ml of tetrahydrofuran and treated with 0.77 g of cysteamine. 40 ml of 3N hydrochloric acid are added thereto at an internal temperature of 40°. The mixture is stirred at 40° overnight and subseguently evaporated in vacuo. The residue is crystallized from tert.butyl methyl ether/ether. There is obtained 2-[[(2-aminoethyl)dithio]methyl]-3,5-dimethyl-1-[5-(trifluoromethyl)-2-benzimidazolyl]pyridinium chloride of melting point 115°–120°.

EXAMPLE 175

3.53 g of 2-[[(3,5-dimethyl-2-pyridyl)methyl]sulpinyl]-5-(trifluoromethyl)benzimidazole are dissolved in 50 ml of tetrahydrofuran and treated with 1 ml of 2-mercaptoethanol. 40 ml of 3N hydrochloric acid are added thereto at an internal temperature of 40°. The mixture is stirred at 40° overnight and subsequently evaporated in vacuo. The residue is crystallized from acetone/ether. There is obtained 2-[[(2-hydroxyethyl)-dithio]methyl]-3,5-dimethyl-1-[5-(trifluoromethyl)-2-benzimidazolyl]pyridinium chloride of melting point 105°–110°.

EXAMPLE 176

3.53 g of 2-[[(3,5-dimethyl-2-pyridyl)methyl]sulhinyl]-5-(trifluoromethyl)benzimidazole are dissolved in 200 ml of tetrahydrofuran and treated with 1.84 g of thiosalicylic acid. 40 ml of 3N hydrochloric acid are added thereto at an internal temperature of 40°. The mixture is stirred firstly at 40° for 10 minutes and then at room temperature overnight and subsequently evaporated in vacuo. The residue is crystallized from tert.butyl methyl ether/ether. There is obtained 2-[[(o-carboxyphenyl)dithio]methyl]-3,5-dimethyl-1 [5-(trifluoromethyl)-2-benzimidazolyl]pyridinium chloride of melting point 165°–167°.

EXAMPLE 177

3.53 g of 2-[[(3,5-dimethyl-2-pyridyl)methyl]sulphinyl]-5-(trifluoromethyl)benzimidazole are dissolved in 200 ml of tetrahydrofuran and treated with 1.5 g of thiomalic acid. 40 ml of 3N hydrochloric acid are added thereto at an internal temperature of 40°. The mixture is stirred firstly at 40° for 10 minutes and then at room temperature overnight and subsequently evaporated in vacuo. The residue is crystallized from tert.butyl methyl ether/ether. There is obtained 2-[[(1,2-dicarboxyethyl)dithio]methyl]-3,5-dimethyl-1-[5-(trifluoromethyl)-2-benzimidazolyl]pyridinium chloride of melting point 140°–145°.

EXAMPLE 178

3.53 g of 2-[[(3,5-dimethyl-2-pyridyl)methyl sulphinyl]-5-(trifluoromethyl)benzimidazole are dissolved in 200 ml of tetrahydrofuran and treated with 1 ml of ethyl mercaptan. 40 ml of 3N hydrochloric acid are added thereto at an internal temperature of 40°. The mixture is stirred firstly at 40° for 10 minutes and then at room temperature overnight and subsequently evaporated in vacuo. The residue is crystallized from acetone/ether. There is obtained 2-[(ethyldithio)methyl]-3,5-dimethyl-1-[5-(trifluoromethyl)-2-benzimidazolyl]pyridinium chloride of melting point 134°–136°.

EXAMPLE 179

3.53 g of 2-[[(3,5-dimethyl-2-pyridyl)methyl]sulphinyl]-5-(trifluoromethyl)benzimidazole are dissolved in 200 ml of tetrahydrofuran and treated with 1.44 g of 3-chlorothiophenol. 40 ml of 3N hydrochloric acid are added thereto at an internal temperature of 40°. The mixture is stirred firstlY at 40° for 10 minutes and then at room temperature overnight and subsequently evaporated in vacuo. The residue is crystallized from tert.butyl methyl ether/ether. There is obtained 2-[[(m-chlorophenyl)dithio]methyl]-3,5-dimethyl-1-[5-(trifluoromethyl)-2-benzimidazolyl]pyridinium chloride of melting point 140°–145°.

EXAMPLE 180

3.53 g of 2-[[(3,5-dimethyl-2-pyridyl)methyl)sulphinyl]-5-(trifluoromethyl)benzimidazole are dissolved in 250 ml of ethyl methyl ketone and treated with 1.12 g of 2-pyrimidinethiol. The mixture is cooled with an ice/methanol bath and, after addinq 90 ml of 3N hydrochloric acid, stirred at this temperature for 2 hours. After evaporation in vacuo the residue is crystallized from acetone/ether. There is obtained 2-[(2-pyrimidinyldithio)methyl]-3,5-dimethyl-1-[5-(trifluoromethyl)-2-benzimidazolyl]pyridinium chloride of melting point 75°–80°.

EXAMPLE 181

160 ml of 3N hydrochloric acid and 1.44 g of 2-chlorothiophenol are cooled with ice/methanol and treated with 3.53 g of 2-[[(3.5-dimethyl-2-pyridyl)methyl]sulphiryl]-5-(trifluoromethyl)benzimidazole. The mixture is stirred at room temperature overnight and subsequently evaporated in vacuo. The residue is crystallized from tert.butyl methyl ether. There is obtained 2-[[(o-chlorophenyl)dithio]methyl]-3,5-dimethyl-1-[5-(trifluoromethyl)-2-benzimidazolyl]pyridinium chloride of melting point 153°–155°.

EXAMPLE 182

A solution of 0.794 g of N-(2-mercaptopropionyl)glycine in 10 ml of 1N aqueous hydrochloric acid is treated with 2 g of 5,7-dihydro-2-[[(4-methoxy-3-methyl-2-pyridyl)methyl]sulphinyl]-5,5,7,7-tetramethylindeno[5,6-d]imidazol-6(1H)-one. The clear solution is concentrated, the residue is dissolved in acetone, treated with ethyl acetate and cooled to about 5°, whereupon the crystalline product is filtered off and washed with cold ethyl acetate. The 2-[[[1-carboxymethyl)carbamoyl]ethyl]dithio]methyl]-4-methoxy-3-methyl-1-(1,5,6,7-tetrahydro-5,5,7,7-tetramethyl-6- oxoindeno[5,6-d]imidazol-2-yl)pyridinium chloride obtained exhibits a melting point of 172° (dec.).

EXAMPLE A

Crystalline compounds of formula 1 can be used as the active substance for the manufacture of hard gelatine capsules, the content of which has the following composition per capsule:

| | |
|---|---|
| Active substance | 50.0 mg |
| Lactose powder | 40.0 mg |
| Lactose crystals | 130.0 mg |
| Maize starch white | 20.0 mg |
| Talc | 8.0 mg |
| Magnesium stearate | 2.0 mg |
| Fill weight per capsule | 250.0 mg |

The active substance and the adjuvants are mixed with one another and the mixture is filled into hard gelatine capsules of suitable size. If required, the capsules are subsequently provided with a gastric juice-resistant coating consisting of hydroxypropylmethylcellulose phthalate.

We claim:

1. A compound of the formula

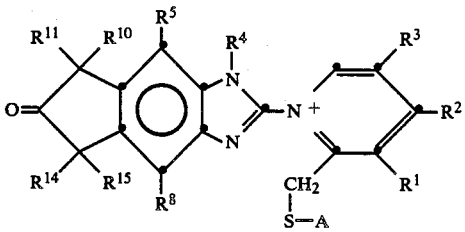

I wherein A is $-SR^9$, $-SO_3^-$ or $-S-SO_3^-$; $R^1$ and $R^3$ each is hydrogen or $(C_1-C_7)$-alkyl; $R^2$ is hydrogen, $(C_1-C_7)$-alkyl, $(C_1-C_7)$-alkoxy or a negatively charged oxygen atom; $R^4$ is hydrogen or a negative charge; $R^5$ and $R^8$ each is aryl, arylcarbonyl, aryloxycarbonyl, aryl-$(C_1-C_7)$-alkoxycarbonyl, aryloxy, arylcarbonyloxy, aryl-$(C_1-C_7)$-alkoxycarbonyloxy or aryloxycarbonyloxy, wherein aryl is phenyl or phenyl substituted by substituents selected from the group consisting of halogen, trifluoromethyl, nitro, $(C_1-C_7)$-alkyl, carboxy, $(C_1-C_7)$-alkoxycarbonyl, amino, amino monosubstituted by $(C_1-C_7)$-alkyl or $(C_1-C_7)$-alkanoyl or amino substituted by two $(C_1-C_7)$-alkyl groups; hydrogen, $(C_1-C_7)$-alkyl, halogen, cyano, nitro, formyl, $(C_1-C_7)$-alkanoyl, carboxy, carboxy-$(C_1-C_7)$-alkyl, $(C_1-C_7)$-alkoxycarbonyl, $(C_1-C_7)$-alkoxycarbonyl-$(C_1-C_7)$-alkyl, carbamoyl, mono- or di-$(C_1-C_7)$-alkylcarbamoyl, pyrrolidinocarbonyl, piperidinocarbonyl, carbamoyl-$(C_1-C_7)$-alkyl, mono- or di-$(C_1-C_7)$-alkylcarbamoyl-$(C_1-C_7)$-alkyl, pyrrolidinocarbonyl-$(C_1-C_7)$-alkyl, piperidino-carbonyl-$(C_1-C_7)$-alkyl, hydroxy, $(C_1-C_7)$-alkoxy, $(C_2-C_7)$-alkanoyloxy, $(C_1-C_7)$-alkoxycarbonyloxy, carbamoyloxy, mono- or di-$(C_1-C_7)$-alkyl-carbamoyloxy, pyrrolidinocarbonyloxy, piperidinocarbonyloxy, hydroxy-$(C_1-C_7)$-alkyl, trifluoromethyl, di-$(C_1-C_7)$-alkoxymethyl or $(C_2-C_3)$-alkylenedioxymethyl and $R^{10}$, $R^{11}$, $R^{14}$ and $R^{15}$ each is $(C_1-C_7)$-alkyl; and $R^9$ is $(C_1-C_{20})$-alkyl, $(C_3-C_7)$-cycloalkyl, $(C_3-C_7)$-alkenylalkyl, $(C_3-C_7)$-alkynylalkyl, $(C_3-C_7)$-alkenylalkyl which is substututed vinylically by halogen; aryl or aryl-$(C_1-C_7)$-alkyl wherein aryl is phenyl or phenyl substituted by substituents selected from the group consisting of halogen, trifluoromethyl, nitro, $(C_1-C_7)$-alkyl, carboxy, $(C_1-C_7)$-alkoxycarbonyl, amino, mono-substituted by $(C_1-C_7)$-alkyl or $(C_1-C_7)$-alkanoyl, amino disubstituted by $(C_1-C_7)$-alkyl and $(C_1-C_7)$-alkanoyl or amino substituted by two $(C_1-C_7)$-alkyl groups; hydroxy-$(C_2-C_7)$-alkyl, $(C_1-C_7)$-alkoxy-$(C_2-C_7)$-alkyl, $(C_1-C_7)$-alkoxycarbonyl-$(C_1-C_7)$-alkyl, carboxy-$(C_1-C_7)$-alkyl, di-$(C_1-C_7)$-alkoxycarbonyl-$(C_2-C_7)$-alkyl, dicarboxy-$(C_2-C_7)$-alkyl, carboxy-$(C_1-C_7)$-alkylcarbamoyl-$(C_1-C_7)$-alkyl, carboxy-$(C_1-C_7)$-alkylcarbamoyl-$(C_1-C_7)$-alkyl, amino-$(C_2-C_7)$-alkyl, amino-$(C_2-C_7)$-alkyl which is mono-sustituted by $(C_1-C_7)$-alkyl or $(C_1-C_7)$-alkanoyl or amino-$(C_2-C_7)$-alkyl which is di-substituted by $(C_1-C_7)$-alkyl and $(C_1-C_7)$-alkanoyl or by two $(C_1-C_7)$-alkyl groups, amino-carboxy-$(C_2-C_7)$-alkyl, amino-carboxy-$(C_2-C_7)$-alkyl which is mono-substituted by $(C_1-C_7)$-alkyl or $(C_1-C_7)$-alkanoyl or amino-carboxy-$(C_2-C_7)$-alkyl which is di-substituted by $(C_1-C_7)$-alkyl and $(C_1-C_7)$-alkanoyl or by two $(C_1-C_7)$-alkyl groups, or amino-$(C_1-C_7)$-alkoxycarbonyl-$(C_2-C_7)$-alkyl, amino-$(C_1-C_7)$-alkoxycarbonyl-$(C_2-C_7)$-alkyl which is mono-substituted by $(C_1-C_7)$-alkyl or $(C_1-C_7)$-alkanoyl or amino-$(C_1-C_7)$-alkoxycarbonyl-$(C_2-C_7)$-alkyl which is di-substituted by $(C_1-C_7)$-alkyl and $(C_1-C_7)$-alkanoyl or by two $(C_1-C_7)$-alkyl groups, whereby the compound is non-charged or has a net single positive charge provided that when there is a net single positive charge there is an external anion, or a pharmaceutically acceptable acid addition salt thereof.

2. A compound in accordance with claim 1, wherein A is $-SO_3^-$, $-S-SO_3^-$ or $-SR^9$ wherein $R^9$ is $(C_1-C_{20})$-alkyl, $(C_3-C_7)$-cycloalkyl, $(C_3-C_7)$-alkenylalkyl, $(C_3-C_7)$-alkynylalkyl, $(C_3-C_7)$-alkenylalkyl which is substituted vinylically by halogen; aryl or aryl-$(C_1-C_7)$-alkyl wherein aryl is phenyl or phenyl substituted by substituents selected from the group consisting of halogen, trifluoromethyl, nitro, $(C_1-C_7)$-alkyl, carboxy, $(C_1-C_7)$-alkoxycarbonyl, amino, amino monosubstituted by $(C_1-C_7)$-alkyl or $(C_1-C_7)$-alkanoyl, amino disubstituted by $(C_1-C_7)$-alkyl and $(C_1-C_7)$-alkanoyl, or amino substituted by two $(C_1-C_7)$-alkyl groups; hydroxy-$(C_2-C_7)$-alkyl, $(C_1-C_7)$-alkoxy-$(C_2-C_7)$-alkyl, $(C_1-C_7)$-alkoxycarbonyl-$(C_1-C_7)$-alkyl, carboxy-$(C_1-C_7)$-alkyl, di-$(C_1-C_7)$-alkoxycarbonyl-$(C_2-C_7)$-alkyl, dicarboxy-$(C_2-C_7)$-alkyl, amino-$(C_2-C_7)$-alkyl, amino-$(C_2-C_7)$-alkyl which is mono-substituted by $(C_1-C_7)$-alkyl or $(C_1-C_7)$-alkanoyl or is di-substituted by $(C_1-C_7)$-alkyl and $(C_1-C_7)$-alkanoyl or by two $(C_1-C_7)$-alkyl residues, amino-carboxy-$(C_2-C_7)$-alkyl, amino-carboxy-$(C_2-C_7)$-alkyl which is mono-substituted by $(C_1-C_7)$-alkyl or $(C_1-C_7)$-alkanoyl or is di-substituted by $(C_1-C_7)$-alkyl and $(C_1-C_7)$-alkanoyl or by two $(C_1-C_7)$-alkyl residues, amino-$(C_1-C_7)$-alkoxycarbonyl-$(C_2-C_7)$-alkyl, amino-$(C_1-C_7)$-alkoxycarbonyl-$(C_2-C_7)$-alkyl which is mono-substituted by $(C_1-C_7)$-alkyl or $(C_1-C_7)$-alkanoyl or is disubstituted by $(C_1-C_7)$-alkyl and $(C_1-C_7)$-alkanoyl or by two $(C_1-C_7)$-alkyl residues.

3. A compound in accordance with claim 2, wherein $R^5$ and $R^8$ each is hydrogen.

4. A compound in accordance with claim 1 wherein $R^{10}$, $R^{11}$, $R^{14}$ and $R^{15}$ all are methyl.

5. A compound in accordance with claim 1, wherein $R_1$ is hydrogen or methyl.

6. A compound in accordance with claim 1, wherein $R^2$ is hydrogen, methyl, t-butyl, methoxy, ethoxy, n-propoxy or a negatively charged oxygen atom.

7. A compound in accordance with claim 1, wherein $R^3$ is hydrogen or methyl.

8. A compound in accordance with claim 2, wherein A is $-SR^9$ and $R^9$ is methyl, ethyl, n-propyl, i-propyl, s-butyl, t-butyl, n-pentyl, n-hexyl, n-dodecyl, n-hexadecyl, n-octadecyl, allyl, cyclopentyl, 2-hydroxyethyl, methoxycarbonylmethyl, 1,2-dicarboxyethyl, 2-carboxyethyl, 1-carboxyethyl, 2-amino-2-carboxyethyl, 2-amino-2-ethoxycarbonylethyl, 3-amino-3-carboxypropyl, 2-(4-amino-4-carboxybutyramido)-2-(carboxymethyl-carbamoyl)ethyl, phenyl, p-tolyl, m-chlorophenyl, o-carboxyphenyl, p-fluorophenyl, p-chlorophenyl, m-methoxyphenyl, pentafluorophenyl, benzyl, triphenylmethyl, or 2-dimethylaminoethyl or wherein A is $-SO_3^-$ or $-S-SO_3^-$.

9. A compound in accordance with claim 1, wherein A is $-SR^9$ and $R^9$ is n-octyl, t-octyl, cyclohexyl, 2-chloroallyl, o-tolyl, o-chlorophenyl, m-fluorophenyl, p-methoxyphenyl, o-methoxyphenyl, 2,6-dichlorophenyl, 2,5-dichlorophenyl, 2,3-dichlorophenyl, 2,4-dichlorophenyl, 3,4-dichlorophenyl, o-methoxycarbonylphenyl, p-nitrophenyl, m-bromophenyl, p-bromophenyl, m-aminophenyl, o-aminophenyl, p-acetylaminophenyl, m-trifluoromethylphenyl, o-nitrobenzyl, p-fluorobenzyl, p-methoxybenzyl, m-trifluoromethylbenzyl, 2-phenylethyl, o-chlorobenzyl, p-chlorobenzyl, m-nitrobenzyl, 3,4-dichlorobenzyl, 2,4-dichlorobenzyl, ethoxycarbonylmethyl, carboxymethyl, 1,2-bis-(ethoxycarbonyl)ethyl, 2-amino-2-carboxy-1,1-dimethylethyl, 2-aminoethyl or 1-[(carboxymethyl)-carbamoyl]ethyl.

10. A compound in accordance with claim 1, wherein $R^1$ is $(C_1-C_7)$-alkyl, $R^2$ is $(C_1-C_7)$-alkoxy, $R^3$ is hydrogen or $(C_1-C_7)$-alkyl, A is $-SR^9$, $R^9$ is n-propyl, 2-amino-2-carboxyethyl, 2-(4-amino-4-carboxybutyramido)-2-(carboxymethylcarbamoyl)ethyl, n-hexyl, o-chlorophenyl, ethyl, 2-aminoethyl, m-chlorophenyl, 1,2-bis-(ethoxycarbonyl)ethyl, 2-amino-2-ethoxycarbonylethyl, 2-hydroxyethyl, 3-amino-3-carboxypropyl, cyclopentyl, 2-dimethylaminoethyl, o-carboxyphenyl, isopropyl, p-fluorophenyl, 2-carboxyethyl, 1-carboxyethyl, p-chlorophenyl, n-pentyl, 2-chloroallyl, o-nitrobenzyl, 3,4-dichlorophenyl, p-methoxyphenyl, 10[(carboxymethyl)carbamoyl]-ethyl or o-chlorophenyl, $R^5$ and $R^8$ each is hydrogen.

11. A compound in accordance with claim 10, wherein $R^1$ is methyl, $R^2$ is methoxy and $R^3$ is hydrogen or methyl and $R^{10}$, $R^{11}$, $R^{14}$ and $R^{15}$ all are methyl.

12. A compound in accordance with claim 1, 2-[[(m-Chlorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride.

13. A compound in accordance with claim 1, 2-[[[(R)-2-Amino-2-carboxyethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride.

14. A compound in accordance with claim 1. 2-[(Ethyldithio)methyl]-4-methoxy-3-methyl-1-(1,5,6,7-tetrahydro-5,5,7,7-tetramethyl-6-oxoindeno[5,6-d]-imidazol-2-yl)pyridinium chloride.

15. A compound in accordance with claim 1, 4-Methoxy-3-methyl-2-[(propyldithio)methyl]-1-(1,5,6,7-tetrahydro-5,5,7,7-tetramethyl-6-oxoindeno[5,6-d]-imidazol-2-yl)pyridinium chloride.

16. A compound in accordance with claim 1, 2-[[[(R)-2-Amino-2-(ethoxycarbonyl)ethyl]dithio] methyl]-4-methoxy-3-methyl-1-(1,5,6,7-tetrahydro-5,5,7,7-tetramethyl-6-oxondeno[5,6-d]imidazol-2-yl)pyridinium chloride.

17. A compound in accordance with claim 1, Intramolecularly deprotonize 2-[[2-(dimethylaminoethyl]dithio]methyl]-4-methoxy-3-methyl-1-(1,5,6,7-tetrahydro-5,5,7,7-tetramethyl-6-oxoindeno[5,6-d]imidazol-2-yl)pyridinium cation.

18. A compound in accordance with claim 1, 2-[[(2-Hydroxyethyl)dithio)methyl)-4-methoxy-3-methyl-1-(1,5,6,7-tetrahydro-5,5,7,7-tetramethyl-6-oxoindeno[5,6-d]imidazol-2-yl)pyridinium chloride.

19. A compound in accordance with claim 1, 2-[[[(RS)-3-Amino-3-carboxypropyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride.

20. A compound in accordance with claim 1, 2-[(Cyclopentyldithio)methyl]-4-methoxy-3-methyl-1-(1,5,6,7-tetrahydro-5,5,7,7-tetramethyl-6-oxoindeno[5,6-d]imidazol-2-yl)pyridinium chloride.

21. A compound in accordance with claim 1 selected from the group consisting of

2-[[(o-Carboxyphenyl)dithio]methyl]-4-methoxy-3-methyl-1-(1,5,6,7-tetrahydro-5,5,7,7-tetramethyl-6-oxoindeno[[5,6-d]imidazol-2-yl)pyridinium chloride;

2-[(2-isopropyldithio)methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[(p-fluorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[(2-carboxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[(1-carboxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[(p-chlorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[(hexyldithio)methyl]-4-methoxy-3-methyl-1-(1,5,6,7-tetrahydro-5,5,7,7-tetramethyl-6-oxoindeno[5,6-d]imidazol-2-yl)pyridinium chloride;

4-methoxy-3-methyl-2-[(pentyldithio)methyl]-1-(1,5,6,7-tetrahydro-5,5,7,7-tetramethyl-6-oxoindeno 5,6-d]imidazol-2-yl)pyridinium chloride;

2-[[(2-chloroallyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

4-methoxy-3-methyl-2-[[(o-nitrobenzyl)dithio]methyl]-1-(1,5,6,7-tetrahydro-5,5,7,7-tetramethyl-6-oxoindeno[5,6-d]imidazol-2-yl)pyridinium chloride;

2-[[(3,4-dichlorophenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[(P-methoxyphenyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride;

2-[[[-1-[(carboxymethyl)carbamoyl]ethyl]dithio]methyl]-4-methoxy-3-methyl-1-(1,5,6,7-tetrahydro-5,5,7,7-tetramethyl-6-oxoindeno[5,6-d]imidazol-2-yl)pyridinium chloride; and 2-[[(o-chlorophenyl)dithio]methyl]-4-methoxy-3,5-dimethyl-1-(1,5,6,7-tetrahydro-5,5,7,7-tetramethyl-6-oxoindeno[5,6-d]imidazol-2-yl)pyridinium chloride.

22. A composition for inhibiting gastric acid secretion comprising an effective amount of a compound of the formula

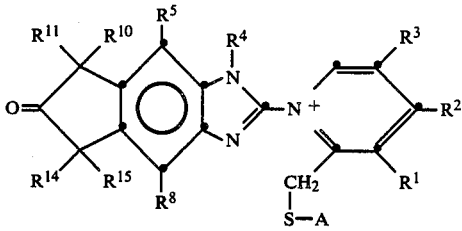

wherein A is —SR$^9$, —SO$_3^-$ or —S—SO$_3^-$; R$^1$ and R$^3$ each is hydrogen or (C$_1$–C$_7$)-alkyl; R$^2$ is hydrogen, (C$_1$–C$_7$)-alkyl, (C$_1$–C$_7$)-alkoxy or a negatively charged oxygen atom; R$^4$ is hydrogen or a negative charge; R$^5$ and R$^8$ each is aryl, arylcarbonyl, aryloxycarbonyl, aryl-(C$_1$–C$_7$)-alkoxycarbonyl, aryloxy, arylcarbonyloxy, aryl-(C$_1$–C$_7$)-alkoxycarbonyloxy or aryloxycarbonyloxy, wherein aryl is phenyl or phenyl substituted by substituents selected from the group consisting of halogen, trifluoromethyl, nitro, (C$_1$–C$_7$)-alkyl, carboxy, (C$_1$–C$_7$)-alkoxycarbonyl, amino, amino mono-substituted by (C$_1$–C$_7$)-alkyl or (C$_1$–C$_7$)-alkanoyl, amino disubstituted by (C$_1$–C$_7$)-alkyl and (C$_1$–C$_7$)-alkanoyl or amino substituted by two (C$_1$–C$_7$)-alkyl groups; halogen, cyano, nitro, formyl, (C$_2$–C$_7$)-alkanoyl, carboxy, carboxy-(C$_1$–C$_7$)-alkyl, (C$_1$–C$_7$)-alkoxycarbonyl, (C$_1$–C$_7$)-alkoxycarbonyl-(C$_1$–C$_7$)-alkyl, carbamoyl, mono- or di-(C$_1$–C$_7$)-alkylcarbamoyl, pyrrolidinocarbonyl, piperidinocarbonyl, carbamoyl-(C$_1$–C$_7$)-alkyl, mono- or di-(C$_1$–C$_7$)-alkylcarbamoyl-(C$_1$–C$_7$)-alkyl, pyrrolidinocarbonyl-(C$_1$–C$_7$)-alkyl, piperidino-carbonyl-(C$_1$–C$_7$)-alkyl, hydroxy, (C$_1$–C$_7$)-alkoxy, (C$_2$–C$_7$)-alkanoyloxy, (C$_1$–C$_7$)-alkoxycarbonyloxy, carbamoyloxy, mono- or di-(C$_1$–C$_7$)-alkylcarbamoyloxy, pyrrolidinocarbonyloxy, piperidinocarbonyloxy, hydroxy-(C$_1$–C$_7$)-alkyl, trifluoromethyl, di-(C$_1$–C$_7$)-alkoxymethyl or (C$_2$–C$_3$)-alkylenedioxymethyl, hydrogen or (C$_1$–C$_7$)-alkyl, R$^{10}$, R$^{11}$, R$^{14}$ and R$^{15}$ each is (C$_1$–C$_7$)-alkyl; and R$^9$ is (C$_1$–C$_{20}$)-alkyl, (C$_3$–C$_7$)-cycloalkyl, (C$_3$–C$_7$)-alkenylalkyl, (C$_3$–C$_7$)-alkynylalkyl, (C$_3$–C$_7$)-alkenyl-alkyl which is substituted vinylically by halogen; aryl, aryl-(C$_1$–C$_7$)-alkyl wherein aryl is phenyl or phenyl substituted by substituents selected from the group consisting of halogen, trifluoromethyl, nitro, (C$_1$–C$_7$)-alkyl, carboxy, (C$_1$–C$_7$)-alkoxycarbonyl, amino, amino mono-substituted by (C$_1$–C$_7$)-alkyl or (C$_1$–C$_7$)-alkanoyl, amino di-substituted by (C$_1$–C$_7$)-alkyl and (C$_1$–C$_7$)-alkanoyl or amino substituted by two (C$_1$–C$_7$)-alkyl groups; hydroxy-(C$_2$–C$_7$)-alkyl, (C$_1$–C$_7$)-alkoxy-(C$_2$–C$_7$)-alkyl, (C$_1$–C$_7$)-alkoxycarbonyl-(C$_1$–C$_7$)-alkyl, carboxy-(C$_1$–C$_7$)-alkyl, di-(C$_1$–C$_7$)-alkyoxycarbonyl-(C$_2$–C$_7$)-alkyl, dicarboxy-(C$_2$–C$_7$)-alky, carboxy-(C$_1$–C$_7$)-alkylcarbamoyl-(C$_1$–C$_7$)-alkyl, amino-(C$_2$–C$_7$)-alkyl, amino-(C$_2$–C$_7$)-alkyl which is mono-substituted by (C$_1$–C$_7$)-alkyl or (C$_1$–C$_7$)-alkanoyl or amino-(C$_2$–C$_7$)-alkyl which is di-substituted by (C$_1$–C$_7$)-alkyl and (C$_1$–C$_7$)-alkanoyl or by two (C$_1$–C$_7$)-alkyl groups, amino-carboxy-(C$_2$–C$_7$)-alkyl, amino-carboxy-(C$_2$–C$_7$)-alkyl which is mono-substituted by (C$_1$–C$_7$)-alkyl or (C$_1$–C$_7$)-alkanoyl or amino-carboxy-(C$_2$–C$_7$)-alkyl which is di-substituted by (C$_1$–C$_7$)-alkyl and (C$_1$–C$_7$)-alkanoyl or by two (C$_1$–C$_7$)-alkyl groups, amino-(C$_1$–C$_7$)-alkoxycarbonyl-(C$_2$–C$_7$)-alkyl, amino-(C$_1$–C$_7$)-alkoxycarbonyl-(C$_2$–C$_7$)-alkyl which is mono-substituted by (C$_1$–C$_7$)-alkyl or (C$_1$–C$_7$)-alkanoyl or amino-(C$_1$–C$_7$)-alkoxycarbonyl-(C$_2$–C$_7$)-alkyl which is di-substituted by (C$_1$–C$_7$)-alkyl and (C$_1$–C$_7$)-alkanoyl or by two (C$_1$–C$_7$)-alkyl groups, whereby the compound is non-charged or has a net single positive charge provided that when there is a net single positive charge there is an external anion, or a pharmaceutically acceptable acid addition salt thereof, and a pharmaceutically inert excipient.

23. A composition in accordance with claim 22, wherein R$^1$ is (C$_1$–C$_7$)-alkyl, R$^2$ is (C$_1$–C$_7$)-alkoxy, R$^3$ is hydrogen or (C$_1$–C$_7$)-alkyl, A is —SR$^9$, R$^9$ is n-propyl, 2-amino-2-carboxyethyl, 2-(4-amino-4-carboxybutyramido)-2-(carboxymethylcarbamoyl) ethyl, n-hexyl, o-chlorophenyl, ethyl, 2-aminoethyl, m-chlorophenyl, 1,2-bis-(ethoxycarbonyl)-ethyl, 2-amino-2-ethoxycarbonylethyl, 2-hydroxyethyl, 3-amino-3-carboxypropyl, cyclopentyl, 2-dimethylamino-ethyl, o-carboxyphenyl, isopropyl, 2-pyridmidinyl, p-fluorophenyl, 2-carboxyethyl, 1-carboxyethyl, p-chlorophenyl, n-pentyl, 2-chloroallyl, o-nitrobenzyl, 3,4-dichlorophenyl, p-methoxyphenyl, 1-[(carboxymethyl)carbamoyl]ethyl or o-chlorophenyl, R$^5$ and R8 each is hydrogen R$_{10}$, R$^{11}$, R$^{14}$ and R$^{15}$ each is methyl.

24. A composition in accordance with claim 22 wherein R$_{10}$, R$^{11}$, R$^{14}$ and R$^{15}$ all are methyl.

25. A composition in accordance with claim 24, wherein the compound of formula I is 2-[[(2-hydroxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride.

26. A composition of inhibiting gastric acid secretion which comprises administering to a warmblooded animal requiring such treatment a composition in accordance with claim 22.

27. A method of controlling or preventing ulcers which comprises administering to a warmblooded animal requiring such treatment a composition in accordance with claim 22.

28. A method in accordance with claim 26, wherein R$^1$ is (C$_1$–C$_7$)-alkyl, R$^2$ is (C$_1$–C$_7$)-alkoxy, R$^3$ is hydrogen or (C$_1$–C$_7$)-alkyl, A is —SR$^9$, R$^9$ is n-propyl, 2-amino-2-carboxyethyl, 2-(4-amino-4-carboxybutyramido)-2-(carboxymethylcarbamoyl) ethyl, n-hexyl, o-chlorophenyl, ethyl, 2-aminoethyl, m-chlorophenyl, 1,2-bis-(ethoxycarbonyl)-ethyl, 2-amino-2-ethoxycarbonylethyl, 2-hydroxyethyl, 3-amino-3-carboxypropyl, cyclopentyl, 2-dimethylamino-ethyl, o-carboxyphenyl, isopropyl, 2-pyridmidinyl, p-fluorophenyl, 2-carboxyethyl, 1-carboxyethyl, p-chlorophenyl, n-pentyl, 2-chloroallyl, o-nitrobenzyl, 3,4-dichlorophenyl, p-methoxyphenyl, 1-[(carboxymethyl)carbamoyl]ethyl or o-chlorophenyl, R$^5$ and R$^8$ each is hydrogen R$^{10}$, R$^{11}$, R$^{14}$ and R$^{15}$ each is methyl.

29. A method in accordance with claim 27, wherein R$^1$ is (C$_1$–C$_7$)-alkyl, R$^2$ is (C$_1$–C$_7$)-alkoxy, R$^3$ is hydrogen or (C$_1$–C$_7$)-alkyl, A is —SR$^9$, R$^9$ is n-propyl, 2-amino-2-carboxyethyl, 2-(4-amino-4-carboxybutylramido)-2-(carboxy-methylcarbamoyl) ethyl, n-hexyl, o-chlorophenyl, ethyl, 2-aminoethyl, m-chlorophenyl, 1,2-bis-(ethoxycarbonyl)-ethyl, 2-amino-2-ethoxycarbonylethyl, 2-hydroxyethyl, 3-amino-3-carboxypropyl, cyclopentyl, 2-dimethylamino-ethyl, o-carboxyphenyl, isopropyl, 2-pyrimidinyl, p-fluorophenyl, 2-carboxyethyl, 1-carboxyethyl, p-chlorophenyl, n-pentyl, 2-chloroallyl, o-nitrobenzyl, 3,4-dichlorophenyl, p-methoxyphenyl, 1-[(carboxymethyl)carbamoyl]ethyl or o-chlorophenyl, $R^5$ and $R^8$ each is hydrogen $R^{10}$, $R^{11}$, $R^{14}$ and $R^{15}$ each is methyl.

30. A method in accordance with claim 26 wherein $R^{10}$, $R^{11}$, $R^{14}$ and $R^{15}$ all are methyl.

31. A method in accordance with claim 30 wherein the compound of formula I is 2-[[(2-hydroxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride.

32. A method in accordance with claim 27 wherein $R^{10}$, $R^{11}$, $R^{14}$ and $R^{15}$ all are methyl.

33. A method in accordance with claim 32 wherein the compound of formula I is 2-[[(2-hydroxyethyl)dithio]methyl]-4-methoxy-3-methyl-1-(1,5,6,7-tetrahydro-5,5,7,7-tetramethyl-6-oxoindeno[5,6-d]imidazol-2-yl)pyridinium chloride.

* * * * *